US009505736B2

(12) United States Patent
Dominguez et al.

(10) Patent No.: US 9,505,736 B2
(45) Date of Patent: Nov. 29, 2016

(54) HISTONE DEACETYLASE INHIBITORS AND COMPOSITIONS AND METHODS OF USE THEREOF

(71) Applicant: CHDI Foundation, Inc., New York, NY (US)

(72) Inventors: Celia Dominguez, Los Angeles, CA (US); Perla Breccia, Cambridge (GB); Christopher A. Luckhurst, Cambridge (GB); Roland W. Bürli, Hertfordshire (GB); Andrew J. Stott, Cambridge (GB)

(73) Assignee: CHDI Foundation, Inc., New York, NY (US)

( * ) Notice: Subject to any disclaimer, the term of this patent is extended or adjusted under 35 U.S.C. 154(b) by 0 days.

(21) Appl. No.: 14/414,149

(22) PCT Filed: Jul. 16, 2013

(86) PCT No.: PCT/US2013/050664
§ 371 (c)(1),
(2) Date: Jan. 12, 2015

(87) PCT Pub. No.: WO2014/014900
PCT Pub. Date: Jan. 23, 2014

(65) Prior Publication Data
US 2015/0203468 A1 Jul. 23, 2015

Related U.S. Application Data

(60) Provisional application No. 61/672,232, filed on Jul. 16, 2012.

(51) Int. Cl.
| | |
|---|---|
| *C07D 319/18* | (2006.01) |
| *C07D 213/74* | (2006.01) |
| *C07D 311/58* | (2006.01) |
| *C07D 401/04* | (2006.01) |
| *C07D 237/08* | (2006.01) |
| *C07D 239/26* | (2006.01) |
| *C07D 239/30* | (2006.01) |
| *C07D 239/34* | (2006.01) |
| *C07D 241/12* | (2006.01) |
| *C07D 417/04* | (2006.01) |
| *C07D 263/32* | (2006.01) |
| *C07D 277/30* | (2006.01) |
| *C07D 213/56* | (2006.01) |
| *C07D 213/61* | (2006.01) |
| *C07D 263/56* | (2006.01) |
| *C07D 215/18* | (2006.01) |
| *C07D 277/64* | (2006.01) |
| *C07D 295/155* | (2006.01) |
| *C07C 259/08* | (2006.01) |

(52) U.S. Cl.
CPC ........... *C07D 319/18* (2013.01); *C07C 259/08* (2013.01); *C07D 213/56* (2013.01); *C07D 213/61* (2013.01); *C07D 213/74* (2013.01); *C07D 215/18* (2013.01); *C07D 237/08* (2013.01); *C07D 239/26* (2013.01); *C07D 239/30* (2013.01); *C07D 239/34* (2013.01); *C07D 241/12* (2013.01); *C07D 263/32* (2013.01); *C07D 263/56* (2013.01); *C07D 277/30* (2013.01); *C07D 277/64* (2013.01); *C07D 295/155* (2013.01); *C07D 311/58* (2013.01); *C07D 401/04* (2013.01); *C07D 417/04* (2013.01); *C07B 2200/07* (2013.01); *C07C 2101/02* (2013.01)

(58) Field of Classification Search
IPC ..................... G01N 33/5011,2458/30
See application file for complete search history.

(56) References Cited

U.S. PATENT DOCUMENTS

| | | | |
|---|---|---|---|
| 7,576,108 B2 * | 8/2009 | Weichert | C07D 261/14 514/363 |
| 2009/0181943 A1 | 7/2009 | Tessier et al. | |
| 2010/0152254 A1 | 6/2010 | Bialer et al. | |
| 2010/0168463 A1 | 7/2010 | Hirata et al. | |

FOREIGN PATENT DOCUMENTS

| | | |
|---|---|---|
| EP | 2060565 | 5/2009 |
| WO | WO 02/22577 | 3/2002 |

(Continued)

OTHER PUBLICATIONS

Braña et al., "Synthesis and Biological Evaluation of Novel 2-(1H-imidazol-4-yl)cyclopropane carboxylic Acids: Key Intermediates for H₃ Histamine Receptor Ligands", Bioorganic & Medicinal Chemistry Letters (2002), vol. 12, No. 24, pp. 3561-3563.
Eyal et al., "Histone deacetylases inhibition and tumor cells cytotoxicity by CNDS-active VPA constitutional isomers and derivatives", Biochemical Pharmacology (2005), vol. 69, No. 10, pp. 1501-1508.
Pellicciari et al., "Syntheis and Pharacological Characterization of All Sixteen Stereoisomers of 2-(2'-Carboxy-3'-phenylcyclopropyl)glycine. Focus on (2S,1'S,2'S,3'R)-2-(2'-Carboxy-3'-phenylcyclopropyl)glycine, a Novel and Selective Group II Metabotropic Glutamate Receptors Antagonist", Journal of Medicinal Chemistry (1996), vol. 39, No. 11, pp. 2259-2269.
International Search Report dated May 10, 2012 and International Preliminary Report on Patentability and Written Opinion for PCT/US2012/022216 dated Jul. 30, 2013 (8 pages).
International Search Report dated Dec. 19, 2013 and International Preliminary Report on Patentability and Written Opinion for PCT/US2013/050664 dated Jan. 20, 2015 (10 pages).

(Continued)

*Primary Examiner* — Shirley V Gembeh
(74) *Attorney, Agent, or Firm* — Sheppard Mullin Richter & Hampton LLP

(57) ABSTRACT

Provided are certain histone deacetylase (HDAC) inhibitors of Formula I, compositions thereof, and methods of their use.

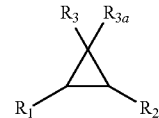

Formula I

21 Claims, No Drawings

(56) References Cited

FOREIGN PATENT DOCUMENTS

WO    WO2005011661 A1    2/2005
WO    WO 2005/028447     3/2005

OTHER PUBLICATIONS

Search Report for Singapore Application No. 201305550-4 dated Jul. 4, 2015 (7 pages).
English Translation of the TIPO's Search Report for ROC Patent Application No. 101102386 dated Apr. 22, 2015 (1 page).
Supplementary European Search Report for EP 12 73 8982 dated Jun. 13, 2014 (9 pages).
Walbrick et al., "A General Method for Synthesizing Optically Active 1,3-Disubstituted Allene Hydrocarbons", Journal of the American Chemical Society (1968), vol. 90, No. 11, pp. 2895-2901.
Warner et al., "Electron Demand in the Transition State of the Cyclopropylidene to Allen Ring Opening", J. Org. Chem. (1992), vol. 57, No. 23, pp. 6294-6300.
Wasa et al., "Pd(II)-Catalyzed Enantioselective C—H Activation of Cyclopropanes," J. Am. Chem. Soc. (2011), vol. 133, No. 49, pp. 19598-19601.

* cited by examiner

HISTONE DEACETYLASE INHIBITORS AND COMPOSITIONS AND METHODS OF USE THEREOF

This application claims the benefit of priority under 35 U.S.C. §371 of PCT International Application No. PCT/US2013/050664, filed Jul. 16, 2013, which in turn claims the benefit of priority to U.S. provisional application 61/672,232, filed Jul. 16, 2012, which is incorporated herein by reference for all purposes.

Provided herein are certain histone deacetylase (HDAC) inhibitors, compositions thereof, and methods of their use.

Histone deacetylases (HDACs) are zinc-containing enzymes which catalyse the removal of acetyl groups from the ϵ-amino termini of lysine residues clustered near the amino terminus of nucleosomal histones. There are 11 known metal-dependent human histone deacetylases, grouped into four classes based on the structure of their accessory domains. Class I includes HDAC1, HDAC2, HDAC3, and HDAC8 and have homology to yeast RPD3. HDAC4, HDAC5, HDAC7, and HDAC9 belong to Class IIa and have homology to yeast HDAC1. HDAC6 and HDAC10 contain two catalytic sites and are classified as Class IIb, whereas HDAC11 has conserved residues in its catalytic center that are shared by both Class I and Class II deacetylases and is sometimes placed in Class IV.

Provided is a compound of Formula I

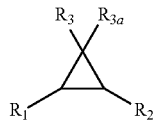

Formula I or a pharmaceutically acceptable salt thereof wherein:
$R_1$ and $R_2$ are independently chosen from optionally substituted aryl and optionally substituted heteroaryl;
$R_3$ is chosen from —C(O)NH(OH) and —N(OH)C(O)$R_4$;
$R_{3a}$ is halo; and
$R_4$ is chosen from hydrogen and lower alkyl.

Also provided is a pharmaceutical composition comprising a compound, or a pharmaceutically acceptable salt thereof, described herein and at least one pharmaceutically acceptable excipient.

Also provided is a method of treating a condition or disorder mediated by at least one histone deacetylase in a subject in need of such a treatment which method comprises administering to the subject a therapeutically effective amount of a compound, or a pharmaceutically acceptable salt thereof, described herein.

As used in the present specification, the following words, phrases and symbols are generally intended to have the meanings as set forth below, except to the extent that the context in which they are used indicates otherwise.

A dash ("-") that is not between two letters or symbols is used to indicate a point of attachment for a substituent. For example, —CONH$_2$ is attached through the carbon atom.

By "optional" or "optionally" is meant that the subsequently described event or circumstance may or may not occur, and that the description includes instances where the event or circumstance occurs and instances in which it does not. For example, "optionally substituted alkyl" encompasses both "alkyl" and "substituted alkyl" as defined below. It will be understood by those skilled in the art, with respect to any group containing one or more substituents, that such groups are not intended to introduce any substitution or substitution patterns that are sterically impractical, synthetically non-feasible and/or inherently unstable.

"Alkyl" encompasses straight chain and branched chain having the indicated number of carbon atoms, usually from 1 to 20 carbon atoms, for example 1 to 8 carbon atoms, such as 1 to 6 carbon atoms. For example $C_1$-$C_6$ alkyl encompasses both straight and branched chain alkyl of from 1 to 6 carbon atoms. Examples of alkyl groups include methyl, ethyl, propyl, isopropyl, n-butyl, sec-butyl, tert-butyl, pentyl, 2-pentyl, isopentyl, neopentyl, hexyl, 2-hexyl, 3-hexyl, 3-methylpentyl, and the like. Alkylene is another subset of alkyl, referring to the same residues as alkyl, but having two points of attachment. Alkylene groups will usually have from 2 to 20 carbon atoms, for example 2 to 8 carbon atoms, such as from 2 to 6 carbon atoms. For example, $C_0$ alkylene indicates a covalent bond and $C_1$ alkylene is a methylene group. When an alkyl residue having a specific number of carbons is named, all geometric isomers having that number of carbons are intended to be encompassed; thus, for example, "butyl" is meant to include n-butyl, sec-butyl, isobutyl and t-butyl; "propyl" includes n-propyl and isopropyl. "Lower alkyl" refers to alkyl groups having 1 to 4 carbons.

"Cycloalkyl" indicates a non-aromatic, fully saturated carbocyclic ring having the indicated number of carbon atoms, for example, 3 to 10, or 3 to 8, or 3 to 6 ring carbon atoms. Cycloalkyl groups may be monocyclic or polycyclic (e.g., bicyclic, tricyclic). Examples of cycloalkyl groups include cyclopropyl, cyclobutyl, cyclopentyl, cyclopentenyl and cyclohexyl, as well as bridged and caged ring groups (e.g., norbornane, bicyclo[2.2.2]octane). In addition, one ring of a polycyclic cycloalkyl group may be aromatic, provided the polycyclic cycloalkyl group is bound to the parent structure via a non-aromatic carbon. For example, a 1,2,3,4-tetrahydronaphthalen-1-yl group (wherein the moiety is bound to the parent structure via a non-aromatic carbon atom) is a cycloalkyl group, while 1,2,3,4-tetrahydronaphthalen-5-yl (wherein the moiety is bound to the parent structure via an aromatic carbon atom) is not considered a cycloalkyl group.

By "alkoxy" is meant an alkyl group of the indicated number of carbon atoms attached through an oxygen bridge such as, for example, methoxy, ethoxy, propoxy, isopropoxy, n-butoxy, sec-butoxy, tert-butoxy, pentoxy, 2-pentyloxy, isopentoxy, neopentoxy, hexoxy, 2-hexoxy, 3-hexoxy, 3-methylpentoxy, and the like. Alkoxy groups will usually have from 1 to 6 carbon atoms attached through the oxygen bridge. "Lower alkoxy" refers to alkoxy groups having 1 to 4 carbons.

"Aryl" indicates an aromatic carbon ring having the indicated number of carbon atoms, for example, 6 to 12 or 6 to 10 carbon atoms. Aryl groups may be monocyclic or polycyclic (e.g., bicyclic, tricyclic). In some instances, both rings of a polycyclic aryl group are aromatic (e.g., naphthyl). In other instances, polycyclic aryl groups may include a non-aromatic ring (e.g., cycloalkyl, cycloalkenyl, heterocycloalkyl, heterocycloalkenyl) fused to an aromatic ring, provided the polycyclic aryl group is bound to the parent structure via an atom in the aromatic ring. Thus, a 1,2,3,4-tetrahydronaphthalen-5-yl group (wherein the moiety is bound to the parent structure via an aromatic carbon atom) is considered an aryl group, while 1,2,3,4-tetrahydronaphthalen-1-yl (wherein the moiety is bound to the parent structure via a non-aromatic carbon atom) is not considered an aryl group. Similarly, a 1,2,3,4-tetrahydroquinolin-8-yl group (wherein the moiety is bound to the parent structure via an aromatic carbon atom) is considered an aryl group, while 1,2,3,4-tetrahydroquinolin-1-yl group (wherein the moiety is bound to the parent structure via a non-aromatic nitrogen atom) is not considered an aryl group. However, the term "aryl" does not encompass or overlap with "heteroaryl", as defined herein, regardless of the point of attachment (e.g., both quinolin-5-yl and quinolin-2-yl are heteroaryl groups). In some instances, aryl is phenyl or naphthyl. In certain instances, aryl is phenyl.

Bivalent radicals formed from substituted benzene derivatives and having the free valences at ring atoms are named as substituted phenylene radicals. Bivalent radicals derived from univalent polycyclic hydrocarbon radicals whose names end in "-yl" by removal of one hydrogen atom from the carbon atom with the free valence are named by adding "-idene" to the name of the corresponding univalent radical, e.g., a naphthyl group with two points of attachment is termed naphthylidene.

The term "halo" includes fluoro, chloro, bromo, and iodo, and the term "halogen" includes fluorine, chlorine, bromine, and iodine.

"Heteroaryl" indicates an aromatic ring containing the indicated number of atoms (e.g., 5 to 12, or 5 to 10 membered heteroaryl) made up of one or more heteroatoms (e.g., 1, 2, 3 or 4 heteroatoms) selected from N, O and S and with the remaining ring atoms being carbon. Heteroaryl groups do not contain adjacent S and O atoms. In some embodiments, the total number of S and O atoms in the heteroaryl group is not more than 2. In some embodiments, the total number of S and O atoms in the heteroaryl group is not more than 1. Unless otherwise indicated, heteroaryl groups may be bound to the parent structure by a carbon or nitrogen atom, as valency permits. For example, "pyridyl" includes 2-pyridyl, 3-pyridyl and 4-pyridyl groups, and "pyrrolyl" includes 1-pyrrolyl, 2-pyrrolyl and 3-pyrrolyl groups. When nitrogen is present in a heteroaryl ring, it may, where the nature of the adjacent atoms and groups permits, exist in an oxidized state (i.e., $N^+$—$O^-$). Additionally, when sulfur is present in a heteroaryl ring, it may, where the nature of the adjacent atoms and groups permits, exist in an oxidized state (i.e., $S^+$—$O^-$ or $SO_2$). Heteroaryl groups may be monocyclic or polycyclic (e.g., bicyclic, tricyclic).

In some instances, a heteroaryl group is monocyclic. Examples include pyrrole, pyrazole, imidazole, triazole (e.g., 1,2,3-triazole, 1,2,4-triazole), tetrazole, furan, isoxazole, oxazole, oxadiazole (e.g., 1,2,3-oxadiazole, 1,2,4-oxadiazole, 1,3,4-oxadiazole), thiophene, isothiazole, thiazole, thiadiazole (e.g., 1,2,3-thiadiazole, 1,2,4-thiadiazole, 1,3,4-thiadiazole), pyridine, pyridazine, pyrimidine, pyrazine, triazine (e.g., 1,2,4-triazine, 1,3,5-triazine) and tetrazine.

In some instances, both rings of a polycyclic heteroaryl group are aromatic. Examples include indole, isoindole, indazole, benzoimidazole, benzotriazole, benzofuran, benzoxazole, benzoisoxazole, benzoxadiazole, benzothiophene, benzothiazole, benzoisothiazole, benzothiadiazole, 1H-pyrrolo[2,3-b]pyridine, 1H-pyrazolo[3,4-b]pyridine, 3H-imidazo[4,5-b]pyridine, 3H-[1,2,3]triazolo[4,5-b]pyridine, 1H-pyrrolo[3,2-b]pyridine, 1H-pyrazolo[4,3-b]pyridine, 1H-imidazo[4,5-b]pyridine, 1H-[1,2,3]triazolo[4,5-b]pyridine, 1H-pyrrolo[2,3-c]pyridine, 1H-pyrazolo[3,4-c]pyridine, 3H-imidazo[4,5-c]pyridine, 3H-[1,2,3]triazolo[4,5-c]pyridine, 1H-pyrrolo[3,2-c]pyridine, 1H-pyrazolo[4,3-c]pyridine, 1H-imidazo[4,5-c]pyridine, 1H-[1,2,3]triazolo[4,5-c]pyridine, furo[2,3-b]pyridine, oxazolo[4,5-b]pyridine, isoxazolo[5,4-b]pyridine, [1,2,3]oxadiazolo[5,4-b]pyridine, furo[3,2-b]pyridine, oxazolo[4,5-b]pyridine, isoxazolo[4,5-b]pyridine, [1,2,3]oxadiazolo[4,5-b]pyridine, furo[2,3-c]pyridine, oxazolo[5,4-c]pyridine, isoxazolo[5,4-c]pyridine, [1,2,3]oxadiazolo[5,4-c]pyridine, furo[3,2-c]pyridine, oxazolo[4,5-c]pyridine, isoxazolo[4,5-c]pyridine, [1,2,3]oxadiazolo[4,5-c]pyridine, thieno[2,3-b]pyridine, thiazolo[5,4-b]pyridine, isothiazolo[5,4-b]pyridine, [1,2,3]thiadiazolo[5,4-b]pyridine, thieno[3,2-b]pyridine, thiazolo[4,5-b]pyridine, isothiazolo[4,5-b]pyridine, [1,2,3]thiadiazolo[4,5-b]pyridine, thieno[2,3-c]pyridine, thiazolo[5,4-c]pyridine, isothiazolo[5,4-c]pyridine, [1,2,3]thiadiazolo[5,4-c]pyridine, thieno[3,2-c]pyridine, thiazolo[4,5-c]pyridine, isothiazolo[4,5-c]pyridine, [1,2,3]thiadiazolo[4,5-c]pyridine, quinoline, isoquinoline, cinnoline, quinazoline, quinoxaline, phthalazine, naphthyridine (e.g., 1,8-naphthyridine, 1,7-naphthyridine, 1,6-naphthyridine, 1,5-naphthyridine, 2,7-naphthyridine, 2,6-naphthyridine), imidazo[1,2-a]pyridine, 1H-pyrazolo[3,4-d]thiazole, 1H-pyrazolo[4,3-d]thiazole and imidazo[2,1-b]thiazole.

In other instances, polycyclic heteroaryl groups may include a non-aromatic ring (e.g., cycloalkyl, cycloalkenyl, heterocycloalkyl, heterocycloalkenyl) fused to a heteroaryl ring, provided the polycyclic heteroaryl group is bound to the parent structure via an atom in the aromatic ring. For example, a 4,5,6,7-tetrahydrobenzo[d]thiazol-2-yl group (wherein the moiety is bound to the parent structure via an aromatic carbon atom) is considered a heteroaryl group, while 4,5,6,7-tetrahydrobenzo[d]thiazol-5-yl (wherein the moiety is bound to the parent structure via a non-aromatic carbon atom) is not considered a heteroaryl group.

"Heterocycloalkyl" indicates a non-aromatic, fully saturated ring having the indicated number of atoms (e.g., 3 to 10, or 3 to 7, membered heterocycloalkyl) made up of one or more heteroatoms (e.g., 1, 2, 3 or 4 heteroatoms) selected from N, O and S and with the remaining ring atoms being carbon. Heterocycloalkyl groups may be monocyclic or polycyclic (e.g., bicyclic, tricyclic).

Examples of monocyclic heterocycloalkyl groups include oxiranyl, aziridinyl, azetidinyl, pyrrolidinyl, imidazolidinyl, pyrazolidinyl, piperidinyl, piperazinyl, morpholinyl and thiomorpholinyl.

When nitrogen is present in a heterocycloalkyl ring, it may, where the nature of the adjacent atoms and groups permits, exist in an oxidized state (i.e., $N^+$—$O^-$). Examples include piperidinyl N-oxide and morpholinyl-N-oxide. Additionally, when sulfur is present in a heterocycloalkyl ring, it may, where the nature of the adjacent atoms and groups permits, exist in an oxidized state (i.e., $S^+$—$O^-$ or —$SO_2$—). Examples include thiomorpholine S-oxide and thiomorpholine S,S-dioxide.

In addition, one ring of a polycyclic heterocycloalkyl group may be aromatic (e.g., aryl or heteroaryl), provided the polycyclic heterocycloalkyl group is bound to the parent structure via a non-aromatic carbon or nitrogen atom. For example, a 1,2,3,4-tetrahydroquinolin-1-yl group (wherein the moiety is bound to the parent structure via a non-aromatic nitrogen atom) is considered a heterocycloalkyl group, while 1,2,3,4-tetrahydroquinolin-8-yl group (wherein the moiety is bound to the parent structure via an aromatic carbon atom) is not considered a heterocycloalkyl group.

"Heterocycloalkenyl" indicates a non-aromatic ring having the indicated number of atoms (e.g., 3 to 10, or 3 to 7, membered heterocycloalkyl) made up of one or more heteroatoms (e.g., 1, 2, 3 or 4 heteroatoms) selected from N, O and S and with the remaining ring atoms being carbon, and at least one double bond derived by the removal of one molecule of hydrogen from adjacent carbon atoms, adjacent nitrogen atoms, or adjacent carbon and nitrogen atoms of the corresponding heterocycloalkyl. Heterocycloalkenyl groups may be monocyclic or polycyclic (e.g., bicyclic, tricyclic). When nitrogen is present in a heterocycloalkenyl ring, it may, where the nature of the adjacent atoms and groups permits, exist in an oxidized state (i.e., $N^+$—$O^-$). Additionally, when sulfur is present in a heterocycloalkenyl ring, it may, where the nature of the adjacent atoms and groups permits, exist in an oxidized state (i.e., S+—$O^-$ or —$SO_2$—). Examples of heterocycloalkenyl groups include dihydrofuranyl (e.g., 2,3-dihydrofuranyl, 2,5-dihydrofuranyl), dihydrothiophenyl (e.g., 2,3-dihydrothiophenyl, 2,5-dihydrothiophenyl), dihydropyrrolyl (e.g., 2,3-dihydro-1H-pyrrolyl, 2,5-dihydro-1H-pyrrolyl), dihydroimidazolyl (e.g., 2,3-dihydro-1H-imidazolyl, 4,5-dihydro-1H-imidazolyl), pyranyl, dihydropyranyl (e.g., 3,4-dihydro-2H-pyranyl, 3,6-dihydro-2H-pyranyl), tetrahydropyridinyl (e.g., 1,2,3,4-tetrahydropyridinyl, 1,2,3,6-tetrahydropyridinyl) and dihydropyridine (e.g., 1,2-dihydropyridine, 1,4-dihydropyridine). In addition, one ring of a polycyclic heterocycloalkenyl group may be aromatic (e.g., aryl or heteroaryl), provided the polycyclic heterocycloalkenyl group is bound to the parent structure via a non-aromatic carbon or nitrogen atom. For example, a 1,2-dihydroquinolin-1-yl group (wherein the moiety is bound to the parent structure via a non-aromatic nitrogen atom) is considered a heterocycloalkenyl group, while 1,2-dihydroquinolin-8-yl group (wherein the moiety is bound to the parent structure via an aromatic carbon atom) is not considered a heterocycloalkenyl group.

The term "substituted", as used herein, means that any one or more hydrogens on the designated atom or group is replaced with a selection from the indicated group, provided that the designated atom's normal valence is not exceeded. When a substituent is oxo (i.e., =O) then 2 hydrogens on the atom are replaced. Combinations of substituents and/or variables are permissible only if such combinations result in stable compounds or useful synthetic intermediates. A stable compound or stable structure is meant to imply a compound that is sufficiently robust to survive isolation from a reaction mixture, and subsequent formulation as an agent having at least practical utility. Unless otherwise specified, substituents are named into the core structure. For example, it is to be understood that when (cycloalkyl)alkyl is listed as a possible substituent, the point of attachment of this substituent to the core structure is in the alkyl portion.

The terms "substituted" alkyl (including without limitation lower alkyl), cycloalkyl, aryl, heterocycloalkyl, and heteroaryl, unless otherwise expressly defined, refer respectively to alkyl, cycloalkyl, aryl, heterocycloalkyl, and heteroaryl wherein one or more (such as up to 5, for example, up to 3) hydrogen atoms are replaced by a substituent independently chosen from —$R^a$, —$OR^b$, —O($C_1$-$C_2$ alkyl)O— (e.g., methylenedioxy-), —$SR^b$, guanidine, guanidine wherein one or more of the guanidine hydrogens are replaced with a lower-alkyl group, —$NR^bR^c$, halo, cyano, oxo (as a substituent for heterocycloalkyl), nitro, —$COR^b$, —$CO_2R^b$, —$CONR^bR^c$, —$OCOR^b$, —$OCO_2R^a$, —$OCONR^bR^c$, —$NR^cCOR^b$, —$NR^cCO_2R^a$, —$NR^cCONR^bR^c$, —$SOR^a$, —$SO_2R^a$, —$SO_2NR^bR^c$, and —$NR^cSO_2R^a$, where $R^a$ is chosen from optionally substituted $C_1$-$C_6$ alkyl, optionally substituted cycloalkyl, optionally substituted aryl, optionally substituted heterocycloalkyl, and optionally substituted heteroaryl;

$R^b$ is chosen from H, optionally substituted $C_1$-$C_6$ alkyl, optionally substituted aryl, and optionally substituted heteroaryl; and $R^c$ is chosen from hydrogen and optionally substituted $C_1$-$C_4$ alkyl; or $R^b$ and $R^c$, and the nitrogen to which they are attached, form an optionally substituted heterocycloalkyl group; and where each optionally substituted group is unsubstituted or independently substituted with one or more, such as one, two, or three, substituents independently selected from $C_1$-$C_4$ alkyl, $C_3$-$C_6$ cycloalkyl, aryl, heteroaryl, aryl-$C_1$-$C_4$ alkyl-, heteroaryl-$C_1$-$C_4$ alkyl-, $C_1$-$C_4$ haloalkyl-, —$OC_1$-$C_4$ alkyl, —$OC_1$-$C_4$ alkylphenyl, —$OC_3$-$C_6$ cycloalkyl, —$C_1$-$C_4$ alkyl-OH, —$C_1$-$C_4$ alkyl-O—$C_1$-$C_4$ alkyl, —$C_1$-$C_4$ alkyl-O—$C_3$-$C_6$ cycloalkyl, —$OC_1$-$C_4$ haloalkyl, —$OC_3$-$C_6$ halocycloalkyl halo, —OH, —$NH_2$, —$C_1$-$C_4$ alkyl-$NH_2$, —$C_3$-$C_6$ cycloalkyl-$NH_2$, —N($C_1$-$C_4$ alkyl)($C_1$-$C_4$ alkyl), —N($C_3$-$C_6$ cycloalkyl)($C_1$-$C_4$ alkyl), —N($C_3$-$C_6$ cycloalkyl)($C_3$-$C_6$ cycloalkyl), —NH($C_1$-$C_4$ alkyl), —NH ($C_3$-$C_6$ cycloalkyl), —N($C_1$-$C_4$ alkyl)($C_1$-$C_4$ alkylphenyl), —NH($C_1$-$C_4$ alkylphenyl), cyano, nitro, oxo (as a substitutent for heteroaryl), —$CO_2H$, —C(O)O$C_1$-$C_4$ alkyl, —C(O)O$C_3$-$C_6$ cycloalkyl, —CON($C_1$-$C_4$ alkyl)($C_1$-$C_4$ alkyl), —CON($C_3$-$C_6$ cycloalkyl)($C_1$-$C_4$ alkyl), —CON($C_3$-$C_6$ cycloalkyl)($C_3$-$C_6$ cycloalkyl), —CONH($C_1$-$C_4$ alkyl), —CONH($C_3$-$C_6$ cycloalkyl), —$CONH_2$, —NHC(O)($C_1$-$C_4$ alkyl), —NHC(O)($C_3$-$C_6$ cycloalkyl), —NHC(O)(phenyl), —N($C_1$-$C_4$ alkyl)C(O)($C_1$-$C_4$ alkyl), —N($C_1$-$C_4$ alkyl)C(O) ($C_3$-$C_6$ cycloalkyl), —N($C_3$-$C_6$ cycloalkyl)C(O)($C_1$-$C_4$ alkyl), —N($C_3$-$C_6$ cycloalkyl)C(O)($C_3$-$C_6$ cycloalkyl), —N($C_1$-$C_4$ alkyl)C(O)(phenyl), —C(O)$C_1$-$C_4$ alkyl, —C(O)$C_3$-$C_6$ cycloalkyl, —C(O)$C_1$-$C_4$ phenyl, —C(O)$C_1$-$C_4$ haloalkyl, —C(O)$C_3$-$C_6$ halocycloalkyl, —OC(O)$C_1$-$C_4$ alkyl, —OC(O)$C_3$-$C_6$ cycloalkyl, —$SO_2$($C_1$-$C_4$ alkyl), —$SO_2$($C_3$-$C_6$ cycloalkyl), —$SO_2$(phenyl), —$SO_2$($C_1$-$C_4$ haloalkyl), —$SO_2$($C_3$-$C_6$ halocycloalkyl), —$SO_2NH_2$, —$SO_2$NH($C_1$-$C_4$ alkyl), —$SO_2$NH($C_3$-$C_6$ cycloalkyl), —$SO_2$N($C_1$-$C_4$ alkyl)$_2$, —$SO_2$N($C_3$-$C_6$ cycloalkyl)$_2$, —$SO_2$N($C_3$-$C_6$ cycloalkyl)($C_1$-$C_4$ alkyl), —$SO_2$NH(phenyl), —$NHSO_2$($C_1$-$C_4$ alkyl), —$NHSO_2$($C_3$-$C_6$ cycloalkyl), —$NHSO_2$(phenyl), —$NHSO_2$($C_1$-$C_4$ haloalkyl), and —$NHSO_2$($C_3$-$C_6$ halocycloalkyl).

The term "substituted alkoxy" refers to alkoxy wherein the alkyl constituent is substituted (i.e., —O-(substituted alkyl)) wherein "substituted alkyl" is as described herein.

The term "substituted amino" refers to the group —$NHR^d$ or —$NR^dR^d$ where each $R^d$ is independently chosen from hydroxy, optionally substituted alkyl, optionally substituted cycloalkyl, optionally substituted acyl, aminocarbonyl, optionally substituted aryl, optionally substituted heteroaryl, optionally substituted heterocycloalkyl, optionally substituted alkoxycarbonyl, sulfinyl and sulfonyl, each as described herein, and provided that only one $R^d$ may be hydroxyl. The term "substituted amino" also refers to N-oxides of the groups —$NHR^d$, and $NR^dR^d$ each as described above. N-oxides can be prepared by treatment of the corresponding amino group with, for example, hydrogen peroxide or m-chloroperoxybenzoic acid. The person skilled in the art is familiar with reaction conditions for carrying out the N-oxidation.

"Aminocarbonyl" encompasses a group of the formula —(C=O)(optionally substituted amino) wherein substituted amino is as described herein.

"Acyl" refers to the groups (alkyl)-C(O)—; (cycloalkyl)-C(O)—; (aryl)-C(O)—; (heteroaryl)-C(O)—; and (heterocycloalkyl)-C(O)—, wherein the group is attached to the parent structure through the carbonyl functionality and wherein alkyl, cycloalkyl, aryl, heteroaryl, and heterocycloalkyl are as described herein. Acyl groups have the indicated number of carbon atoms, with the carbon of the carbonyl group being included in the numbered carbon atoms. For example a $C_2$ acyl group is an acetyl group having the formula $CH_3(C=O)$—.

By "alkoxycarbonyl" is meant an ester group of the formula (alkoxy)(C=O)— attached through the carbonyl carbon wherein the alkoxy group has the indicated number of carbon atoms. Thus a $C_1$-$C_6$ alkoxycarbonyl group is an alkoxy group having from 1 to 6 carbon atoms attached through its oxygen to a carbonyl linker.

By "amino" is meant the group —$NH_2$.

The term "sulfinyl" includes the groups —S(O)—H, —S(O)-(optionally substituted ($C_1$-$C_6$)alkyl), —S(O)-optionally substituted aryl), —S(O)-optionally substituted heteroaryl), —S(O)-(optionally substituted heterocycloalkyl); and —S(O)-(optionally substituted amino).

The term "sulfonyl" includes the groups —S($O_2$)—H, —S($O_2$)-(optionally substituted ($C_1$-$C_6$)alkyl), —S($O_2$)-optionally substituted aryl), —S($O_2$)-optionally substituted heteroaryl), —S($O_2$)-(optionally substituted heterocycloalkyl), —S($O_2$)-(optionally substituted alkoxy), —S($O_2$)-optionally substituted aryloxy), —S($O_2$)-optionally substituted heteroaryloxy), —S($O_2$)-(optionally substituted heterocyclyloxy); and —S($O_2$)-(optionally substituted amino).

The term "substituted acyl" refers to the groups (substituted alkyl)-C(O)—; (substituted cycloalkyl)-C(O)—; (substituted aryl)-C(O)—; (substituted heteroaryl)-C(O)—; and (substituted heterocycloalkyl)-C(O)—, wherein the group is attached to the parent structure through the carbonyl functionality and wherein substituted alkyl, cycloalkyl, aryl, heteroaryl, and heterocycloalkyl are as described herein.

The term "substituted alkoxy" refers to alkoxy wherein the alkyl constituent is substituted (i.e., —O-(substituted alkyl)) wherein "substituted alkyl" is as described herein.

The term "substituted alkoxycarbonyl" refers to the group (substituted alkyl)-O—C(O)— wherein the group is attached to the parent structure through the carbonyl functionality and wherein substituted alkyl is as described herein.

Compounds described herein include, but are not limited to, their optical isomers, racemates, and other mixtures thereof. In those situations, the single enantiomers or diastereomers, i.e., optically active forms, can be obtained by asymmetric synthesis or by resolution of the racemates. Resolution of the racemates can be accomplished, for example, by conventional methods such as crystallization in the presence of a resolving agent, or chromatography, using, for example a chiral high-pressure liquid chromatography (HPLC) column. In addition, such compounds include Z- and E-forms (or cis- and trans-forms) of compounds with carbon-carbon double bonds. Where compounds described herein exist in various tautomeric forms, the term "compound" is intended to include all tautomeric forms of the compound. Such compounds also include crystal forms including polymorphs and clathrates. Similarly, the term "salt" is intended to include all tautomeric forms and crystal forms of the compound.

"Pharmaceutically acceptable salts" include, but are not limited to salts with inorganic acids, such as hydrochlorate, phosphate, diphosphate, hydrobromate, sulfate, sulfinate, nitrate, and like salts; as well as salts with an organic acid, such as malate, maleate, fumarate, tartrate, succinate, citrate, acetate, lactate, methanesulfonate, p-toluenesulfonate, 2-hydroxyethylsulfonate, benzoate, salicylate, stearate, and alkanoate such as acetate, HOOC—$(CH_2)_n$—COOH where n is 0-4, and like salts. Similarly, pharmaceutically acceptable cations include, but are not limited to sodium, potassium, calcium, aluminum, lithium, and ammonium.

In addition, if the compounds described herein are obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used to prepare non-toxic pharmaceutically acceptable addition salts.

"Prodrugs" described herein include any compound that becomes a compound of Formula I when administered to a patient, e.g., upon metabolic processing of the prodrug. Examples of prodrugs include derivatives of functional groups, such as a carboxylic acid group, in the compounds of Formula I. Exemplary prodrugs of a carboxylic acid group include, but are not limited to, carboxylic acid esters such as alkyl esters, hydroxyalkyl esters, arylalkyl esters, and aryloxyalkyl esters. Other exemplary prodrugs include lower alkyl esters such as ethyl ester, acyloxyalkyl esters such as pivaloyloxymethyl (POM), glycosides, and ascorbic acid derivatives. The term "compound" is intended to include prodrugs.

Other exemplary prodrugs include amides of carboxylic acids. Exemplary amide prodrugs include metabolically labile amides that are formed, for example, with an amine and a carboxylic acid. Exemplary amines include $NH_2$, primary, and secondary amines such as $NHR^x$, and $NR^xR^y$, wherein $R^x$ is hydrogen, ($C_1$-$C_{18}$)-alkyl, ($C_3$-$C_7$)-cycloalkyl, ($C_3$-$C_7$)-cycloalkyl-($C_1$-$C_4$)-alkyl-, ($C_6$-$C_{14}$)-aryl which is unsubstituted or substituted by a residue ($C_1$-$C_2$)-alkyl, ($C_1$-$C_2$)-alkoxy, fluoro, or chloro; heteroaryl-, ($C_6$-$C_{14}$)-aryl-($C_1$-$C_4$)-alkyl- where aryl is unsubstituted or substituted by a residue ($C_1$-$C_2$)-alkyl, ($C_1$-$C_2$)-alkoxy, fluoro, or chloro; or heteroaryl-($C_1$-$C_4$)-alkyl- and in which $R^y$ has the meanings indicated for $R^x$ with the exception of hydrogen or wherein $R^x$ and $R^y$, together with the nitrogen to which they are bound, form an optionally substituted 4- to 7-membered heterocycloalkyl ring which optionally includes one or two additional heteroatoms chosen from nitrogen, oxygen, and sulfur. A discussion of prodrugs is provided in T. Higuchi and V. Stella, Pro-drugs as Novel Delivery Systems, Vol. 14 of the A.C.S. Symposium Series, in Edward B. Roche, ed., Bioreversible Carriers in Drug Design, American Pharmaceutical Association and Pergamon Press, 1987, and in Design of Prodrugs, ed. H. Bundgaard, Elsevier, 1985.

A "solvate" is formed by the interaction of a solvent and a compound. The term "compound" is intended to include solvates of compounds. Similarly, "salts" includes solvates of salts. Suitable solvates are pharmaceutically acceptable solvates, such as hydrates, including monohydrates and hemi-hydrates.

A "chelate" is formed by the coordination of a compound to a metal ion at two (or more) points. The term "compound" is intended to include chelates of compounds. Similarly, "salts" includes chelates of salts.

A "non-covalent complex" is formed by the interaction of a compound and another molecule wherein a covalent bond is not formed between the compound and the molecule. For example, complexation can occur through van der Waals interactions, hydrogen bonding, and electrostatic interactions (also called ionic bonding). Such non-covalent complexes are included in the term "compound".

The term "hydrogen bond" refers to a form of association between an electronegative atom (also known as a hydrogen bond acceptor) and a hydrogen atom attached to a second, relatively electronegative atom (also known as a hydrogen bond donor). Suitable hydrogen bond donor and acceptors are well understood in medicinal chemistry.

"Hydrogen bond acceptor" refers to a group comprising an oxygen or nitrogen, such as an oxygen or nitrogen that is $sp^2$-hybridized, an ether oxygen, or the oxygen of a sulfoxide or N-oxide.

The term "hydrogen bond donor" refers to an oxygen, nitrogen, or heteroaromatic carbon that bears a hydrogen group containing a ring nitrogen or a heteroaryl group containing a ring nitrogen.

As used herein the terms "group", "radical" or "fragment" are synonymous and are intended to indicate functional groups or fragments of molecules attachable to a bond or other fragments of molecules.

The term "active agent" is used to indicate a compound or a pharmaceutically acceptable salt thereof which has biological activity. In some embodiments, an "active agent" is a compound or pharmaceutically acceptable salt thereof having pharmaceutical utility. For example an active agent may be an anti-neurodegenerative therapeutic.

The term "therapeutically effective amount" means an amount effective, when administered to a human or non-human patient, to provide a therapeutic benefit such as amelioration of symptoms, slowing of disease progression, or prevention of disease e.g., a therapeutically effective amount may be an amount sufficient to decrease the symptoms of a disease responsive to inhibition of HDAC activity.

As used herein, the terms "histone deacetylase" and "HDAC" are intended to refer to anyone of a family of enzymes that remove $N^\epsilon$-acetyl groups from the $\epsilon$-amino groups of lysine residues of a protein (for example, a histone, or tubulin). Unless otherwise indicated by context, the term "histone" is meant to refer to any histone protein, including H1, H2A, H2B, H3, H4, and H5, from any species. In some embodiments, the histone deacetylase is a human HDAC, including, but not limited to, HDAC-4, HDAC-5, HDAC-6, HDAC-7, HDAC-9, and HDAC-10. In some embodiments, at least one histone deacetylase is selected from HDAC-4, HDAC-5, HDAC-7, and HDAC-9. In some embodiments, the histone deacetylase is a class IIa HDAC. In some embodiments, the histone deacetylase is HDAC-4. In some embodiments, the histone deacetylase is HDAC-5. In some embodiments, the histone deacetylase is derived from a protozoal or fungal source.

The terms "histone deacetylase inhibitor" and "inhibitor of histone deacetylase" are intended to mean a compound, or a pharmaceutically acceptable salt thereof, described herein which is capable of interacting with a histone deacetylase and inhibiting its enzymatic activity.

The term "a condition or disorder mediated by HDAC" or "a condition or disorder mediated by histone deacetylase" as used herein refers to a condition or disorder in which HDAC and/or the action of HDAC is important or necessary, e.g., for the onset, progress, expression, etc. of that condition, or a condition which is known to be treated by HDAC inhibitors (such as, e.g., trichostatin A).

The term "effect" describes a change or an absence of a change in cell phenotype or cell proliferation. "Effect" can also describe a change or an absence of a change in the catalytic activity of HDAC. "Effect" can also describe a change or an absence of a change in an interaction between HDAC and a natural binding partner.

The term "inhibiting histone deacetylase enzymatic activity" is intended to mean reducing the ability of a histone deacetylase to remove an acetyl group from a protein, such as but not limited to a histone or tubulin. The concentration of inhibitor which reduces the activity of a histone deacetylase to 50% of that of the uninhibited enzyme is determined as the $IC_{50}$ value. In some embodiments, such reduction of histone deacetylase activity is at least 50%, such as at least about 75%, for example, at least about 90%. In some embodiments, histone deacetylase activity is reduced by at least 95%, such as by at least 99%. In some embodiments, the compounds and pharmaceutical acceptable salts thereof described herein have an $IC_{50}$ value less than 100 nanomolar. In some embodiments, the compounds and pharmaceutical acceptable salts thereof described herein have an $IC_{50}$ value from 100 nanomolar to 1 micromolar. In some embodiments, the compounds and pharmaceutical acceptable salts thereof described herein have an $IC_{50}$ value from 1 to 25 micromolar.

In some embodiments, such inhibition is specific, i.e., the histone deacetylase inhibitor reduces the ability of a histone deacetylase to remove an acetyl group from a protein at a concentration that is lower than the concentration of the inhibitor that is required to produce another, unrelated biological effect. In some embodiments, the concentration of the inhibitor required for histone deacetylase inhibitory activity is at least 2-fold lower, such as at least 5-fold lower, for example, at least 10-fold lower, such as at least 20-fold lower than the concentration required to produce an unrelated biological effect.

"Treatment" or "treating" means any treatment of a disease state in a patient, including a) preventing the disease, that is, causing the clinical symptoms of the disease not to develop;

b) inhibiting the disease;

c) slowing or arresting the development of clinical symptoms; and/or d) relieving the disease, that is, causing the regression of clinical symptoms.

"Subject" or "patient" refers to an animal, such as a mammal, that has been or will be the object of treatment, observation or experiment. The methods described herein may be useful in both human therapy and veterinary applications. In some embodiments, the subject is a mammal; and in some embodiments the subject is human.

Provided is a compound of Formula I

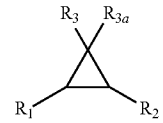

Formula I or a pharmaceutically acceptable salt thereof wherein:
$R_1$ and $R_2$ are independently chosen from optionally substituted aryl and optionally substituted heteroaryl;
$R_3$ is chosen from —C(O)NH(OH) and —N(OH)C(O)$R_4$;
$R_{3a}$ is halo; and
$R_4$ is chosen from hydrogen and lower alkyl.

In some embodiments, $R_1$ is chosen from aryl and heteroaryl, each of which is optionally substituted with 1, 2, or 3 groups independently chosen from
halo,
cyclopropyl,
trifluoromethyl, lower alkyl optionally substituted with 1, 2, or 3 groups independently chosen from halo, lower alkoxy, and hydroxyl, phenyl optionally substituted with 1 or 2 groups independently chosen from cyclopropyl, halo, difluoromethyl, trifluoromethyl, trifluoromethoxy, difluoromethoxy, and lower alkyl, heteroaryl optionally substituted with 1 or 2 groups independently chosen from cyclopropyl, halo, difluoromethyl, trifluoromethyl, trifluoromethoxy, difluoromethoxy, and lower alkyl, and -L-$(CR_5R_6)_n$—N$(R_7)R_8$ where L is chosen from —C(O)NR$_9$— and —NR$_{10}$—, n is 1 or 2, each occurrence of R$_5$ and R$_6$ is independently selected from hydrogen and lower alkyl, R$_7$ is hydrogen or lower alkyl, and R$_8$ is hydrogen or lower alkyl or R$_7$ and R$_8$, taken together with the nitrogen to which they are bound, form an optionally substituted 4- to -8-membered heterocycloalkyl ring, and R$_{10}$ is selected from hydrogen and lower alkyl.

In some embodiments, R$_1$ is chosen from aryl and heteroaryl, each of which is optionally substituted with 1, 2, or 3 groups independently chosen from phenyl optionally substituted with 1 or 2 groups independently chosen from cyclopropyl, halo, difluoromethyl, trifluoromethyl, trifluoromethoxy, difluoromethoxy, and lower alkyl, and heteroaryl optionally substituted with 1 or 2 groups independently chosen from cyclopropyl, halo, difluoromethyl, trifluoromethyl, trifluoromethoxy, difluoromethoxy, and lower alkyl.

In some embodiments, R$_1$ is chosen from 1,2,3,4-tetrahydroquinolin-6-yl, 1H-pyrazol-4-yl, 2,3-dihydrobenzo[b][1,4]dioxin-6-yl, benzo[d]oxazol-6-yl, benzo[d]thiazol-6-yl, chroman-6-yl, phenyl, pyridazin-4-yl, pyridin-3-yl, pyridin-4-yl, and thiazol-5-yl, each of which is optionally substituted with 1, 2, or 3 groups independently chosen from halo, cyclopropyl, lower alkyl optionally substituted with 1, 2, or 3 groups independently chosen from halo, lower alkoxy, and hydroxyl, phenyl optionally substituted with halo, oxazol-5-yl optionally substituted with cyclopropyl, pyrimidin-4-yl optionally substituted with 1 or 2 groups independently chosen from halo, difluoromethoxy, difluoromethyl, trifluoromethoxy, trifluoromethyl and lower alkyl, pyrimidin-2-yl optionally substituted with 1 or 2 groups independently chosen from halo, difluoromethoxy, difluoromethyl, trifluoromethoxy, trifluoromethyl and lower alkyl, pyrimidin-5-yl optionally substituted with 1 or 2 groups independently chosen from halo, difluoromethoxy, difluoromethyl, trifluoromethoxy, trifluoromethyl and lower alkyl, pyrazin-2-yl optionally substituted with 1 or 2 groups independently chosen from halo, difluoromethoxy, difluoromethyl, trifluoromethoxy, trifluoromethyl or lower alkyl, pyridin-2-yl optionally substituted with 1 or 2 groups independently chosen from halo, difluoromethoxy, difluoromethyl, trifluoromethoxy, trifluoromethyl or lower alkyl, and -L-$(CR_5R_6)_n$—N$(R_7)R_8$ where L is chosen from —C(O)NR$_9$— and —NR$_{10}$—, n is 1 or 2, each occurrence of R$_5$ and R$_6$ is independently selected from hydrogen and lower alkyl, R$_7$ is hydrogen or lower alkyl, and R$_8$ is hydrogen or lower alkyl or R$_7$ and R$_8$, taken together with the nitrogen to which they are bound, form an optionally substituted 4- to -8-membered heterocycloalkyl ring, and R$_{10}$ is selected from hydrogen and lower alkyl.

In some embodiments, R$_1$ is chosen from 1,2,3,4-tetrahydroquinolin-6-yl, 1H-pyrazol-4-yl, 2,3-dihydrobenzo[b][1,4]dioxin-6-yl, benzo[d]oxazol-6-yl, benzo[d]thiazol-6-yl, chroman-6-yl, phenyl, pyridazin-4-yl, pyridin-3-yl, pyridin-4-yl, and thiazol-5-yl, each of which is optionally substituted with 1, 2, or 3 groups independently chosen from 2-(trifluoromethyl)pyrimidin-4-yl, 2-cyclopropyloxazol-5-yl, 2-hydroxypropan-2-yl, 4-(trifluoromethyl)pyrimidin-2-yl, 4-fluorophenyl, 5-(trifluoromethyl)pyridin-2-yl, 5-fluoropyrimidin-2-yl, 5-chloropyrimidin-2-yl, 5-methylpyrimidin-2-yl, 5-(difluoromethoxy)pyrimidin-2-yl, 5-(difluoromethyl)pyrimidin-2-yl, 2-methylpyrimidin-5-yl, 5-fluoropyridin-2-yl, 5-(trifluoromethyl)pyrazin-2-yl, bromo, chloro, cyclopropyl, fluoro, and oxazol-5-yl.

In some embodiments, R$_1$ is chosen from aryl and heteroaryl, each of which is optionally substituted with 1, 2, or 3 groups independently chosen from halo, cyclopropyl, trifluoromethyl, lower alkyl optionally substituted with 1 or 2 groups independently chosen from halo, lower alkoxy, and hydroxyl, phenyl optionally substituted with 1 or 2 groups independently chosen from cyclopropyl, halo, trifluoromethyl, and lower alkyl, and heteroaryl optionally substituted with 1 or 2 groups independently chosen from cyclopropyl, halo, trifluoromethyl, and lower alkyl.

In some embodiments, R$_1$ is chosen from 1,2,3,4-tetrahydroquinolin-6-yl, 1H-pyrazol-4-yl, 2,3-dihydrobenzo[b][1,4]dioxin-6-yl, benzo[d]oxazol-6-yl, benzo[d]thiazol-6-yl, chroman-6-yl, phenyl, pyridazin-4-yl, pyridin-4-yl, and thiazol-5-yl, each of which is optionally substituted with 1, 2, or 3 groups independently chosen from halo, cyclopropyl, lower alkyl optionally substituted with hydroxyl, phenyl optionally substituted with halo, oxazol-5-yl optionally substituted with cyclopropyl, pyrimidin-4-yl optionally substituted with 1 or 2 groups independently chosen from halo, trifluoromethyl or lower alkyl, pyrimidin-2-yl optionally substituted with 1 or 2 groups independently chosen from halo, trifluoromethyl and lower alkyl, and pyridin-2-yl optionally substituted with 1 or 2 groups independently chosen from halo, trifluoromethyl and lower alkyl.

In some embodiments, R$_1$ is chosen from 1,2,3,4-tetrahydroquinolin-6-yl, 1H-pyrazol-4-yl, 2,3-dihydrobenzo[b][1,4]dioxin-6-yl, benzo[d]oxazol-6-yl, benzo[d]thiazol-6-yl, chroman-6-yl, phenyl, pyridazin-4-yl, pyridin-4-yl, and thiazol-5-yl, each of which is optionally substituted with 1, 2, or 3 groups independently chosen from 2-(trifluoromethyl)pyrimidin-4-yl, 2-cyclopropyloxazol-5-yl, 2-hydroxypropan-2-yl, 4-(trifluoromethyl)pyrimidin-2-yl, 4-fluorophenyl, 5-(trifluoromethyl)pyridin-2-yl, 5-fluoropyrimidin-2-yl, 5-methylpyrimidin-2-yl, bromo, chloro, cyclopropyl, fluoro, and oxazol-5-yl.

In some embodiments, $R_1$ is chosen from (1-(5-(trifluoromethyl)pyridin-2-yl)-1H-pyrazol-4-yl, 2-(2-(trifluoromethyl)pyrimidin-4-yl)thiazol-5-yl, 2-(2-hydroxypropan-2-yl)benzo[d]oxazol-6-yl, 2-(2-hydroxypropan-2-yl)benzo[d]thiazol-6-yl, 2-(2-hydroxypropan-2-yl)pyridin-4-yl, 2-(2-hydroxypropan-2-yl)thiazol-5-yl, 2-(4-fluorophenyl)thiazol-5-yl, 2-(5-fluoropyrimidin-2-yl)thiazol-5-yl, 2-cyclopropyl-5-fluoropyridin-4-yl, 2-cyclopropylbenzo[d]oxazol-6-yl, 2-cyclopropylpyridin-4-yl, 2-cyclopropylthiazol-5-yl, 3-(2-cyclopropyloxazol-5-yl)phenyl, 3-(5-fluoropyrimidin-2-yl)phenyl, 4-(2-cyclopropyloxazol-5-yl)phenyl, 4-(4-(trifluoromethyl)pyrimidin-2-yl)phenyl, 4-(5-fluoropyrimidin-2-yl)phenyl, 4-(5-methylpyrimidin-2-yl)phenyl, 4-(oxazol-5-yl)phenyl, 4-bromophenyl, 6-cyclopropylpyridazin-4-yl, 8-chloro-2,3-dihydrobenzo[b][1,4]dioxin-6-yl, 8-chloro-4,4-difluoro-1,2,3,4-tetrahydroquinolin-6-yl, and 8-chloro-4,4-difluorochroman-6-yl.

In some embodiments, $R_2$ is chosen from aryl and heteroaryl, each of which is optionally substituted with one or two groups independently chosen from lower alkyl, halo, hydroxyl, and lower alkoxy.

In some embodiments, $R_2$ is chosen from aryl optionally substituted with one or two groups independently chosen from lower alkyl, halo, hydroxyl, and lower alkoxy.

In some embodiments, $R_2$ is chosen from phenyl, 2-methylphenyl, and 3-fluoro-2-methylphenyl.

In some embodiments, $R_2$ is phenyl.

In some embodiments, $R_2$ is chosen from heteroaryl optionally substituted with one or two groups independently chosen from lower alkyl, halo, hydroxyl, and lower alkoxy.

In some embodiments, $R_2$ is chosen from pyridin-3-yl and 6-oxo-1,6-dihydropyridin-2-yl, each of which is optionally substituted with one or two groups independently chosen from lower alkyl, halo, hydroxyl, and lower alkoxy.

In some embodiments, $R_2$ is chosen from 2-methylpyridin-3-yl and 1-methyl-6-oxo-1,6-dihydropyridin-2-yl.

In some embodiments, $R_{3a}$ is fluoro or chloro. In some embodiments, $R_{3a}$ is fluoro.

In some embodiments, $R_3$ is —C(O)NH(OH). In some embodiments, $R_3$ is —N(OH)C(O)$R_4$ wherein $R_4$ is hydrogen. In some embodiments, $R_3$ is —N(OH)C(O) $R_4$ wherein $R_4$ is methyl.

Also provided is a compound of Formula II

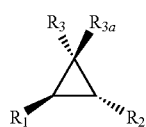

Formula II or a pharmaceutically acceptable salt thereof, wherein $R_1$, $R_2$, $R_3$, and $R_{3a}$ are as described herein.

Also provided is a compound of Formula III

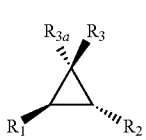

Formula III or a pharmaceutically acceptable salt thereof, wherein $R_1$, $R_2$, $R_3$, and $R_{3a}$ are as described herein.

Also provided is a compound chosen from

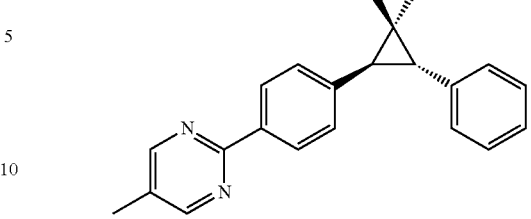

(1S,2S,3S)-1-fluoro-N-hydroxy-2-(4-(5-methylpyrimidin-2-yl)phenyl)-3-phenylcyclopropanecarboxamide

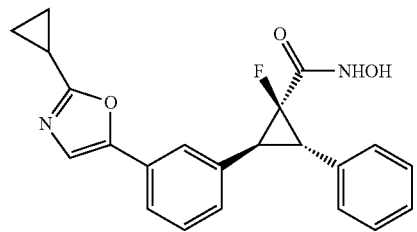

(1S,2S,3S)-2-(3-(2-cyclopropyloxazol-5-yl)phenyl)-1-fluoro-N-hydroxy-3-phenylcyclopropanecarboxamide

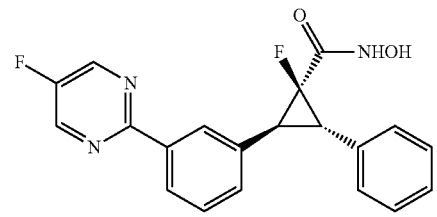

(1S,2S,3S)-1-fluoro-2-(3-(5-fluoropyrimidin-2-yl)phenyl)-N-hydroxy-3-phenylcyclopropanecarboxamide

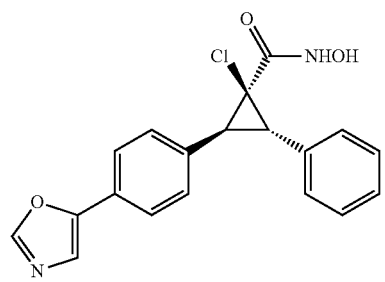

(1S,2S,3S)-1-chloro-N-hydroxy-2-(4-(oxazol-5-yl)phenyl)-3-phenylcyclopropanecarboxamide -continued

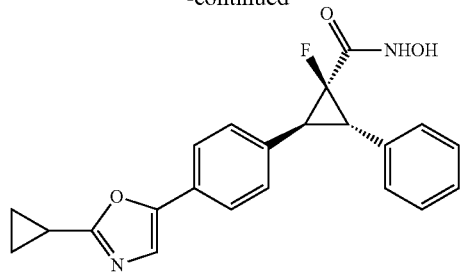

(1S,2S,3S)-2-(4-(2-cyclopropyloxazol-5-yl)phenyl)-1-fluoro-N-hydroxy-3-phenylcyclopropanecarboxamide

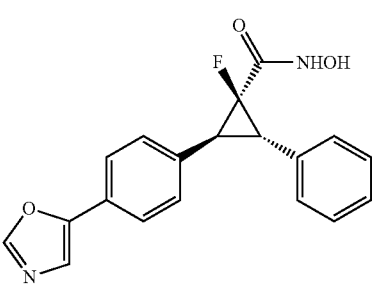

(1S,2S,3S)-1-fluoro-N-hydroxy-2-(4-(oxazol-5-yl)phenyl)-3-phenylcyclopropanecarboxamide

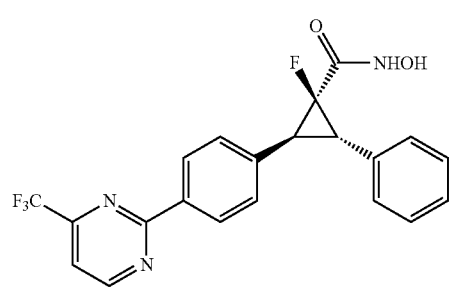

(1S,2S,3S)-1-fluoro-N-hydroxy-2-phenyl-3-(4-(4-(trifluoromethyl)pyrimidin-2-yl)phenyl)cyclopropanecarboxamide

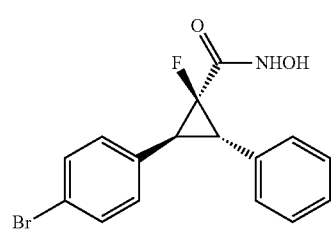

(1S,2S,3S)-2-(4-bromophenyl)-1-fluoro-N-hydroxy-3-phenylcyclopropanecarboxamide

-continued

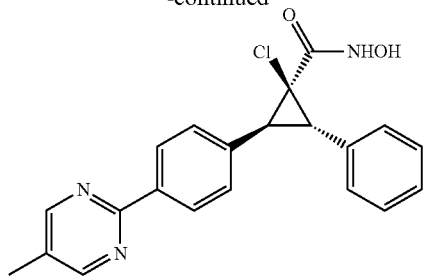

(1S,2S,3S)-1-chloro-N-hydroxy-2-(4-(5-methylpyrimidin-2-yl)phenyl)-3-phenylcyclopropanecarboxamide

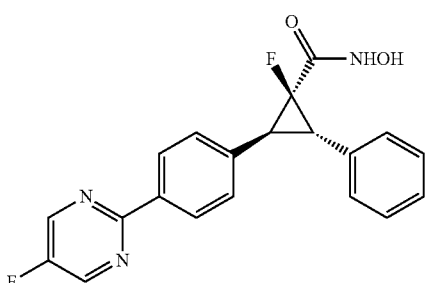

(1S,2S,3S)-1-fluoro-2-(4-(5-fluoropyrimidin-2-yl)phenyl)-N-hydroxy-3-phenylcyclopropanecarboxamide

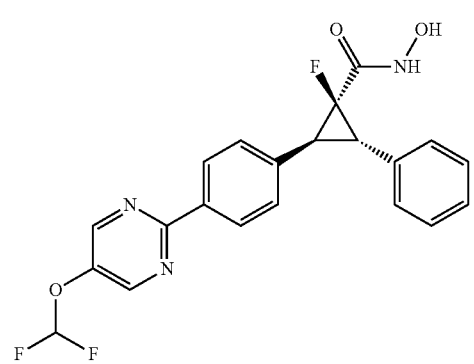

(1S,2S,3S)-2-(4-(5-(difluoromethoxy)pyrimidin-2-yl)phenyl)-1-fluoro-N-hydroxy-3-phenylcyclopropanecarboxamide

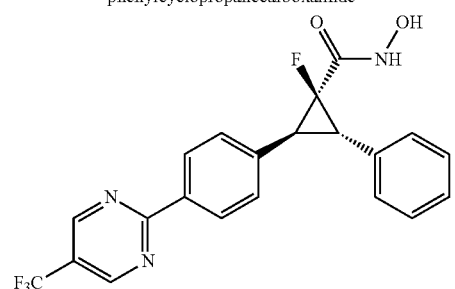

(1S,2S,3S)-1-fluoro-N-hydroxy-2-phenyl-3-(4-(5-(trifluoromethyl)pyrimidin-2-yl)phenyl)cyclopropanecarboxamide -continued

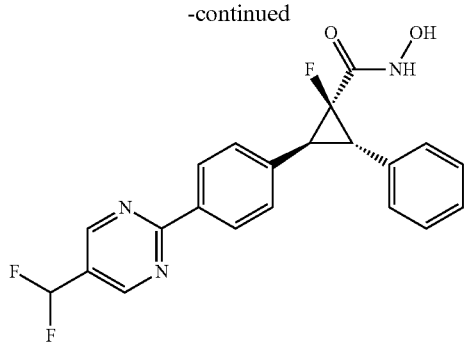

(1S,2S,3S)-2-(4-(5-(difluoromethyl)pyrimidin-2-yl)phenyl)-1-fluoro-N-hydroxy-3-phenylcyclopropanecarboxamide

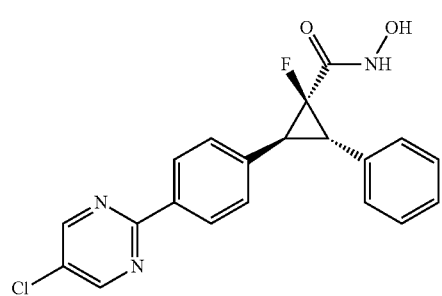

(1S,2S,3S)-2-(4-(5-chloropyrimidin-2-yl)phenyl)-1-fluoro-N-hydroxy-3-phenylcyclopropanecarboxamide

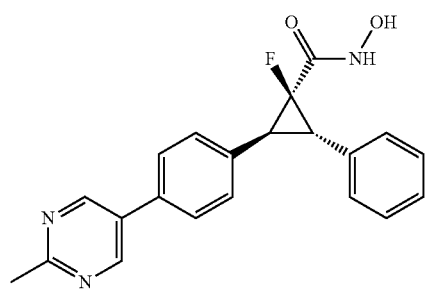

(1S,2S,3S)-1-fluoro-N-hydroxy-2-(4-(2-methylpyrimidin-5-yl)phenyl)-3-phenylcyclopropanecarboxamide

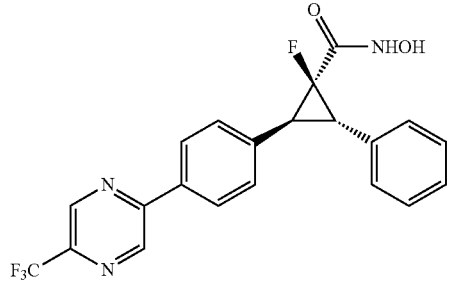

(1S,2S,3S)-1-fluoro-N-hydroxy-2-phenyl-3-(4-(5-(trifluoromethyl)pyrazin-2-yl)phenyl)cyclopropanecarboxamide -continued

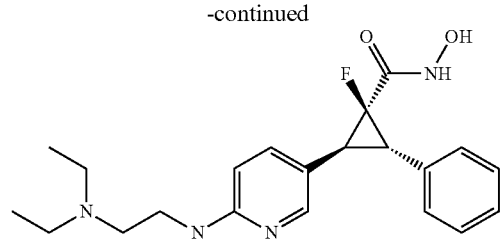

(1S,2S,3S)-2-(6-((2-(diethylamino)ethyl)amino)pyridin-3-yl)-1-fluoro-N-hydroxy-3-phenylcyclopropanecarboxamide

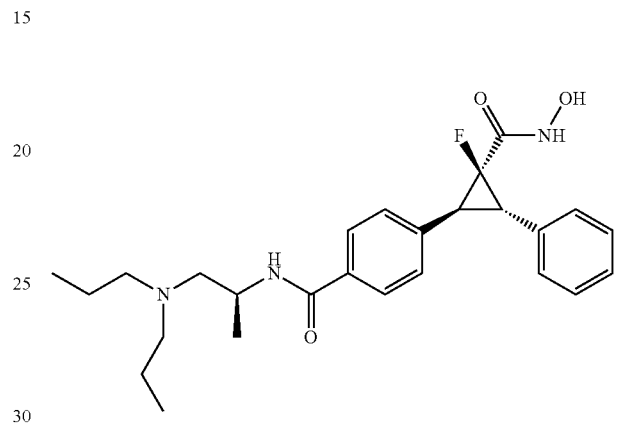

N-((S)-1-(dipropylamino)propan-2-yl)-4-((1S,2S,3S)-2-fluoro-2-(hydroxycarbamoyl)-3-phenylcyclopropyl)benzamide

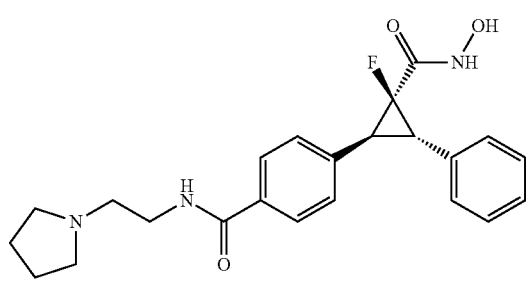

4-((1S,2S,3S)-2-fluoro-2-(hydroxycarbamoyl)-3-phenylcyclopropyl)-N-(2-(pyrrolidin-1-yl)ethyl)benzamide

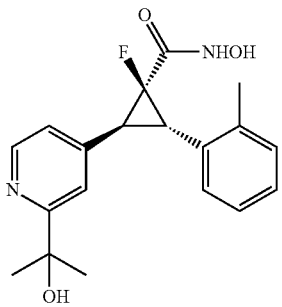

(1R,2S,3S)-1-fluoro-N-hydroxy-2-(2-(2-hydroxypropan-2-yl)pyridin-4-yl)-3-o-tolylcyclopropanecarboxamide -continued

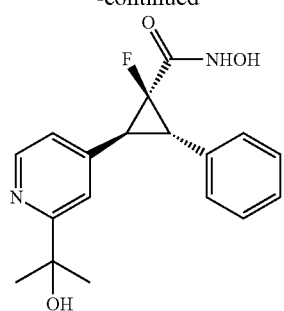

(1S,2S,3S)-1-fluoro-N-hydroxy-2-(2-(2-hydroxypropan-2-yl)pyridin-4-yl)-3-phenylcyclopropanecarboxamide

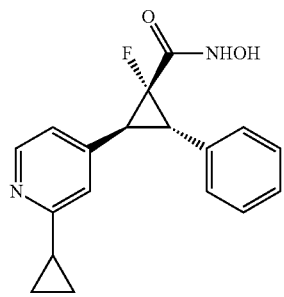

(1R,2S,3S)-2-(2-cyclopropylpyridin-4-yl)-1-fluoro-N-hydroxy-3-phenylcyclopropanecarboxamide

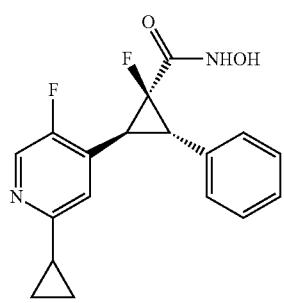

(1S,2S,3S)-2-(2-cyclopropyl-5-fluoropyridin-4-yl)-1-fluoro-N-hydroxy-3-phenylcyclopropanecarboxamide

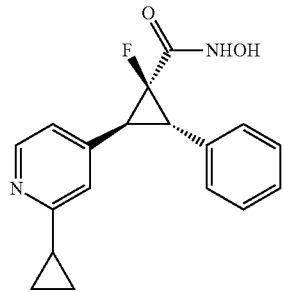

(1S,2S,3S)-2-(2-cyclopropylpyridin-4-yl)-1-fluoro-N-hydroxy-3-phenylcyclopropanecarboxamide -continued

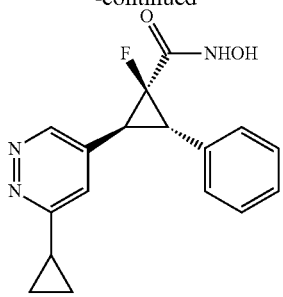

(1S,2S,3S)-2-(6-cyclopropylpyridazin-4-yl)-1-fluoro-N-hydroxy-3-phenylcyclopropanecarboxamide

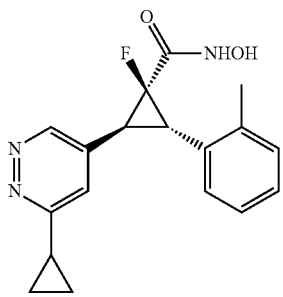

(1S,2S,3S)-2-(6-cyclopropylpyridazin-4-yl)-1-fluoro-N-hydroxy-3-o-tolylcyclopropanecarboxamide

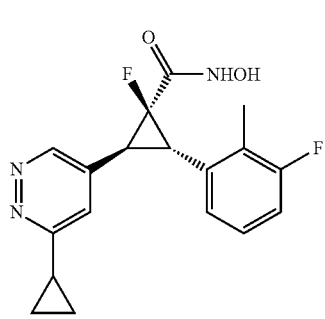

(1S,2S,3S)-2-(6-cyclopropylpyridazin-4-yl)-1-fluoro-3-(3-fluoro-2-methylphenyl)-N-hydroxycyclopropanecarboxamide

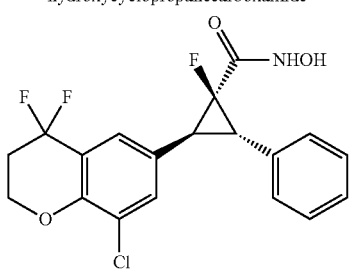

(1S,2S,3S)-2-(8-chloro-4,4-difluorochroman-6-yl)-1-fluoro-N-hydroxy-3-phenylcyclopropanecarboxamide

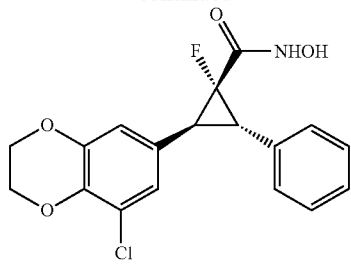

(1R,2S,3S)-2-(8-chloro-2,3-
dihydrobenzo[b][1,4]dioxin-6-yl)-1-
fluoro-N-hydroxy-3-
phenylcyclopropanecarboxamide

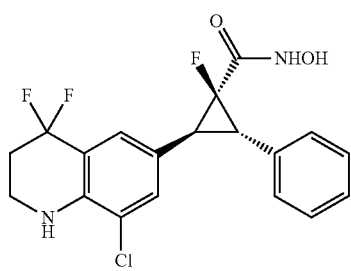

(1S,2S,3S)-2-(8-chloro-4,4-difluoro-
1,2,3,4-tetrahydroquinolin-6-yl)-1-
fluoro-N-hydroxy-3-
phenylcyclopropanecarboxamide

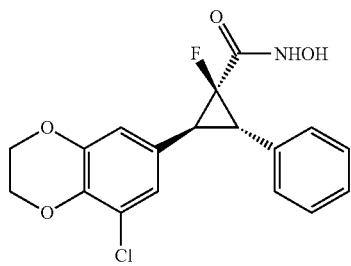

(1S,2S,3S)-2-(8-chloro-2,3-
dihydrobenzo[b][1,4]dioxin-6-yl)-1-
fluoro-N-hydroxy-3-
phenylcyclopropanecarboxamide

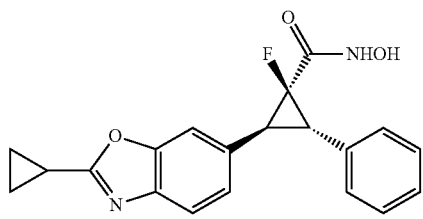

(1S,2S,3S)-2-(2-
cyclopropylbenzo[d]oxazol-6-yl)-1-
fluoro-N-hydroxy-3-
phenylcyclopropanecarboxamide

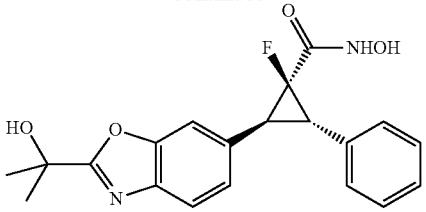

(1S,2S,3S)-1-fluoro-N-hydroxy-2-(2-
(2-hydroxypropan-2-
yl)benzo[d]oxazol-6-yl)-3-
phenylcyclopropanecarboxamide

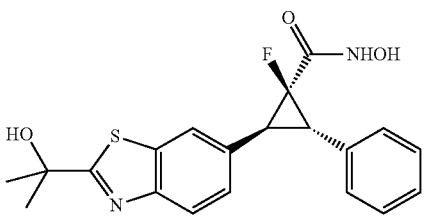

(1S,2S,3S)-1-fluoro-N-hydroxy-2-(2-
(2-hydroxypropan-2-
yl)benzo[d]thiazol-6-yl)-3-
phenylcyclopropanecarboxamide

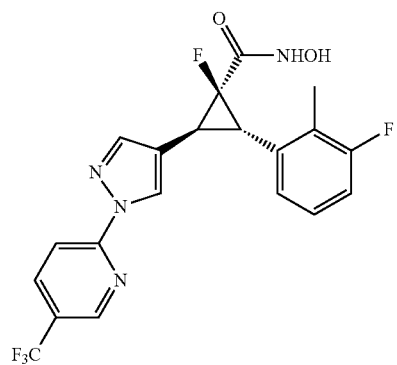

(1S,2S,3S)-1-fluoro-2-(3-fluoro-2-
methylphenyl)-N-hydroxy-3-(1-(5-
(trifluoromethyl)pyridin-2-yl)-1H-
pyrazol-4-
yl)cyclopropanecarboxamide

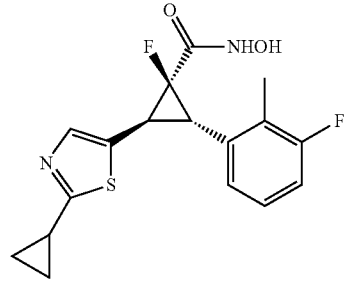

(1S,2R,3S)-2-(2-cyclopropylthiazol-
5-yl)-1-fluoro-3-(3-fluoro-2-
methylphenyl)-N-
hydroxycyclopropanecarboxamide -continued

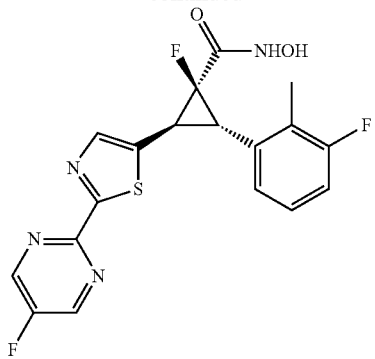

(1S,2S,3R)-1-fluoro-2-(3-fluoro-2-methylphenyl)-3-(2-(5-flouropyrimidin-2-yl)thiazol-5-yl)-N-hydroxycyclopropanecarboxamide

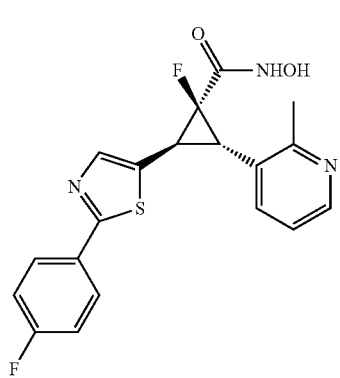

(1S,2R,3S)-1-fluoro-2-(2-(4-flourophenyl)thiazol-5-yl)-N-hydroxy-3-(2-methylpyridin-3-yl)cyclopropanecarboxamide and

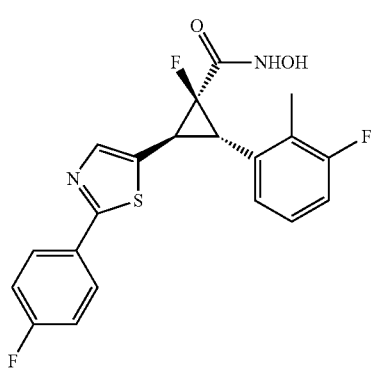

(1S,2S,3R)-1-fluoro-2-(3-fluoro-2-methylphenyl)-3-(2-(4-fluorophenyl)thiazol-5-yl)-N-hydroxycyclopropanecarboxamide -continued

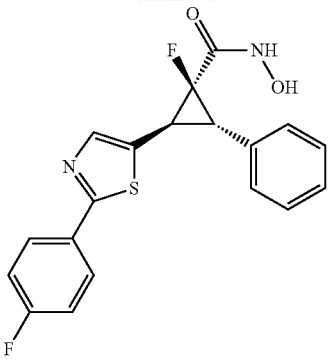

(1S,2R,3S)-1-fluoro-2-(2-(4-fluorophenyl)thiazol-5-yl)-N-hydroxy-3-phenylcyclopropanecarboxamide

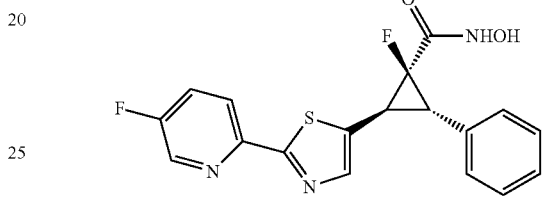

(1S,2R,3S)-1-fluoro-2-(2-(5-fluoropyridin-2-yl)thiazol-5-yl)-N-hydroxy-3-phenylcyclopropanecarboxamide

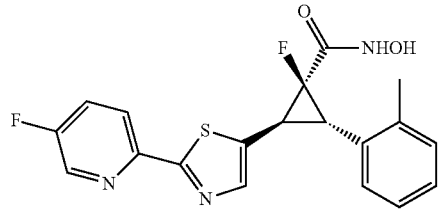

(1S,2R,3S)-1-fluoro-2-(2-(5-fluoropyridin-2-yl)thiazol-5-yl)-N-hydroxy-3-o-tolylcyclopropanecarboxamide or a pharmaceutically acceptable salt thereof.

Methods for obtaining the compounds, or pharmaceutically acceptable salts thereof, described herein will be apparent to those of ordinary skill in the art, suitable procedures being described, for example, in examples below, and in the references cited herein.

Also provided is a method for inhibiting at least one histone deacetylase. In some embodiments, the at least one histone deacetylase is a class IIa HDAC. In some embodiments, the at least one histone deacetylase is selected from HDAC-4, HDAC-5, HDAC-7, and HDAC-9. In some embodiments, the inhibition is in a cell. In some embodiments, the compound, or pharmaceutically acceptable salt thereof, described herein is selective for inhibiting at least one class II histone deacetylase. In some embodiments, the compound, or pharmaceutically acceptable salt thereof, described herein is a selective inhibitor of HDAC-4 and/or HDAC-5.

Also provided is a method of treating a condition or disorder mediated by HDAC in a subject in need of such a treatment, comprising administering to the subject a therapeutically effective amount of at least one compound, or pharmaceutically acceptable salt thereof, described herein.

In some embodiments, the condition or disorder mediated by HDAC comprises a neurodegenerative pathology. Accordingly, also provided is a method of treating a neurodegenerative pathology mediated by HDAC in a subject in need of such a treatment, comprising administering to the subject a therapeutically effective amount of at least one compound, or pharmaceutically acceptable salt thereof, described herein.

In some embodiments, the neurodegenerative pathology is chosen from Alzheimer's disease, Parkinson's disease, neuronal intranuclear inclusion disease (NIID), Dentatorubral pallidoluysian atrophy (DRPLA), Friedreich's ataxia, Rubenstein-Taubi Syndrome, and polyglutamine diseases such as Huntington's disease; spinocerebellar ataxia 1 (SCA 1), spinocerebellar ataxia 7 (SCA 7), seizures, striatonigral degeneration, progressive supranuclear palsy, torsion dystonia, spasmodic torticollis, dyskinesis, familial tremor, Gilles de la Tourette syndrome, diffuse Lewy body disease, progressive supranuclear palsy, Pick's disease, primary lateral sclerosis, progressive neural muscular atrophy, spinal muscular atrophy, hypertrophic interstitial polyneuropathy, retinitis pigmentosa, hereditary optic atrophy, hereditary spastic paraplegia, Shy-Drager syndrome, Kennedy's disease, protein-aggregation-related neurodegeneration, Machado-Joseph's disease, spongiform encephalopathy, prion-related disease, multiple sclerosis (MS), progressive supranuclear palsy (Steel-Richardson-Olszewski disease), Hallervorden-Spatz disease, progressive familial myoclonic epilepsy, cerebellar degeneration, motor neuron disease, Werdnig-Hoffman disease, Wohlfart-Kugelberg-Welander disease, Charcot-Marie-Tooth disease, Dejerine-Sottas disease, Leber's disease, progressive systemic sclerosis, dermatomyositis, and mixed connective tissue disease.

In some embodiments, the neurodegenerative pathology is an acute or chronic degenerative disease of the eye. Acute or chronic degenerative diseases of the eye include glaucoma, dry age-related macular degeneration, retinitis pigmentosa and other forms of heredodegenerative retinal disease, retinal detachment, macular pucker, ischemia affecting the outer retina, cellular damage associated with diabetic retinopathy and retinal ischemia, damage associated with laser therapy, ocular neovascular, diabetic retinopathy, rubeosis iritis, uveitis, Fuch's heterochromatic iridocyclitis, neovascular glaucoma, corneal neovascularization, retinal ischemia, choroidal vascular insufficiency, choroidal thrombosis, carotid artery ischemia, contusive ocular injury, retinopathy of permaturity, retinal vein occlusion, proliferative vitreoretinopathy, corneal angiogenesis, retinal microvasculopathy, and retinal edema.

In some embodiments, the condition or disorder mediated by HDAC comprises a fibrotic disease such as liver fibrosis, cystic fibrosis, cirrhosis, and fibrotic skin diseases, e.g., hypertrophic scars, keloid, and Dupuytren's contracture. Accordingly, also provided is a method of treating a fibrotic disease mediated by HDAC in a subject in need of such a treatment, comprising administering to the subject a therapeutically effective amount of at least one compound, or pharmaceutically acceptable salt thereof, described herein.

In some embodiments, the condition or disorder mediated by HDAC comprises a psychological disorder, such as depression, bipolar disease and dementia. In some embodiments, the condition or disorder mediated by HDAC comprises depression. Accordingly, also provided is a method of treating a psychological disorder, such as depression, mediated by HDAC in a subject in need of such a treatment, comprising administering to the subject a therapeutically effective amount of at least one compound, or pharmaceutically acceptable salt thereof, described herein. In some embodiments, the depression is chosen from major depressive disorder, and bipolar disorder.

In some embodiments, the condition or disorder mediated by HDAC comprises anxiety. Accordingly, also provided is a method of treating an anxiety mediated by HDAC in a subject in need of such a treatment, comprising administering to the subject a therapeutically effective amount of at least one compound, or pharmaceutically acceptable salt thereof, described herein.

In some embodiments, the condition or disorder mediated by HDAC comprises schizophrenia. Accordingly, also provided is a method of treating a schizophrenia mediated by HDAC in a subject in need of such a treatment, comprising administering to the subject a therapeutically effective amount of at least one compound, or pharmaceutically acceptable salt thereof, described herein.

In some embodiments, the condition or disorder mediated by HDAC comprises a motor neuron disease, muscle atrophy/muscle wasting disorders, or amyotrophic lateral sclerosis (ALS). Accordingly, also provided is a method of treating a motor neuron disease, muscle atrophy/muscle wasting disorders, or amyotrophic lateral sclerosis (ALS) mediated by HDAC in a subject in need of such a treatment, comprising administering to the subject a therapeutically effective amount of at least one compound, or pharmaceutically acceptable salt thereof, described herein.

In some embodiments, the condition or disorder mediated by HDAC comprises a cardiovascular condition. Accordingly, also provided is a method of treating a cardiovascular condition mediated by HDAC in a subject in need of such a treatment, comprising administering to the subject a therapeutically effective amount of at least one compound, or pharmaceutically acceptable salt thereof, described herein. In some embodiments, the cardiovascular condition is chosen from cardiomyopathy, cardiac hypertrophy, myocardial ischemia, heart failure, cardiac restenosis, and arteriosclerosis.

In some embodiments, the condition or disorder mediated by HDAC comprises cancer. Accordingly, also provided is a method of treating cancer mediated by HDAC in a subject in need of such a treatment, comprising administering to the subject a therapeutically effective amount of at least one compound, or pharmaceutically acceptable salt thereof, described herein. In some embodiments, the cancer is chosen from lymphoma, pancreatic cancer, colorectal cancer, hepatocellular carcinoma, Waldenstrom macroglobulinemia, hormone refractory cancer of the prostate, and leukaemia, breast cancer, lung cancer, ovarian cancer, prostate cancer, head and neck cancer, renal cancer, gastric cancer, brain cancer, B-cell lymphoma, peripheral T-cell lymphoma, and cutaneous T-cell lymphoma. In some further embodiments, the cancer is chosen from the following cancer types. Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor [nephroblastoma], lymphoma, leukemia), bladder and urethra (squamous cell carcinoma, transitional cell carcinoma, adenocarcinoma, prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma, cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma); Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; Skin: malignant melanoma, basal cell carcinoma, squamous cell carcinoma, Karposi's sarcoma, moles dysplastic nevi, lipoma, angioma, dermatofibroma, keloids, psoriasis; and Adrenal glands: neuroblastoma; and the sensitization of tumors to radiotherapy by administering the compound according to the invention before, during or after irradiation of the tumor for treating cancer.

In some embodiments, the condition or disorder mediated by HDAC comprises a condition or disorder treatable by immune modulation. Accordingly, also provided is a method of treating a condition or disorder treatable by immune modulation mediated by HDAC in a subject in need of such a treatment, comprising administering to the subject a therapeutically effective amount of at least one compound, or pharmaceutically acceptable salt thereof, described herein. In some embodiments, the condition or disorder treatable by immune modulation is chosen from asthma, irritable bowel syndrome, Crohn's disease, ulcerative colitis, bowel motility disorders, hypertension, rheumatoid arthritis, osteoarthritis, juvenile chronic arthritis, graft versus host disease, psoriasis, spondyloarthropathy, inflammatory bowel disease, alcoholic hepatitis, Sjogren's syndrome, ankylosing spondylitis, membranous glomerulopathy, discogenic pain, systemic lupus erythematosus, allergic bowel disease, coeliac disease, bronchitis, cystic fibrosis, rheumatoid spondylitis, osteoarthritis, uveitis, iritis, and conjunctivitis, ischemic bowel disease, psoriasis, eczema, dermatitis, septic arthritis, gout, pseudogout, juvenile arthritis, Still's disease, Henoch-Schonlein purpura, psoriatic arthritis, myalgia, reactive arthritis (Reiter's syndrome), hemochromatosis, Wegener's granulomatosis, familial Mediterranean fever (FMF), HBDS (hyperimmunoglobulinemia D and periodic fever syndrome), TRAPS (TNF-alpha receptor associated periodic fever syndrome), chronic obstructive pulmonary disease, neonatal-onset multisystem inflammatory disease (NOMID), cryopyrin-associated periodic syndrome (CAPS), and familial cold autoinflammatory syndrome (FCAS).

In some embodiments, the condition or disorder mediated by HDAC comprises an allergic disease. Accordingly, also provided is a method of treating an allergic disease, mediated by HDAC in a subject in need of such a treatment, comprising administering to the subject a therapeutically effective amount of at least one compound, or pharmaceutically acceptable salt thereof, described herein. Allergic diseases include, but are not limited to, respiratory allergic diseases such as allergic rhinitis, hypersensitivity lung diseases, hypersensitivity pneumonitis, eosinophilic pneumonias, Loeffler's syndrome, chronic eosinophilic pneumonia, delayed-type hypersensitivity, interstitial lung diseases (ILD), idiopathic pulmonary fibrosis, polymyositis, dermatomyositis, systemic anaphylaxis, drug allergies (e.g., to penicillin or cephalosporins), and insect sting allergies.

In some embodiments, the condition or disorder mediated by HDAC comprises an infectious disease such as a fungal infection, bacterial infection, viral infection, and protozoal infection, e.g., malaria, giardiasis, leishmaniasis, Chaga's disease, dysentery, toxoplasmosis, and coccidiosis. In some embodiments, the condition or disorder mediated by HDAC comprises malaria. Accordingly, also provided is a method of treating an infectious disease, such as malaria, mediated by HDAC in a subject in need of such a treatment, comprising administering to the subject a therapeutically effective amount of at least one compound, or pharmaceutically acceptable salt thereof, described herein.

In some embodiments, the condition or disorder mediated by HDAC comprises autism or Rett syndrome. Accordingly, also provided is a method of treating autism or Rett syndrome mediated by HDAC in a subject in need of such a treatment, comprising administering to the subject a therapeutically effective amount of at least one compound, or pharmaceutically acceptable salt thereof, described herein.

In some embodiments, the condition or disorder mediated by HDAC comprises a hematological disorder such as thalassemia, anemia, and sickle cell anemia. Accordingly, also provided is a method of treating a hematological disorder mediated by HDAC in a subject in need of such a treatment, comprising administering to the subject a therapeutically effective amount of at least one compound, or pharmaceutically acceptable salt thereof, described herein.

In some embodiments, the condition or disorder mediated by HDAC comprises a metabolic disease such as prediabetes or diabetes (type I or II). Accordingly, also provided is a method of treating a metabolic disease, such as prediabetes or diabetes (type I or II), mediated by HDAC in a subject in need of such a treatment, comprising administering to the subject a therapeutically effective amount of at least one compound, or pharmaceutically acceptable salt thereof, described herein.

In some embodiments, the condition or disorder mediated by HDAC comprises a disorder that may also be treated by progenitor/stem cell based therapies such as: disorders related to diabetes (organ failure, cirrhosis, and hepatitis); central nervous system (CNS) disorders associated with dysregulation of progenitor cells in the brain (e.g., post-traumatic stress disorder (PTSD); tumors (e.g., retinoblastomas); disorders affecting oligodendrycoyte progenitor cells (e.g., astrocytomas and ependimal cell tumors); multiple sclerosis; demyelinating disorders such as the leukodystrophies; neuropathies associated with white matter loss; and cerebellar disorders such as ataxia; and olfactory progenitor disorders (e.g., anosmic conditions). Accordingly, also provided is a method of treating a disorder that is mediated by HDAC in a subject in need of such a treatment, comprising administering to the subject a therapeutically effective amount of at least one compound, or pharmaceutically acceptable salt thereof, described herein, either before, during, or after a treatment with progenitor/stem cell based therapies.

In some embodiments, the condition or disorder mediated by HDAC comprises a disorder related to the proliferation of epithelial and mesenchymal cells (e.g., tumors, wound healing, and surgeries). Accordingly, also provided is a method of treating a disorder related to the proliferation of epithelial and mesenchymal cells that is mediated by HDAC in a subject in need of such a treatment, comprising administering to the subject a therapeutically effective amount of at least one compound, or pharmaceutically acceptable salt thereof, described herein.

In some embodiments, the condition or disorder mediated by HDAC comprises a disorder related to the proliferation of bone progenitors (e.g., osteoblasts and osteoclasts), disorders related to hair and epidermal progenitors (e.g., hair loss, cutaneous tumors, skin regeneration, burns, and cosmetic surgery); and disorders related to bone loss during menopause. Accordingly, also provided is a method of treating disorders related to the proliferation of bone progenitors, disorders related to hair and epidermal progenitors, or disorders related to bone loss that are mediated by HDAC in a subject in need of such a treatment, comprising administering to the subject a therapeutically effective amount of at least one compound, or pharmaceutically acceptable salt thereof, described herein.

In some embodiments, the condition or disorder mediated by HDAC is a viral disorder for which blood cells become sensitized to other treatments after HDAC inhibition, following administering to the subject a therapeutically effective amount of at least one compound, or pharmaceutically acceptable salt thereof, as described herein.

In some embodiments, the condition or disorder mediated by HDAC is an immune disorder that may be co-treated with TNFα or other immune modulators, upon administering to the subject a therapeutically effective amount of at least one compound, or pharmaceutically acceptable salt thereof, as described herein.

In some embodiments, the condition or disorder mediated by HDAC comprises a graft rejection or transplant rejection. Accordingly, also provided is a method of treating a disorder related to a graft rejection or a transplant rejection that is mediated by HDAC in a subject in need of such a treatment, comprising administering to the subject a therapeutically effective amount of at least one compound, or pharmaceutically acceptable salt thereof, described herein.

In some embodiments, the condition or disorder mediated by HDAC comprises a blood pressure disorder related to nitric oxide (NO) regulation (e.g., hypertension, erectile dysfunction, asthma; and ocular disorders as glaucoma). Accordingly, also provided is a method of treating a blood pressure disorder related to nitric oxide (NO) regulation that is mediated by HDAC in a subject in need of such a treatment, comprising administering to the subject a therapeutically effective amount of at least one compound, or pharmaceutically acceptable salt thereof, described herein.

In some embodiments, the condition or disorder is a cardiac hypertrophic disorder. Accordingly, also provided is a method of treating a cardiac hypertrophic disorder that is mediated by HDAC in a subject in need of such a treatment, comprising administering to the subject a therapeutically effective amount of at least one compound, or pharmaceutically acceptable salt thereof, described herein.

Also provided are methods of treatment in which at least one compound, or pharmaceutically acceptable salt thereof, described herein is the only active agent given to the subject and also includes methods of treatment in which at least one compound, or pharmaceutically acceptable salt thereof, described herein is given to the subject in combination with one or more additional active agents.

In general, the compounds, or pharmaceutically acceptable salts thereof, described herein will be administered in a therapeutically effective amount by any of the accepted modes of administration for agents that serve similar utilities. The actual amount of the compound, i.e., the active ingredient, will depend upon numerous factors such as the severity of the disease to be treated, the age and relative health of the subject, the potency of the compound used, the route and form of administration, and other factors well known to the skilled artisan. The drug can be administered at least once a day, such as once or twice a day.

In some embodiments, the compounds, or pharmaceutically acceptable salts thereof, described herein are administered as a pharmaceutical composition. Accordingly, provided are pharmaceutical compositions comprising at least one compound, or pharmaceutically acceptable salt thereof, described herein, together with at least one pharmaceutically acceptable vehicle chosen from carriers, adjuvants, and excipients.

Pharmaceutically acceptable vehicles must be of sufficiently high purity and sufficiently low toxicity to render them suitable for administration to the animal being treated. The vehicle can be inert or it can possess pharmaceutical benefits. The amount of vehicle employed in conjunction with the compound, or pharmaceutically acceptable salt thereof, is sufficient to provide a practical quantity of material for administration per unit dose of the compound, or pharmaceutically acceptable salt thereof.

Exemplary pharmaceutically acceptable carriers or components thereof are sugars, such as lactose, glucose and sucrose; starches, such as corn starch and potato starch; cellulose and its derivatives, such as sodium carboxymethyl cellulose, ethyl cellulose, and methyl cellulose; powdered tragacanth; malt; gelatin; talc; solid lubricants, such as stearic acid and magnesium stearate; calcium sulfate; synthetic oils; vegetable oils, such as peanut oil, cottonseed oil, sesame oil, olive oil, and corn oil; polyols such as propylene glycol, glycerine, sorbitol, mannitol, and polyethylene glycol; alginic acid; phosphate buffer solutions; emulsifiers, such as the TWEENS; wetting agents, such sodium lauryl sulfate; coloring agents; flavoring agents; tableting agents; stabilizers; antioxidants; preservatives; pyrogen-free water; isotonic saline; and phosphate buffer solutions.

Optional active agents may be included in a pharmaceutical composition, which do not substantially interfere with the activity of the compound, or pharmaceutically acceptable salt thereof, described herein.

Effective concentrations of at least one compound, or pharmaceutically acceptable salt thereof, described herein are mixed with a suitable pharmaceutically acceptable vehicle. In instances in which the compound, or pharmaceutically acceptable salt thereof, exhibits insufficient solubility, methods for solubilizing compounds may be used.

Such methods are known to those of skill in this art, and include, but are not limited to, using cosolvents, such as dimethylsulfoxide (DMSO), using surfactants, such as TWEEN, or dissolution in aqueous sodium bicarbonate.

Upon mixing or addition of a compound, or pharmaceutically acceptable salt thereof, described herein, the resulting mixture may be a solution, suspension, emulsion or the like. The form of the resulting mixture depends upon a number of factors, including the intended mode of administration and the solubility of the compound, or pharmaceutically acceptable salt thereof, in the chosen vehicle. The effective concentration sufficient for ameliorating the symptoms of the disease treated may be empirically determined.

The compounds, or pharmaceutically acceptable salts thereof, described herein may be administered orally, topically, parenterally, intravenously, by intramuscular injection, by inhalation or spray, sublingually, transdermally, via buccal administration, rectally, as an ophthalmic solution, or by other means, in dosage unit formulations.

Pharmaceutical compositions may be formulated for oral use, such as for example, tablets, troches, lozenges, aqueous or oily suspensions, dispersible powders or granules, emulsions, hard or soft capsules, or syrups or elixirs. Pharmaceutical compositions intended for oral use may be prepared according to any method known to the art for the manufacture of pharmaceutical compositions and such compositions may contain one or more agents, such as sweetening agents, flavoring agents, coloring agents and preserving agents, in order to provide pharmaceutically elegant and palatable preparations. In some embodiments, oral pharmaceutical compositions contain from 0.1 to 99% of at least one compound, or pharmaceutically acceptable salt thereof, described herein. In some embodiments, oral pharmaceutical compositions contain at least 5% (weight %) of at least one compound, or pharmaceutically acceptable salt thereof, described herein. Some embodiments contain from 25% to 50% or from 5% to 75% of at least one compound, or pharmaceutically acceptable salt thereof, described herein.

Orally administered pharmaceutical compositions also include liquid solutions, emulsions, suspensions, powders, granules, elixirs, tinctures, syrups, and the like. The pharmaceutically acceptable carriers suitable for preparation of such compositions are well known in the art. Oral pharmaceutical compositions may contain preservatives, flavoring agents, sweetening agents, such as sucrose or saccharin, taste-masking agents, and coloring agents.

Typical components of carriers for syrups, elixirs, emulsions and suspensions include ethanol, glycerol, propylene glycol, polyethylene glycol, liquid sucrose, sorbitol and water. Syrups and elixirs may be formulated with sweetening agents, for example glycerol, propylene glycol, sorbitol or sucrose. Such pharmaceutical compositions may also contain a demulcent.

The compound, or pharmaceutically acceptable salt thereof, described herein can be incorporated into oral liquid preparations such as aqueous or oily suspensions, solutions, emulsions, syrups, or elixirs, for example. Moreover, pharmaceutical compositions containing these at least one compound, or pharmaceutically acceptable salt thereof, can be presented as a dry product for constitution with water or other suitable vehicle before use. Such liquid preparations can contain conventional additives, such as suspending agents (e.g., sorbitol syrup, methyl cellulose, glucose/sugar, syrup, gelatin, hydroxyethyl cellulose, carboxymethyl cellulose, aluminum stearate gel, and hydrogenated edible fats), emulsifying agents (e.g., lecithin, sorbitan monsoleate, or acacia), non-aqueous vehicles, which can include edible oils (e.g., almond oil, fractionated coconut oil, silyl esters, propylene glycol and ethyl alcohol), and preservatives (e.g., methyl or propyl p-hydroxybenzoate and sorbic acid).

For a suspension, typical suspending agents include methylcellulose, sodium carboxymethyl cellulose, AVICEL RC-591, tragacanth and sodium alginate; typical wetting agents include lecithin and polysorbate 80; and typical preservatives include methyl paraben and sodium benzoate.

Aqueous suspensions contain the active material(s) in admixture with excipients suitable for the manufacture of aqueous suspensions. Such excipients are suspending agents, for example sodium carboxymethylcellulose, methylcellulose, hydropropylmethylcellulose, sodium alginate, polyvinylpyrrolidone, gum tragacanth and gum acacia; dispersing or wetting agents; may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol substitute, or condensation products of ethylene oxide with partial esters derived from fatty acids and hexitol anhydrides, for example polyethylene sorbitan substitute. The aqueous suspensions may also contain one or more preservatives, for example ethyl, or n-propyl p-hydroxybenzoate.

Oily suspensions may be formulated by suspending the active ingredients in a vegetable oil, for example peanut oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These pharmaceutical compositions may be preserved by the addition of an anti-oxidant such as ascorbic acid.

Pharmaceutical compositions may also be in the form of oil-in-water emulsions. The oily phase may be a vegetable oil, for example olive oil or peanut oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monoleate, and condensation products of the said partial esters with ethylene oxide, for example polyoxyethylene sorbitan monoleate.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above.

Tablets typically comprise conventional pharmaceutically acceptable adjuvants as inert diluents, such as calcium carbonate, sodium carbonate, mannitol, lactose and cellulose; binders such as starch, gelatin and sucrose; disintegrants such as starch, alginic acid and croscarmellose; lubricants such as magnesium stearate, stearic acid and talc. Glidants such as silicon dioxide can be used to improve flow characteristics of the powder mixture. Coloring agents, such as the FD&C dyes, can be added for appearance. Sweeteners and flavoring agents, such as aspartame, saccharin, menthol, peppermint, and fruit flavors, can be useful adjuvants for chewable tablets. Capsules (including time release and sustained release formulations) typically comprise one or more solid diluents disclosed above. The selection of carrier components often depends on secondary considerations like taste, cost, and shelf stability.

Such pharmaceutical compositions may also be coated by conventional methods, typically with pH or time-dependent coatings, such that the compound, or pharmaceutically acceptable salt thereof, is released in the gastrointestinal tract in the vicinity of the desired topical application, or at various times to extend the desired action. Such dosage forms typically include, but are not limited to, one or more of cellulose acetate phthalate, polyvinylacetate phthalate, hydroxypropyl methylcellulose phthalate, ethyl cellulose, Eudragit coatings, waxes and shellac.

Pharmaceutical compositions for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Pharmaceutical compositions may be in the form of a sterile injectable aqueous or oleaginous suspension. This suspension may be formulated according to the known art using those suitable dispersing or wetting agents and suspending agents that have been mentioned above. The sterile injectable preparation may also be sterile injectable solution or suspension in a non-toxic parentally acceptable vehicle, for example as a solution in 1,3-butanediol. Among the acceptable vehicles that may be employed are water, Ringers solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid can be useful in the preparation of injectables.

The compound, or pharmaceutically acceptable salt thereof, described herein may be administered parenterally in a sterile medium. Parenteral administration includes subcutaneous injections, intravenous, intramuscular, intrathecal injection or infusion techniques. The compound, or pharmaceutically acceptable salt thereof, described herein, depending on the vehicle and concentration used, can either be suspended or dissolved in the vehicle. Advantageously, adjuvants such as local anesthetics, preservatives and buffering agents can be dissolved in the vehicle. In many pharmaceutical compositions for parenteral administration the carrier comprises at least 90% by weight of the total composition. In some embodiments, the carrier for parenteral administration is chosen from propylene glycol, ethyl oleate, pyrrolidone, ethanol, and sesame oil.

The compound, or pharmaceutically acceptable salt thereof, described herein may also be administered in the form of suppositories for rectal administration of the drug. These pharmaceutical compositions can be prepared by mixing the drug with a suitable non-irritating excipient that is solid at ordinary temperatures but liquid at rectal temperature and will therefore melt in the rectum to release the drug. Such materials include cocoa butter and polyethylene glycols.

The compound, or pharmaceutically acceptable salt thereof, described herein may be formulated for local or topical application, such as for topical application to the skin and mucous membranes, such as in the eye, in the form of gels, creams, and lotions and for application to the eye.

Topical pharmaceutical compositions may be in any form including, for example, solutions, creams, ointments, gels, lotions, milks, cleansers, moisturizers, sprays, skin patches, and the like.

Such solutions may be formulated as 0.01%-10% isotonic solutions, pH 5-7, with appropriate salts. The compound, or pharmaceutically acceptable salt thereof, described herein may also be formulated for transdermal administration as a transdermal patch.

Topical pharmaceutical compositions comprising at least one compound, or pharmaceutically acceptable salt thereof, described herein can be admixed with a variety of carrier materials well known in the art, such as, for example, water, alcohols, aloe vera gel, allantoin, glycerine, vitamin A and E oils, mineral oil, propylene glycol, PPG-2 myristyl propionate, and the like.

Other materials suitable for use in topical carriers include, for example, emollients, solvents, humectants, thickeners and powders. Examples of each of these types of materials, which can be used singly or as mixtures of one or more materials, are as follows.

Representative emollients include stearyl alcohol, glyceryl monoricinoleate, glyceryl monostearate, propane-1,2-diol, butane-1,3-diol, mink oil, cetyl alcohol, iso-propyl isostearate, stearic acid, iso-butyl palmitate, isocetyl stearate, oleyl alcohol, isopropyl laurate, hexyl laurate, decyl oleate, octadecan-2-ol, isocetyl alcohol, cetyl palmitate, dimethylpolysiloxane, di-n-butyl sebacate, iso-propyl myristate, iso-propyl palmitate, iso-propyl stearate, butyl stearate, polyethylene glycol, triethylene glycol, lanolin, sesame oil, coconut oil, arachis oil, castor oil, acetylated lanolin alcohols, petroleum, mineral oil, butyl myristate, isostearic acid, palmitic acid, isopropyl linoleate, lauryl lactate, myristyl lactate, decyl oleate, and myristyl myristate; propellants, such as propane, butane, iso-butane, dimethyl ether, carbon dioxide, and nitrous oxide; solvents, such as ethyl alcohol, methylene chloride, iso-propanol, castor oil, ethylene glycol monoethyl ether, diethylene glycol monobutyl ether, diethylene glycol monoethyl ether, dimethyl sulphoxide, dimethyl formamide, tetrahydrofuran; humectants, such as glycerin, sorbitol, sodium 2-pyrrolidone-5-carboxylate, soluble collagen, dibutyl phthalate, and gelatin; and powders, such as chalk, talc, fullers earth, kaolin, starch, gums, colloidal silicon dioxide, sodium polyacrylate, tetra alkyl ammonium smectites, trialkyl aryl ammonium smectites, chemically modified magnesium aluminium silicate, organically modified montmorillonite clay, hydrated aluminium silicate, fumed silica, carboxyvinyl polymer, sodium carboxymethyl cellulose, and ethylene glycol monostearate.

The compound, or pharmaceutically acceptable salt thereof, described herein may also be topically administered in the form of liposome delivery systems, such as small unilamellar vesicles, large unilamellar vesicles, and multilamellar vesicles. Liposomes can be formed from a variety of phospholipids, such as cholesterol, stearylamine or phosphatidylcholines.

Other pharmaceutical compositions useful for attaining systemic delivery of the compound, or pharmaceutically acceptable salt thereof, include sublingual, buccal and nasal dosage forms. Such pharmaceutical compositions typically comprise one or more of soluble filler substances such as sucrose, sorbitol and mannitol, and binders such as acacia, microcrystalline cellulose, carboxymethyl cellulose, and hydroxypropyl methylcellulose. Glidants, lubricants, sweeteners, colorants, antioxidants and flavoring agents disclosed above may also be included.

Pharmaceutical compositions for inhalation typically can be provided in the form of a solution, suspension or emulsion that can be administered as a dry powder or in the form of an aerosol using a conventional propellant (e.g., dichlorodifluoromethane or trichlorofluoromethane).

The pharmaceutical compositions may also optionally comprise an activity enhancer. The activity enhancer can be chosen from a wide variety of molecules that function in different ways to enhance or be independent of therapeutic effects of the compound, or pharmaceutically acceptable salt thereof, described herein. Particular classes of activity enhancers include skin penetration enhancers and absorption enhancers.

Pharmaceutical compositions may also contain additional active agents that can be chosen from a wide variety of molecules, which can function in different ways to enhance the therapeutic effects of at least one compound, or pharmaceutically acceptable salt thereof, described herein. These optional other active agents, when present, are typically employed in the pharmaceutical compositions at a level ranging from 0.01% to 15%. Some embodiments contain from 0.1% to 10% by weight of the composition. Other embodiments contain from 0.5% to 5% by weight of the composition.

Also provided are packaged pharmaceutical compositions. Such packaged compositions include a pharmaceutical composition comprising at least one compound, or pharmaceutically acceptable salt thereof, described herein, and instructions for using the composition to treat a subject (typically a human patient). In some embodiments, the instructions are for using the pharmaceutical composition to treat a subject suffering a condition or disorder mediated by HDAC. The packaged pharmaceutical composition can include providing prescribing information; for example, to a patient or health care provider, or as a label in a packaged pharmaceutical composition. Prescribing information may include for example efficacy, dosage and administration, contraindication and adverse reaction information pertaining to the pharmaceutical composition.

In all of the foregoing the compound, or pharmaceutically acceptable salt thereof, can be administered alone, as mixtures, or in combination with other active agents.

The methods described herein include methods for treating Huntington's disease, including treating memory and/or cognitive impairment associated with Huntington's disease, comprising administering to a subject, simultaneously or sequentially, at least one compound, or pharmaceutically acceptable salt thereof, described herein and one or more additional agents used in the treatment of Huntington's disease such as, but not limited to, Amitriptyline, Imipramine, Despiramine, Nortriptyline, Paroxetine, Fluoxetine, Setraline, Terabenazine, Haloperidol, Chloropromazine, Thioridazine, Sulpride, Quetiapine, Clozapine, and Risperidone. In methods using simultaneous administration, the agents can be present in a combined composition or can be administered separately. As a result, also provided are pharmaceutical compositions comprising at least one compound, or pharmaceutically acceptable salt thereof, described herein and one or more additional pharmaceutical agents used in the treatment of Huntington's disease such as, but not limited to, Amitriptyline, Imipramine, Despiramine, Nortriptyline, Paroxetine, Fluoxetine, Setraline, Terabenazine, Haloperidol, Chloropromazine, Thioridazine, Sulpride, Quetiapine, Clozapine, and Risperidone. Similarly, also provided are packaged pharmaceutical compositions containing a pharmaceutical composition comprising at least one compound, or pharmaceutically acceptable salt thereof, described herein, and another composition comprising one or more additional pharmaceutical agents used in the treatment of Huntington's disease such as, but not limited to, Amitriptyline, Imipramine, Despiramine, Nortriptyline, Paroxetine, Fluoxetine, Setraline, Terabenazine, Haloperidol, Chloropromazine, Thioridazine, Sulpride, Quetiapine, Clozapine, and Risperidone.

Also provided are methods for Alzheimer's disease, including treating memory and/or cognitive impairment associated with Alzheimer's disease, comprising administering to a subject, simultaneously or sequentially, at least one compound, or pharmaceutically acceptable salt thereof, described herein and one or more additional agents used in the treatment of Alzheimer's disease such as, but not limited to, Reminyl, Cognex, Aricept, Exelon, Akatinol, Neotropin, Eldepryl, Estrogen and Clioquinol. In methods using simultaneous administration, the agents can be present in a combined composition or can be administered separately. Also provided are pharmaceutical compositions comprising at least one compound, or pharmaceutically acceptable salt thereof, described herein, and one or more additional pharmaceutical agents used in the treatment of Alzheimer's disease such as, but not limited to, Reminyl, Cognex, Aricept, Exelon, Akatinol, Neotropin, Eldepryl, Estrogen and Clioquinol. Similarly, also provided are packaged pharmaceutical compositions containing a pharmaceutical composition comprising at least one compound, or pharmaceutically acceptable salt thereof, described herein, and another composition comprising one or more additional pharmaceutical agents used in the treatment of Alzheimer's disease such as, but not limited to Reminyl, Cognex, Aricept, Exelon, Akatinol, Neotropin, Eldepryl, Estrogen and Clioquinol.

Also provided are methods for treating cancer comprising administering to a subject, simultaneously or sequentially, at least one compound, or pharmaceutically acceptable salt thereof, described herein and one or more additional agents used in the treatment of cancer such as, but not limited to, the following categories of anti-tumor agents:

(i) other cell cycle inhibitory agents that work by the same or different mechanisms from those defined hereinbefore, for example cyclin dependent kinase (CDK) inhibitors, in particular CDK2 inhibitors;

(ii) cytostatic agents such as antioestrogens (for example tamoxifen, toremifene, raloxifene, droloxifene, iodoxyfene), progestogens (for example megestrol acetate), aromatase inhibitors (for example anastrozole, letrazole, vorazole, exemestane), antiprogestogens, antiandrogens (for example flutamide, nilutamide, bicalutamide, cyproterone acetate), LHRH agonists and antagonists (for example goserelin acetate, luprolide), inhibitors of testosterone 5α-dihydroreductase (for example finasteride), anti-invasion agents (for example metalloproteinase inhibitors like marimastat and inhibitors of urokinase plasminogen activator receptor function) and inhibitors of growth factor function, (such growth factors include for example vascular endothelial growth factor, epithelial growth factor, platelet derived growth factor and hepatocyte growth factor such inhibitors include growth factor antibodies, growth factor receptor antibodies, tyrosine kinase inhibitors and serine/threonine kinase inhibitors);

(iii) antiproliferative/antineoplastic drugs and combinations thereof, as used in medical oncology, such as antimetabolites (for example antifolates like methotrexate, fluoropyrimidines like 5-fluorouracil, purine and adenosine analogues, cytosine arabinoside); antitumour antibiotics (for example anthracyclines like doxorubicin, daunomycin, epirubicin and idarubicin, mitomycin-C, dactinomycin, mithramycin); platinum derivatives (for example cisplatin, carboplatin); alkylating agents (for example nitrogen mustard, melphalan, chlorambucil, busulphan, cyclophosphamide, ifosfamide, nitrosoureas, thiotepa); antimitotic agents (for example vinca alkaloids like vincrisitine and taxoids like taxol, taxotere); topoisomerase inhibitors (for example epipodophyllotoxins like etoposide and teniposide, amsacrine, topotecan);

(iv) antiangiogenic agents that work by different mechanisms from those defined hereinbefore (for example receptor tyrosine kinases like Tie-2, inhibitors of integrin alpha v beta 3 function, angiostatin, razoxin, thalidomide), and including vascular targeting agents; and (v) differentiation agents (for example retinoic acid and vitamin D).

In methods using simultaneous administration, the agents can be present in a combined composition or can be administered separately. Also provided are pharmaceutical compositions comprising at least one compound, or pharmaceutically acceptable salt thereof, described herein, and one or more anti-tumor agent as described herein. Similarly, also provided are packaged pharmaceutical compositions containing a pharmaceutical composition comprising at least one compound, or pharmaceutically acceptable salt thereof, described herein, and another composition comprising one or more one or more anti-tumor agent as described herein. When used in combination with one or more additional pharmaceutical agent or agents, the described herein may be administered prior to, concurrently with, or following administration of the additional pharmaceutical agent or agents.

In some embodiments, the compounds, or pharmaceutically acceptable salts thereof, described herein, are administered in conjunction with surgery or radiotherapy, optionally in combination with one or more additional agents used in the treatment of cancer.

The dosages of the compounds described herein depend upon a variety of factors including the particular syndrome to be treated, the severity of the symptoms, the route of administration, the frequency of the dosage interval, the particular compound utilized, the efficacy, toxicology profile, pharmacokinetic profile of the compound, and the presence of any deleterious side-effects, among other considerations.

The compound, or pharmaceutically acceptable salt thereof, described herein is typically administered at dosage levels and in a manner customary for HDAC inhibitors. For example, the compound, or pharmaceutically acceptable salt thereof, can be administered, in single or multiple doses, by oral administration at a dosage level of generally 0.001-100 mg/kg/day, for example, 0.01-100 mg/kg/day, such as 0.1-70 mg/kg/day, for example, 0.5-10 mg/kg/day. Unit dosage forms can contain generally 0.01-1000 mg of at least one compound, or pharmaceutically acceptable salt thereof, described herein, for example, 0.1-50 mg of at least one compound, or pharmaceutically acceptable salt thereof, described herein. For intravenous administration, the compounds can be administered, in single or multiple dosages, at a dosage level of, for example, 0.001-50 mg/kg/day, such as 0.001-10 mg/kg/day, for example, 0.01-1 mg/kg/day. Unit dosage forms can contain, for example, 0.1-10 mg of at least one compound, or pharmaceutically acceptable salt thereof, described herein.

A labeled form of a compound, or pharmaceutically acceptable salt thereof, described herein can be used as a diagnostic for identifying and/or obtaining compounds that have the function of modulating an activity of HDAC as described herein. The compound, or pharmaceutically acceptable salt thereof, described herein may additionally be used for validating, optimizing, and standardizing bioassays.

By "labeled" herein is meant that the compound is either directly or indirectly labeled with a label which provides a detectable signal, e.g., radioisotope, fluorescent tag, enzyme, antibodies, particles such as magnetic particles, chemiluminescent tag, or specific binding molecules, etc. Specific binding molecules include pairs, such as biotin and streptavidin, digoxin and antidigoxin etc. For the specific binding members, the complementary member would normally be labeled with a molecule which provides for detection, in accordance with known procedures, as outlined above. The label can directly or indirectly provide a detectable signal.

In carrying out the procedures of the methods described herein, it is of course to be understood that reference to particular buffers, media, reagents, cells, culture conditions and the like are not intended to be limiting, but are to be read so as to include all related materials that one of ordinary skill in the art would recognize as being of interest or value in the particular context in which that discussion is presented. For example, it is often possible to substitute one buffer system or culture medium for another and still achieve similar, if not identical, results. Those of skill in the art will have sufficient knowledge of such systems and methodologies so as to be able, without undue experimentation, to make such substitutions as will optimally serve their purposes in using the methods and procedures disclosed herein.

EXAMPLES

The compounds, or pharmaceutically acceptable salts thereof, compositions, and methods described herein are further illustrated by the following non-limiting examples.

As used herein, the following abbreviations have the following meanings. If an abbreviation is not defined, it has its generally accepted meaning.

Abbreviations

BOP: Benzotriazole-1-yl-oxy-tris-(dimethylamino)-phosphonium hexafluorophosphate
DABCO: 1,4-Diazabicyclo[2.2.2]octane
DCM: Dichloromethane
DMF: Dimethylformamide
DMSO: Dimethylsulfoxide
ES+: Electrospray Positive Ionisation
ES−: Electrospray Negative Ionisation
Et$_3$N: Triethylamine
Et$_2$O: Diethyl ether
EtOAc: Ethyl acetate
h: Hour
HPLC: High Performance Liquid Chromatography
i-hex: iso-Hexane
IPA: Isopropanol
LCMS: Liquid Chromatography Mass Spectrometry
LDA: Lithium diisopropylamide
LiHMDS: Lithium bis(trimethylsilyl)amide
M: Mass
MeCN: Acetonitrile
MeOH: Methanol
NFSI: N-Fluorobenzenesulfonimide
Pd(dppf)Cl$_2$: [1,1'-Bis(diphenylphosphino)ferrocene]dichloropalladium(II)
Pd(PPh$_3$)$_4$: Tetrakis(triphenylphosphine)palladium(O)
P(o-tol)$_3$: Tri(ortho-Tolyl)phosphine RT: Retention time
r.t.: Room temperature
THF: Tetrahydrofuran Analytical Conditions Compounds were named with the aid of the Cambridge-soft Chemistry Cartridge (v. 9.0.0.182) software.

All reactions involving air- or moisture-sensitive reagents were performed under a nitrogen atmosphere using dried solvents and glassware.

Racemic mixtures of the cyclopropyl core are denoted using asterisks e.g. (1R*,2R*,3R*). Chirally pure compounds are denoted without asterisks e.g. (1R,2R,3R).

| Analytical Condition | Method | Description | |
|---|---|---|---|
| 10cm_ESI_Formic_MeCN, 10cm_ESCI_Formic_MeCN | 1 | Solvents: | Acetonitrile (far UV grade) with 0.1% (v/v) formic acid. Water (high purity via PureLab Option unit) with 0.1% formic acid |
| | | Column: | Phenomenex Luna 5 μm C18 (2), 100 × 4.6 mm (Plus guard cartridge) |
| | | Flow Rate: | 2 mL/min |
| | | gradient: | A: Water/formic acid B: MeCN/formic acid |

| Time | A % | B % |
|---|---|---|
| 0.00 | 95 | 5 |
| 3.50 | 5 | 95 |
| 5.50 | 5 | 95 |
| 5.60 | 95 | 5 |
| 6.50 | 95 | 5 |

| Analytical Condition | Method | Description | |
|---|---|---|---|
| | | Typical Injections 2-7 μL (concentration ~0.2-1.0 mg/mL) | |
| 15cm_Bicarb_GeminiNX_HPLC_MeCN | 2 | Solvents: | 100% Acetonitrile (Far UV grade) Water (High purity via PureLab Ultra unit) with 10 mM Ammonium Bicarbonate |
| | | Column: | Phenomenex, Gemini NX, 3 μm C18, 150 × 4.6 mm. |
| | | Flow Rate: | 1 mL/min |
| | | gradient: | A: 10 mM Ammonium Bicarbonate in water B: 100% MeCN |

| Time | A % | B % |
|---|---|---|
| 0.00 | 95.5 | 4.5 |
| 3.00 | 95.5 | 4.4 |
| 9.00 | 0 | 100 |
| 13.6 | 0 | 100 |
| 13.7 | 95.5 | 4.5 |
| 15 | 95.5 | 4.5 |

| Analytical Condition | Method | Description | |
|---|---|---|---|
| | | Typical Injections 2-7 μL (concentration ~0.2-1 mg/mL) | |
| 15cm_Formic_Ascentis_HPLC_MeCN | 3 | Solvents: | Acetonitrile (Far UV grade) with 0.1% (V/V) formic acid Water (High purity via PureLab Ultra unit) with 0.1% formic acid |
| | | Column: | Supelco, Ascentis ® Express C18 or Hichrom Halo C18, 2.7 μm C18, 150 × 4.6 mm. |
| | | Flow Rate: | 1 mL/min |
| | | gradient: | A: Water/formic B: MeCN/formic |

| Time | A % | B % |
|---|---|---|
| 0.00 | 96 | 4 |
| 3.00 | 96 | 4 |
| 9.00 | 0 | 100 |
| 13.6 | 0 | 100 |
| 13.7 | 96 | 4 |
| 15 | 96 | 4 |

Typical Injections 2-7 μL (concentration ~0.2-1 mg/mL)

-continued

| Analytical Condition | Method | Description | | | |
|---|---|---|---|---|---|
| 10cm_ESCI_bicarb_MeCN | 4 | Solvents: | Acetonitrile (Far UV grade) Water (High purity via PureLab Option unit) with 10 mM ammonium bicarbonate (ammonium hydrogen carbonate) | | |
| | | Column: | Waters Xterra MS 5m C18, 100 × 4.6 mm. (Plus guard cartridge) | | |
| | | Flow Rate: | 2 mL/min | | |
| | | gradient: | A: Water/Bicarb B: MeCN | | |
| | | | Time | A % | B % |
| | | | 0.00 | 95 | 5 |
| | | | 0.50 | 95 | 5 |
| | | | 4.00 | 5 | 95 |
| | | | 5.50 | 5 | 95 |
| | | | 5.60 | 95 | 5 |
| | | | 6.50 | 95 | 5 |
| | | Typical Injections 2-7 μL (concentration ~0.2-1 mg/mL) | | | |
| 10cm_Formic_ACE-AR_HPLC_CH3CN | 5 | Solvents: | Acetonitrile (Far UV grade) with 0.1% (V/V) formic acid Water (High purity via PureLab Ultra unit) with 0.1% formic acid | | |
| | | Column: | Hichrom ACE 3 C18-AR mixed mode column 100 × 4.6 mm | | |
| | | Flow Rate: | 1 mL/min | | |
| | | gradient: | A: Water/formic B: MeCN/formic | | |
| | | | Time | A % | B % |
| | | | 0.00 | 98 | 2 |
| | | | 3.00 | 98 | 2 |
| | | | 12.00 | 0 | 100 |
| | | | 15.4 | 0 | 100 |
| | | | 15.5 | 98 | 2 |
| | | | 17 | 98 | 2 |
| | | Typical Injections 0.2-10 μL | | | |
| 10cm_Formic_ACE-AR_HPLC_CH3OH_Slow | 6 | Solvents: | Methanol (AR grade) with 0.1% (V/V) formic acid Water (High purity via PureLab Ultra unit) with 0.1% formic acid | | |
| | | Column: | Hichrom ACE 3 C18-AR mixed mode column 100 × 4.6 mm | | |
| | | Flow Rate: | 1 mL/min | | |
| | | gradient: | A: Water/formic B: MeOH/formic | | |
| | | | Time | A % | B % |
| | | | 0.00 | 98 | 2 |
| | | | 3.00 | 98 | 2 |
| | | | 12.00 | 0 | 100 |
| | | | 15.4 | 0 | 100 |
| | | | 15.5 | 98 | 2 |
| | | | 17 | 98 | 2 |
| | | Typical Injections 0.2-10 μL | | | |

Synthetic Section
General Methods
Method A (Cyclopropanation Reaction)

A mixture of sulfonium salt (8.92 mmol), the enoate (5.96 mmol) and 12-crown-4 (8.92 mmol) in DCM (20 mL) was cooled to −20° C. LiHMDS (8.92 mL) was then added dropwise. After complete addition, the mixture was warmed to r.t, stirred for 2 h and quenched with $H_2O$ (30 mL). The biphasic mixture was separated and the organic layers were washed with brine (2×30 mL), separated, dried ($MgSO_4$), filtered and concentrated.

Method B (Hydroxamic Acid Formation)

To a stirred solution of ester (0.30 mmol) in THF/MeOH (1:1, 3 mL) was added hydroxylamine (0.2 mL, 50% aqueous solution, 3.00 mmol) and potassium hydroxide (33 mg, 0.60 mmol). The mixture was stirred at r.t. for 2 h, neutralized with 1 M $HCl_{(aq)}$ and extracted with DCM. The combined organic layers were washed with brine (10 mL), passed through a phase separator and concentrated.

Method C (Heck Reaction)

A stirred mixture of aryl bromide (10.0 mmol), ethyl acrylate (15.0 mmol), palladium acetate (1.00 mmol), P(o-tol)$_3$ (2.00 mmol) and $Et_3N$ (20.0 mmol) in DMF (50 mL) was degassed with nitrogen for 15 min and heated to 80° C. for 3-18 h. The reaction mixture was cooled and diluted with water (100 mL) and extracted into DCM (3×50 mL). The combined organics were washed with water (5×100 mL) and brine (100 mL). The organic layers were passed through a phase separator and concentrated.

Method D (Wittig Reaction)

To a stirred solution of triethyl phosphonoacetate (24.4 mmol) in THF (30 mL) at 0° C. was added sodium hydride (24.4 mmol) portionwise. The mixture was stirred for 1 h before addition of aldehyde (12.2 mmol). The reaction mixture was allowed to warm to r.t. and stirred for 17 h, before quenching with water (50 mL) and extracting into EtOAc (2×50 mL). The organic layers were combined and washed with water (2×50 mL), dried ($MgSO_4$), filtered and concentrated.

Method E (Heck Reaction-2)

A stirred mixture of aryl bromide (10.0 mmol), ethyl acrylate (15.0 mmol), palladium acetate (1.00 mmol), P(o-tol)$_3$ (2.00 mmol) and $Et_3N$ (20.0 mmol) in MeCN (50 mL) was degassed with nitrogen for 15 min. and heated to 80° C. for 3-18 h. The reaction mixture was cooled and the MeCN removed in vacuo. The residue was partitioned between DCM and $H_2O$ and the organic layers were passed through a phase separator and concentrated.

Example 1

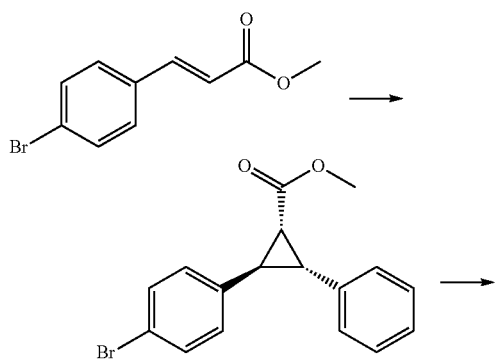

(1R*,2R*,3R*)-Methyl-2-(4-bromophenyl)-3-phenylcyclopropanecarboxylate

To a stirred solution of benzyl bromide (27 mL, 227 mmol) in acetone at r.t. was added tetrahydrothiophene (10.0 mL, 114 mmol). The solution was stirred for 16 h and the resulting precipitate filtered and washed with acetone (3×50 mL) and dried under air, to give 1-benzyltetrahydrothiophenium bromide as a white solid (51.9 g, 88%).

A mixture of 1-benzyltetrahydrothiophenium bromide (3.39 g, 13.1 mmol) and (E)-methyl 3-(4-bromophenyl) acrylate (2.10 g, 8.71 mmol) in DCM (50 mL) was cooled to −78° C. and slowly treated with LiHMDS (13.1 mL, 1 M solution in THF) (via syringe pump, 1 mL/h). After complete addition, the mixture was warmed to r.t., stirred for 16 h and was quenched with $H_2O$ (50 mL). The biphasic mixture was separated and the organic layer washed with brine (2×50 mL), dried ($MgSO_4$) and concentrated. Purification by flash silica column chromatography (gradient elution i-hex to 5% EtOAc in i-hex) gave the title compound as a colourless oil (600 mg, 20%). LCMS (ES+) 332, 334 (M+H)$^+$.

(1S*,2S*,3S*)-Methyl 2-(4-bromophenyl)-1-fluoro-3-phenylcyclopropanecarboxylate

To a solution of (1R*,2R*,3R*)-methyl-2-(4-bromophenyl)-3-phenylcyclopropanecarboxylate (662 mg, 2 mmol) and LiCl (500 mg, 12 mmol) in dry THF (50 mL) stirred at −78° C. for 20 min, was added LDA (2N, 3.3 mL, 6.6 mmol) and the reaction mixture was stirred at −78° C. for 30 min. Then a solution of NFSI (2.08 g, 6.6 mmol) in dry THF (20 mL) was added slowly and the reaction mixture was stirred for 2 h. The reaction was quenched with sat. $NH_4Cl$ (20 mL) and extracted with DCM (50 mL). The organic phase was passed through a phase separator and concentrated to afford a crude compound that was purified by flash silica column chromatography (gradient elution i-hex to 40% EtOAc in i-hex). The target compound was isolated (230 mg) as an enriched mixture (3:1) of the desired diastereoisomer. LCMS (ES+) 350 (M+H)$^+$.

(1S*,2S*,3S*)-(Bromophenyl)-1-fluoro-N-hydroxy-3-phenylcyclopropanecarboxamide

Following method B from (1S*,2S*,3S*)-methyl-2-(4-bromophenyl)-1-fluoro-3-phenylcyclopropanecarboxylate (100 mg, 0.29 mmol). Purification by flash silica column chromatography (gradient elution DCM to 5% MeOH in DCM) gave the racemic compound (22 mg, 22%). LCMS (ES−) 348, 350 (M−H)⁻, RT 3.88 min. (Analytical method 1); ¹H NMR δ (ppm)(DMSO-d₆): 11.17 (1H, s), 8.98 (1H, s), 7.63-7.60 (2H, m), 7.47-7.40 (2H, m), 7.38-7.25 (5H, m), 3.58 (2H, dd, J=19.1, 9.3 Hz), 3.54 (1H, s)

Example 2

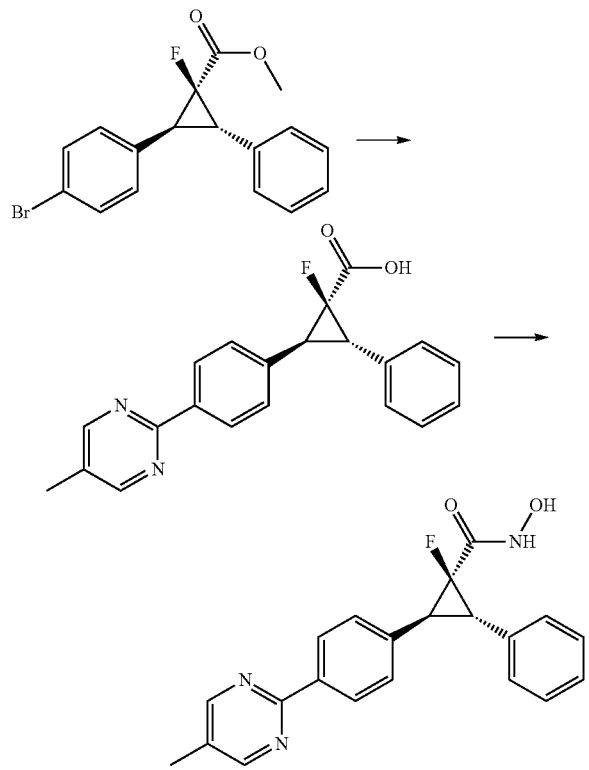

(1S*,2S*,3S*)-1-Fluoro-2-(4-(5-methylpyrimidin-2-yl)phenyl)-3-phenylcyclopropanecarboxylic acid A solution of (1S*,2S*,3S*)-methyl 2-(4-bromophenyl)-1-fluoro-3-phenylcyclopropanecarboxylate (226 mg, 0.65 mmol), bis-pinacolato diboron (165 mg, 0.65 mmol), Pd(dppf)₂Cl₂ (48 mg, 0.06 mmol), KOAc (279 mg, 2.8 mmol) in dioxane (7 mL) was stirred at 90° C. for 17 h. Water was added and the mixture was extracted with DCM and passed through a phase separator. The organic phase was concentrated and the crude used in the next step.

A solution of (1S*,2S*,3S*)-methyl-1-fluoro-2-phenyl-3-(4-(4,4,5,5-tetramethyl-1,3,2-dioxaborolan-2-yl)phenyl)cyclopropanecarboxylate (0.65 mmol), Pd(PPh₃)₄ (78 mg, 0.067 mmol), 5-methylpyrimidine bromide (137 mg, 0.79 mmol), 2N Na₂CO₃ (2.15 mL) in dioxane (5 mL) was stirred at 90° C. for 17 h. The reaction mixture was diluted with water and extracted into DCM. The organic phase was passed through a phase separator and concentrated. Purification by flash silica column chromatography (gradient elution i-hex to 40% EtOAc in i-hex) afforded the acid compound (145 mg, 63%). LCMS (ES+) 349 (M+H)⁺.

(1S,2S,3S)-1-Fluoro-N-hydroxy-2-(4-(5-methylpyrimidin-2-yl)phenyl)-3-phenylcyclopropanecarboxamide A solution of the (1S*,2S*,3S*)-1-fluoro-2-(4-(5-methylpyrimidin-2-yl)phenyl)-3-phenylcyclopropanecarboxylic acid (144 mg, 0.41 mmol), BOP (185 mg, 0.41 mmol), NH₂OH HCl (42 mg, 0.62 mmol), Et₃N (175 μL, 1.24 mmol) in pyridine (2.5 mL) was stirred at r.t. for 2 h. The solvent was evaporated and water was added. The mixture was extracted into DCM, passed through a phase separator and concentrated. Preparative achiral and chiral purification afforded the title compound (8.2 mg) (Chiralpak IC 30/70 [EtOH/MeOH (0.1% formic acid)]/heptane 1.0 mL/min, RT 16.3 min). LCMS (ES+) 364 (M+H)⁺ RT 3.69 min (Analytical method 1); ¹H NMR δ (ppm)(DMSO-d₆): 11.12 (1H, s), 8.93 (1H, s), 8.74 (2H, s), 8.35 (2H, d, J=8.2 Hz), 7.54 (2H, d, J=8.2 Hz), 7.38-7.26 (4H, m), 7.26-7.18 (1H, m), 3.62-3.52 (2H, m), 2.31 (3H, s).

(1R,2R,3R)-1-Fluoro-N-hydroxy-2-(4-(5-methylpyrimidin-2-yl)phenyl)-3-phenylcyclopropanecarboxamide (Chiralpak IC 30/70 [EtOH/MeOH (0.1% formic acid)]/heptane 1.0 mL/min, RT 13.6 min)

Example 3

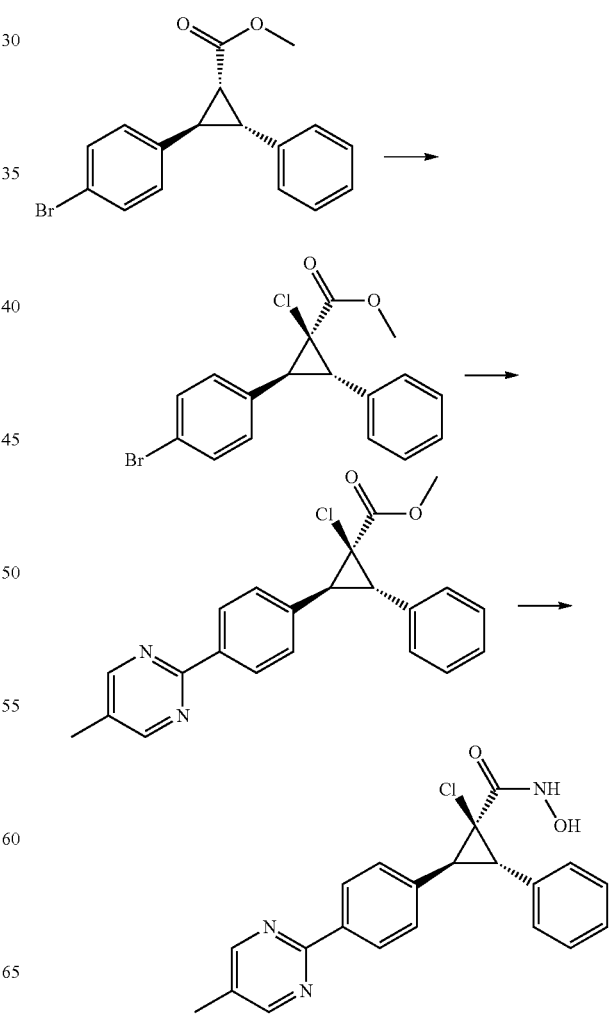

(1S*,2S*,3S*)-Methyl-2-(4-bromophenyl)-1-chloro-3-phenylcyclopropanecarboxylate To a solution of (1R*,2R*,3R*)-methyl-2-(4-bromophenyl)-3-phenylcyclopropanecarboxylate (1.72 g, 4 mmol) in dry THF (70 mL) stirred at −78° C. for 20 min, was added LDA (2 N, 7.5 mL, 15 mmol) and the reaction mixture was stirred at −78° C. for 30 min. Then CCl$_4$ (1.2 mL, 12 mmol) was added slowly and the reaction mixture was stirred for 2 h. The reaction was quenched with sat. NH$_4$Cl (40 mL) and extracted with DCM (100 mL). The organic phase was passed through a phase separator and concentrated to afford a crude compound that was purified by flash silica column chromatography (gradient elution i-hex to 40% EtOAc in i-hex). The target compound was isolated (711 mg, 49%) as an enriched mixture (5:1) of the desired diastereoisomer. LCMS (ES+) 367 (M+H)$^+$.

(1S*,2S*,3S*)-Methyl-1-chloro-2-(4-(5-methylpyrimidin-2-yl)phenyl)-3-phenylcyclopropanecarboxylate A solution of (1S*,2S*,3S*)-methyl-2-(4-bromophenyl)-1-chloro-3-phenylcyclopropanecarboxylate (710 mg, 1.9 mmol), bis-pinacolato diboron (476 mg, 1.9 mmol), Pd(dppf)$_2$O$_2$ (140 mg, 0.2 mmol), KOAc (816 mg, 8.3 mmol) in dioxane (15 mL) was stirred at 80° C. for 17 h. Water was added and the mixture was extracted with DCM, passed through a phase separator. The organic phase was concentrated and the crude used in the next step.

A solution of (1S*,2S*,3S*)-methyl-1-chloro-2-phenyl-3-(4-(4,4,5,5-tetramethyl-1,3,2-dioxaborolan-2-yl)phenyl)cyclopropanecarboxylate (1.8 mmol), Pd(dppf)$_2$Cl$_2$ (73 mg, 0.1 mmol), 5-methylpyrimidine bromide (280 mg, 1.8 mmol), and CsF (820 mg, 6.6 mmol) in dioxane (10 mL) was stirred at 90° C. for 17 h. The reaction mixture was diluted with water and extracted into DCM. The organic phase was passed through a phase separator and concentrated. Purification by flash silica column chromatography (gradient elution i-hex to 40% EtOAc in i-hex) followed by crystallization in EtOAc-i-hex (3:1) afforded the target compound (285 mg, 10%). LCMS (ES+) 379 (M+H)$^+$.

(1S,2S,3S)-1-Chloro-N-hydroxy-2-(4-(5-methylpyrimidin-2-yl)phenyl)-3-phenylcyclopropanecarboxamide Following method B from (1S*,2S*,3S*)-methyl-1-chloro-2-(4-(5-methylpyrimidin-2-yl)phenyl)-3-phenylcyclopropanecarboxylate (280 mg, 0.74 mmol). Purification by flash silica column chromatography (gradient elution DCM to 5% MeOH in DCM) gave the racemic compound (45 mg, 16%). Preparative chiral purification gave the title compound (Chiralpak IC 30/70 [IPA/MeOH (50/50/0.1% formic acid)]/heptane 1.0 mL/min, RT 12.1 min). LCMS (ES+) 379 (M+H)$^+$, RT 3.68 min. (Analytical method 1); $^1$H NMR δ (ppm)(DMSO-d$_6$): 11.00 (1H, s), 8.89 (1H, s), 8.68 (2H, s), 8.29 (2H, d, J=8.2 Hz), 7.49 (2H, d, J=8.2 Hz), 7.30-7.16 (5H, m), 3.70 (1H, d, J=8.9 Hz), 3.39 (1H, d, J=8.9 Hz), 2.25 (3H, s).

(1R,2R,3R)-1-Chloro-N-hydroxy-2-(4-(5-methylpyrimidin-2-yl)phenyl)-3-phenylcyclopropanecarboxamide (Chiralpak IC 30/70 [IPA/MeOH (50/50/0.1% formic acid)]/heptane 1.0 mL/min, RT 9.5 min)

Example 4

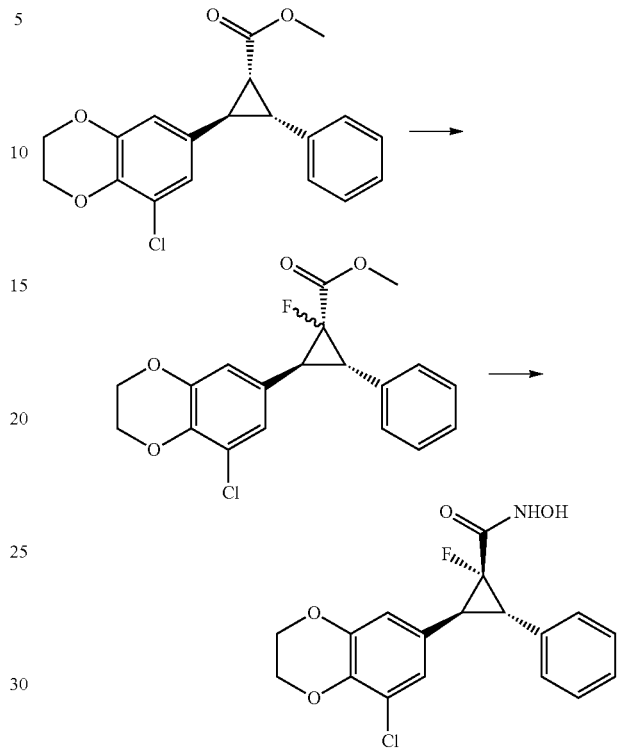

(1R*,2R*,3R*)-Ethyl-2-(8-chloro-2,3-dihydrobenzo[b][1,4]dioxin-6-yl)-3-phenylcyclopropanecarboxylate (E)-Ethyl-3-(8-chloro-2,3-dihydrobenzo[b][1,4]dioxin-6-yl)acrylate was prepared following method D from 8-chloro-2,3-dihydrobenzo[b][1,4]dioxine-6-carbaldehyde (700 mg, 3.53 mmol). The resulting yellow oil was used without further purification. LCMS (ES+) 269, 271 (M+H)$^+$.

Following method A from (E)-ethyl-3-(8-chloro-2,3-dihydrobenzo[b][1,4]dioxin-6-yl)acrylate (946 mg, 3.52 mmol) and 1-benzyltetrahydrothiophenium bromide (1.37 mg, 5.28 mmol). Purification by flash silica column chromatography (gradient elution i-hex to 10% EtOAc in i-hex) gave the title compound as a colourless oil (484 mg, 38%, 4:1 trans:cis). LCMS (ES+) 359, 361 (M+H)$^+$.

(1R*,2S*,3*S)-Ethyl-2-(8-chloro-2,3-dihydrobenzo[b][1,4]dioxin-6-yl)-1-fluoro-3-phenylcyclopropanecarboxylate To a solution of (1R*,2R*,3R*)-ethyl-2-(8-chloro-2,3-dihydrobenzo[b][1,4]dioxin-6-yl)-3-phenylcyclopropanecarboxylate, (360 mg, 1.0 mmol), LiCl (252 mg, 6.0 mmol) at −78° C., was added LDA (2N, 1.66 mL, 3.3 mmol). After stirring for 45 min, NFSI (1.04 g, 3.3 mmol) in dry THF (35 mL) was added and the reaction mixture was stirred for 1 h. The reaction was quenched with sat. NH$_4$Cl (50 mL) and extracted with DCM (150 mL). The organic phase was passed through a phase separator and concentrated to afford a crude compound that was purified by flash silica column chromatography (gradient elution i-hex to 40% EtOAc in i-hex). The target compound was isolated (280 mg, 75%) as a mixture of diastereoisomer. LCMS (ES+) 377 (M+H)+.

(1R*,2S*,3S*)-2-(8-Chloro-2,3-dihydrobenzo[b][1,4]dioxin-6-yl)-1-fluoro-N-hydroxy-3-phenylcyclopropanecarboxamide Following method B from (1R*,2S*,3S*)-ethyl-2-(8-chloro-2,3-dihydrobenzo[b][1,4]dioxin-6-yl)-1-fluoro-3-phenylcyclopropanecarboxylate (280 mg, 0.75 mmol). Purification by preparative achiral HPLC gave the title compound (108 mg, 40%). LCMS (ES+) 365 (M+H)+, RT 3.77 min (Analytical method 1); $^1$H NMR δ (ppm)(DMSO-$d_6$): 11.15 (1H, s), 9.02 (1H, s), 7.44-7.31 (5H, m), 7.01 (1H, d, J=2.0 Hz), 6.88 (1H, d, J=2.0 Hz), 4.39-4.30 (4H, m), 3.53-3.42 (2H, m).

Example 5

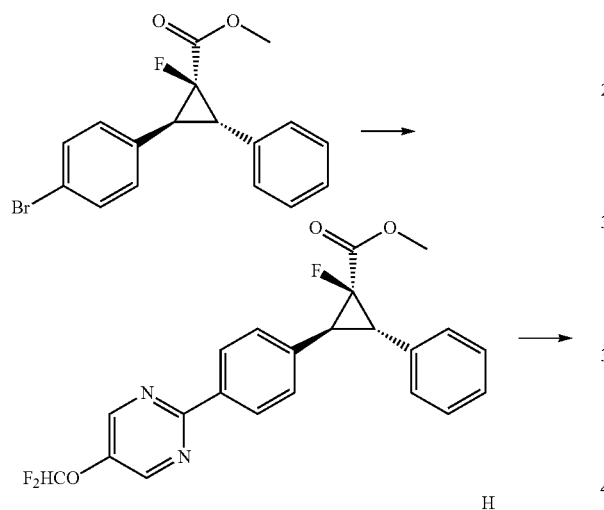

(1S*,2S*,3S*)-Methyl 2-(4-(5-(difluoromethoxy)pyrimidin-2-yl)phenyl)-1-fluoro-3-phenylcyclopropanecarboxylate A solution of (1S*,2S*,3S*)-methyl 2-(4-bromophenyl)-1-fluoro-3-phenylcyclopropanecarboxylate (337 mg, 0.96 mmol), bis-pinacolato diboron (295 mg, 1.2 mmol), Pd(dppf)$_2$Cl$_2$ (78 mg, 0.09 mmol), KOAc (114 mg, 1.2 mmol) in dioxane (10 mL) was stirred at 90° C. for 17 h. Water was added and the mixture was extracted with DCM and passed through a phase separator. The organic phase was concentrated and the crude used in the next step.

A solution of (1S*,2S*,3S*)-methyl-1-fluoro-2-phenyl-3-(4-(4,4,5,5-tetramethyl-1,3,2-dioxaborolan-2-yl)phenyl)cyclopropanecarboxylate (0.8 mmol), Pd(dppf)$_2$Cl$_2$ (33 mg, 0.04 mmol), 2-chloro-5-(difluoromethoxy)pyrimidine (222 mg, 1.2 mmol), and Cs$_2$CO$_3$ (390 mg, 1.2 mmol) in dioxane (5 mL) and water (1 mL), was stirred at 90° C. for 17 h. The reaction mixture was diluted with water and extracted into DCM. The organic phase was passed through a phase separator and concentrated. Purification by flash silica column chromatography (gradient elution i-hex to 40% EtOAc in i-hex) afforded the title compound (161 mg, 49%). LCMS (ES+) 415 (M+H)+.

(1S,2S,3S)-2-(4-(5-(Difluoromethoxy)pyrimidin-2-yl)phenyl)-1-fluoro-N-hydroxy-3-phenylcyclopropanecarboxamide Following method B from (1S*,2S*,3S*)-methyl 2-(4-(5-(difluoromethoxy)pyrimidin-2-yl)phenyl)-1-fluoro-3-phenylcyclopropanecarboxylate (156 mg, 0.38 mmol). Purification by achiral HPLC chromatography followed by chiral HPLC separation afforded the title compound (16.3 mg) (Chiralpak IA 50/50 [IPA/MeOH (0.1% formic acid)]/heptane 1.0 mL/min, RT 13.5 min). $^1$H NMR δ (ppm)(DMSO-$d_6$): $^1$H NMR (400 MHz, DMSO) 11.10 (1H, s), 8.90 (1H, s), 8.81 (2H, s), 8.28 (2H, d, J=8.6 Hz), 7.52 (2H, d, J=8.3 Hz), 7.34 (1H, t, J=73.0 Hz), 7.30-7.21 (4H, m), 7.19-7.14 (1H, m), 3.55 (1H, dd, J=9.6, 21.4 Hz), 3.51 (1H, s); LCMS (ES+) 416 (M+H)+, RT 3.82 min (Analytical method 1).

(1R,2R,3R)-2-(4-(5-(Difluoromethoxy)pyrimidin-2-yl)phenyl)-1-fluoro-N-hydroxy-3-phenylcyclopropanecarboxamide (Chiralpak IA 50/50 [IPA/MeOH (0.1% formic acid)]/heptane 1.0 mL/min, RT 7.8 min); LCMS (ES+) 416 (M+H)+, RT 3.83 min (Analytical method 1).

Example 6

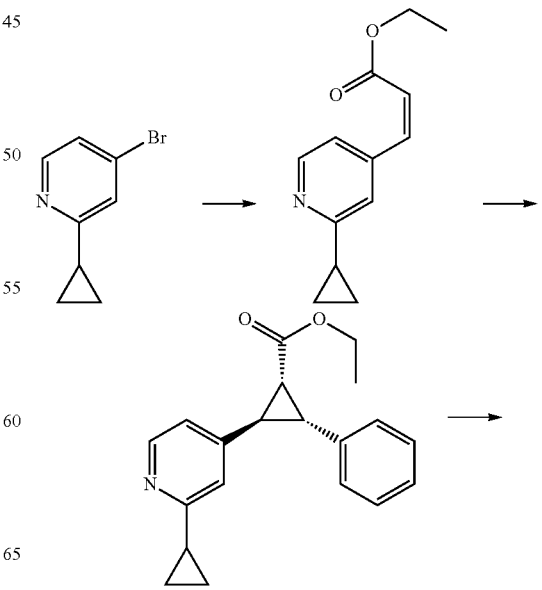

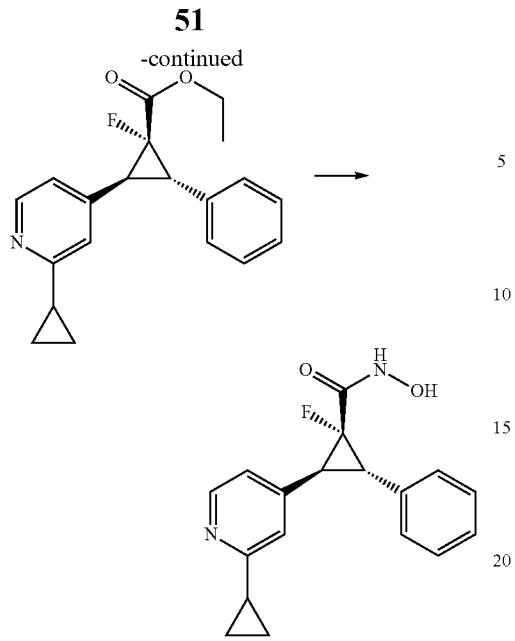

(E)-Ethyl-3-(2-cyclopropylpyridin-4-yl)acrylate

To a solution of 4-bromo-2-cyclopropylpyridine (1.7 g, 8.6 mmol), ethyl acrylate (1.2 mL, 11.2 mmol) and DABCO (1.92 g, 17.2 mmol) in DMF (25 mL) was added potassium carbonate (2.37 g, 17.2 mmol) and palladium acetate (192 mg, 0.86 mmol) and the mixture was stirred under $N_2$, at 125° C. for 17 h. The reaction mixture was diluted with water and extracted into EtOAc. The organic phase was washed with brine, dried over $Mg_2SO_4$, filtered and concentrated to give a yellow oil. Purification by flash silica column chromatography (gradient elution 5% EtOAc in i-hex to 15% EtOAc in i-hex) gave the title compound as a yellow oil (1.35 g 72%). LCMS (ES+) 218 (M+H)$^+$.

(1R*,2R*,3R*)-Ethyl 2-(2-cyclopropylpyridin-4-yl)-3-phenylcyclopropanecarboxylate Following method A from (E)-ethyl-3-(2-cyclopropylpyridin-4-yl)acrylate (1.3 g, 6 mmol) and 1-benzyltetrahydrothiophenium triflate (2.5 g, 7.8 mmol). Purification by flash silica column chromatography (gradient elution 30% EtOAc in i-hex to 50% EtOAc in i-hex) gave the title compound as a colourless oil (1.45 mg, 79%, 2:1 trans:cis). LCMS (ES+) 308 (M+H)$^+$.

(1R*,2S*,3S*)-Ethyl-2-(2-cyclopropylpyridin-4-yl)-1-fluoro-3-phenylcyclopropanecarboxylate To a solution of (1R*,2R*,3R*)-ethyl-2-(2-cyclopropylpyridin-4-yl)-3-phenylcyclopropanecarboxylate (750 mg, 2.4 mmol) and LiCl (1 g, 12.4 mmol) in dry THF (60 mL) stirred at −78° C. for 20 min, was added LDA (2 N, 4.1 mL, 8.2 mmol) and the reaction mixture was stirred at −78° C. for 45 min. Then a solution of NFSI (2.6 g, 8.2 mmol) in dry THF (10 mL) was added slowly and the reaction mixture was stirred for 45 min. The reaction was quenched with sat. $NH_4Cl$ (20 mL) and extracted with DCM (50 mL). The organic phase was passed through a phase separator and concentrated. Purification by flash silica column chromatography (gradient elution i-hex 10% to 20% EtOAc in i-hex), and achiral preparative HPLC purification (130 mg) gave the title compound as a mixture of diastereoisomers (4:1, (1R*,2S*,3S*):(1S*,2S*,3S*)). LCMS (ES+) 326 (M+H)$^+$.

(1R,2S,3S)-2-(2-Cyclopropylpyridin-4-yl)-1-fluoro-N-hydroxy-3-phenylcyclopropanecarboxamide Following method B from (1R*,2S*,3S*)-ethyl-2-(2-cyclopropylpyridin-4-yl)-1-fluoro-3-phenylcyclopropanecarboxylate (130 mg, 0.4 mmol). Purification by preparative achiral HPLC gave the title compound (10 mg). LCMS (ES+) 313 (M+H)$^+$, RT 2.32 min (Analytical method 1); $^1$H NMR δ (ppm)(DMSO-$d_6$) $^1$H NMR (400 MHz, DMSO) 11.19 (1H, s), 9.02 (1H, s), 8.29 (1H, d, J=5.0 Hz), 7.44-7.35 (4H, m), 7.34-7.30 (1H, m), 7.26 (1H, s), 7.08 (1H, dd, J=1.4, 5.1 Hz), 3.62-3.48 (2H, m), 2.10-2.03 (1H, m), 0.95-0.90 (4H, m).

Example 7

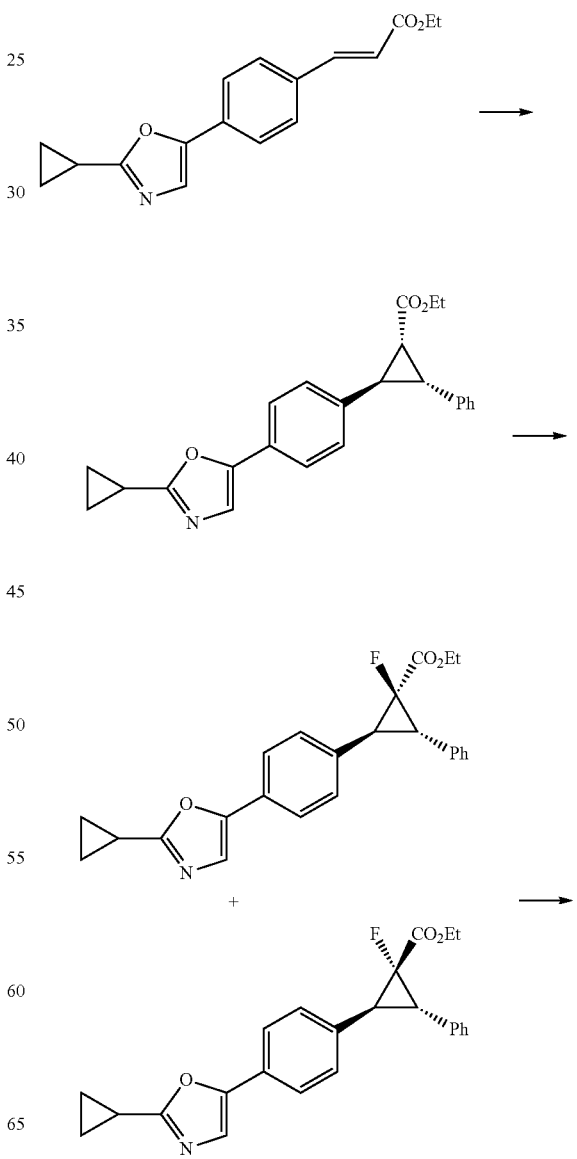

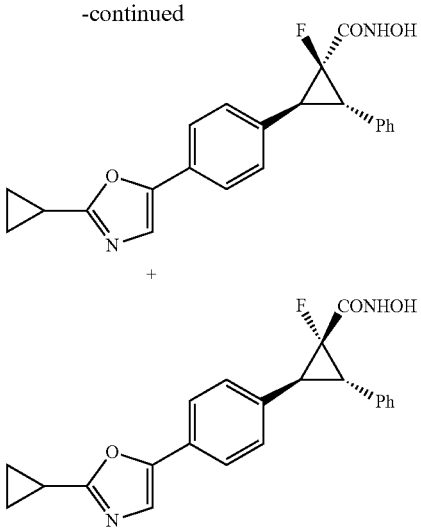

(E)-Ethyl 3-(4-(2-cyclopropyloxazol-5-yl)phenyl) acrylate

Following method E from 5-(4-bromophenyl)-2-cyclopropyloxazole (5.29 g, 19.7 mmol). The crude product was purified by flash silica column chromatography (gradient elution i-hex to 70% EtOAc in i-hex) affording the target compound as an oil (5.13 g). LCMS (ES+) 284 (M+H)+.

(1R*,2R*,3R*)-Ethyl 2-(4-(2-cyclopropyloxazol-5-yl)phenyl)-3-phenylcyclopropanecarboxylate Following method A using (E)-ethyl 3-(4-(2-cyclopropyloxazol-5-yl)phenyl)acrylate (1.5 g, 5.29 mmol). Purification by flash silica column chromatography (gradient elution i-hex to 40% EtOAc in i-hex) and afforded the title compound (1.93 g, 43%, trans:cis 85:15). LCMS (ES+) 374 (M+H)+.

(1S*,2S*,3S*)-Ethyl 2-(4-(2-cyclopropyloxazol-5-yl)phenyl)-1-fluoro-3-phenylcyclopropanecarboxylate To a solution of (1R*,2R*,3R*)-ethyl-2-(4-(2-cyclopropyloxazol-5-yl)phenyl)-3-phenylcyclopropanecarboxylate (1.93 mg, 15.5 mmol) in dry THF (70 mL) stirred at −78° C. for 20 min, was added LDA (2N, 7.75 mL, 15.5 mmol) and the reaction mixture was stirred at −78° C. for 30 min. Then a solution of NFSI (4.89 g, 15.5 mmol) in dry THF (25 mL) was added slowly and the reaction mixture was stirred for 20 h. The reaction was quenched with sat. NH₄Cl (200 mL) and extracted with DCM (100 mL). The organic phase was passed through a phase separator and concentrated. Purification by flash silica column chromatography (gradient elution i-hex to 30% EtOAc in i-hex). The target compound was isolated (780 mg) as a mixture of diastereoisomers (1:1, (1S*,2S*,3S*):(1R*,2S*,3S*)). LCMS (ES+) 392 (M+H)+.

(1S*,2S*,3S*)-2-(4-(2-cyclopropyloxazol-5-yl)phenyl)-1-fluoro-N-hydroxy-3-phenylcyclopropanecarboxamide and (1R*,2S*,3S*)-2-(4-(2-cyclopropyloxazol-5-yl)phenyl)-1-fluoro-N-hydroxy-3-phenylcyclopropanecarboxamide Following method B using (1S*,2S*,3S*)-ethyl 2-(4-(2-cyclopropyloxazol-5-yl)phenyl)-1-fluoro-3-phenylcyclopropanecarboxylate (108 mg, 0.27 mmol). Purification by achiral HPLC chromatography afforded the two diastereoisomers. (1S*,2S*,3S*)-2-(4-(2-cyclopropyloxazol-5-yl)phenyl)-1-fluoro-N-hydroxy-3-phenylcyclopropane carboxamide: LCMS (ES+) 379 (M+H)+ RT=3.67 min. ¹H NMR δ (ppm)(DMSO-d₆): 11.15 (1H, s), 8.91 (1H, s), 7.71-7.61 (2H, m), 7.49 (3H, d, J=9.07 Hz), 7.41-7.18 (5H, m), 3.59-3.46 (2H, m), 2.21-2.13 (1H, m), 1.11-0.98 (4H, m). (1R*,2S*,3S*)-2-(4-(2-cyclopropyloxazol-5-yl)phenyl)-1-fluoro-N-hydroxy-3-phenylcyclopropanecarboxamide: LCMS (ES+) 379 (M+H)+ RT=3.75 min. ¹H NMR δ (ppm)(DMSO-d₆): 11.14 (1H, s), 8.97 (1H, s), 7.58 (2H, d, J=8.1 Hz), 7.48-7.33 (7H, m), 7.34-7.27 (1H, m), 3.61-3.51 (2H, m), 2.20-2.12 (1H, m), 1.11-0.98 (4H, m).

Example 8

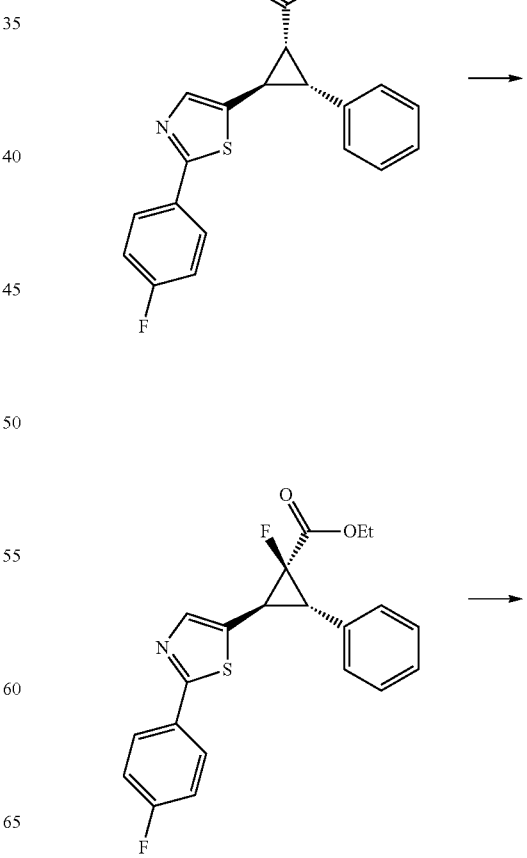

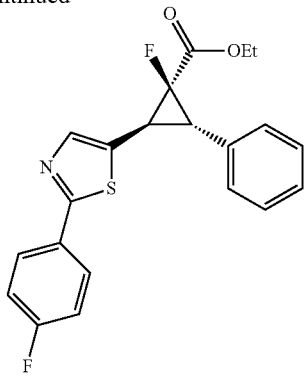

(E)-Ethyl-3-(2-bromothiazol-5-yl)acrylate

Following method D from 2-bromothiazole-5-carbaldehyde (10 g, 52.1 mmol). Purification by flash silica column chromatography (gradient elution i-hex to 20% EtOAc in i-hex) gave the title compound as a colourless oil (12.3 g, 90%). LCMS (ES+) 262, 264 (M+H)$^+$.

(1R*,2R*,3S*)-Ethyl-2-(2-bromothiazol-5-yl)-3-phenylcyclopropanecarboxylate

Following method A from (E)-ethyl-3-(2-bromothiazol-5-yl)acrylate (540 mg, 2.06 mmol) and 1-tetrahydro-1H-thiophenium triflate (1.01 g, 3.09 mmol). Purification by flash silica column chromatography (gradient elution i-hex to 10% EtOAc in i-hex) gave the title compound (600 mg, 83%, 1:1 trans:cis). LCMS (ES+) 352, 354 (M+H)$^+$.

(1R*,2R*,3S*)-Ethyl-2-(2-(4-fluorophenyl)thiazol-5-yl)-3-phenylcyclopropanecarboxylate A suspension of (1R*,2R*,3S*)-ethyl-2-(2-bromothiazol-5-yl)-3-phenylcyclopropanecarboxylate (1.0 g, 2.8 mmol), p-fluoro phenyl boronic acid (441 mg, 3.15 mmol), Pd(PPh$_3$)$_4$ (181 mg, 0.15 mmol), 2N Na$_2$CO$_3$ (4 mL) in dioxane (20 mL) was stirred at 90° C. overnight. Water was added and the reaction mixture was extracted in DCM, the organic phase was passed through a phase separator cartridge, concentrated and purified by silica gel column chromatography to afford the target compound (815 mg, cis:trans 1:1). LCMS (ES+) 368 (M+H)$^+$.

(1S*,2R*,3S*)-Ethyl-1-fluoro-2-(2-(4-fluorophenyl)thiazol-5-yl)-3-phenylcyclopropanecarboxylate To a solution of (1R*,2R*,3S*)-ethyl-2-(2-(4-fluorophenyl)thiazol-5-yl)-3-phenylcyclopropanecarboxylate (813 mg, 2.0 mmol) and 12-crown-4 (1.3 mL, 6.6 mmol) in dry THF (30 mL) stirred at −78° C. for 20 min, was added LDA (2N, 3.3 mL, 6.6 mmol) and the reaction mixture was stirred at −78° C. for 30 min. Then a solution of NFSI (2.08 g, 6.6 mmol) in dry THF (20 mL) was added slowly and the reaction mixture was stirred for 2 h. The reaction was quenched with sat NH$_4$Cl (20 mL) and extracted with DCM (50 mL). The organic phase was passed through a phase separator and concentrated to afford a crude that was purified by flash silica column chromatography (gradient elution i-hex to 40% EtOAc in i-hex). The target compound was isolated as a mixture of diastereoisomers (513 mg, 1:1, (1 S*,2R*,3S*):(1R*,2R*,3S*)). (LCMS (ES+) 386 (M+H)+.

(1S,2R,3S)-1-Fluoro-2-(2-(4-fluorophenyl)thiazol-5-yl)-N-hydroxy-3-phenylcyclopropanecarboxamide Following method B using (1S*,2R*,3S*)-ethyl 1-fluoro-2-(2-(4-fluorophenyl)thiazol-5-yl)-3-phenylcyclopropanecarboxylate (510 mg, 1.3 mmol). Purification by achiral HPLC chromatography followed by chiral HPLC separation afforded the title compound. (Chiralpak IC 20/80 IPA/MeOH (50/50/0.1% formic acid/heptane, 1.0 mL/min, RT=13.8 min) LCMS (ES+) 373 (M+H)$^+$, RT=3.83 min (Analytical method 1). $^1$H NMR δ (ppm)(DMSO-d$_6$): 11.31 (1H, s), 9.04 (1H, s), 8.06-7.99 (3H, m), 7.43-7.26 (7H, m), 3.78 (1H, dd, J=9.2, 3.9 Hz), 3.48 (1H, dd, J=23.3, 9.2 Hz).

Example 9

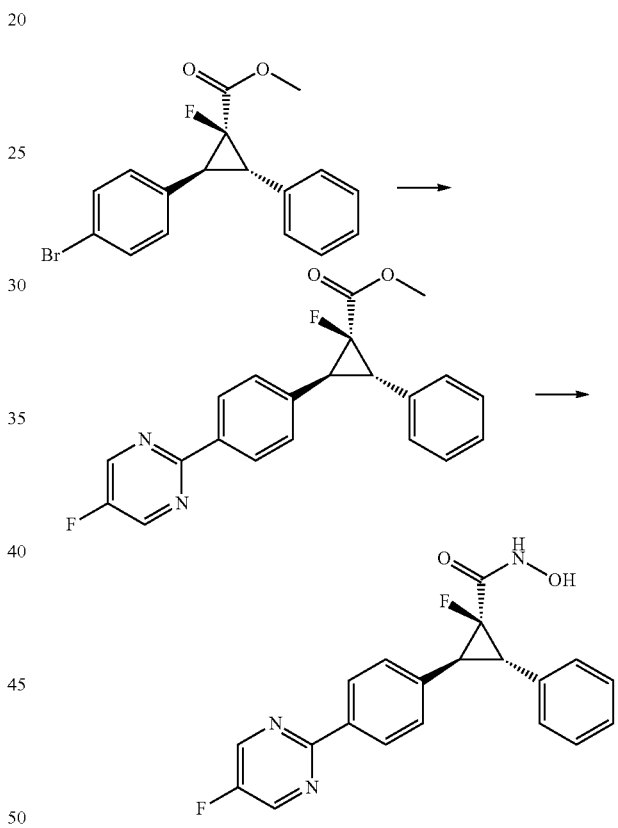

(1S*,2S*,3S*)-Methyl-1-fluoro-2-(4-(5-fluoropyrimidin-2-yl)phenyl)-3-phenylcyclopropanecarboxylate A solution of (1S*,2S*,3S*)-methyl-2-(4-bromophenyl)-1-fluoro-3-phenylcyclopropanecarboxylate (3.88 g, 12.2 mmol), bis-pinacolato diboron (3.40 g, 13.4 mmol), Pd(dppf)$_2$Cl$_2$ (995 mg, 1.22 mmol), KOAc (5.97 g, 61.0 mmol) in dioxane (100 mL) was stirred at 90° C. for 17 h. Water was added and the mixture was extracted with DCM and passed through a phase separator. The organic phase was concentrated and the crude used in the next step.

A solution of (1S*,2S*,3S*)-methyl-1-fluoro-2-phenyl-3-(4-(4,4,5,5-tetramethyl-1,3,2-dioxaborolan-2-yl)phenyl)cyclopropanecarboxylate (4.83 g, 12.2 mmol), Pd(dppf)$_2$Cl$_2$ (995 mg, 1.22 mmol), 2-chloro-5-fluoropyrimidine (1.76 g, 14.6 mmol), and CsF (6.12 g, 40.3 mmol) in dioxane (100 mL) was stirred at 100° C. for 17 h. The reaction mixture was diluted with water and extracted into DCM. The organic phase was passed through a phase separator and concentrated. Purification by flash silica column chromatography (gradient elution i-hex to 30% EtOAc in i-hex) afforded the target compound (3.78 g, 85%). LCMS (ES+) 367 (M+H)+.

(1S,2S,3S)-1-Fluoro-2-(4-(5-fluoropyrimidin-2-yl)phenyl)-N-hydroxy-3-phenylcyclopropanecarboxamide Following method B from (1S*,2S*,3S*)-methyl-1-fluoro-2-(4-(5-fluoropyrimidin-2-yl)phenyl)-3-phenyl cyclopropanecarboxylate (130 mg, 0.36 mmol). The target compound was obtained after flash silica column chromatography (gradient elution DCM to 5% MeOH in DCM) followed by chiral HPLC purification (37.3 mg). (Chiralpak IC EtOH (0.1% formic acid/heptane 1.0 mL/min, RT 7.0 min). LCMS (ES+) 368 (M+H)+, RT 3.73 min (Analytical method 1); 1H NMR δ (ppm)(DMSO-d6): 11.07 (1H, s), 8.91 (2H, s), 8.87 (1H, s), 8.26 (2H, d, J=8.2 Hz), 7.51 (2H, d, J=8.19 Hz), 7.31-7.20 (4H, m), 7.16 (1H, t, J=7.0 Hz), 3.58-3.48 (2H, m).

(1R,2R,3R)-1-Fluoro-2-(4-(5-fluoropyrimidin-2-yl)phenyl)-N-hydroxy-3-phenylcyclopropanecarboxamide (Chiralpak IC EtOH (0.1% formic acid)/heptane 1.0 mL/min, RT 5.5 min). LCMS (ES+) 368 (M+H)+, RT 3.73 min (Analytical method 1)

Example 10

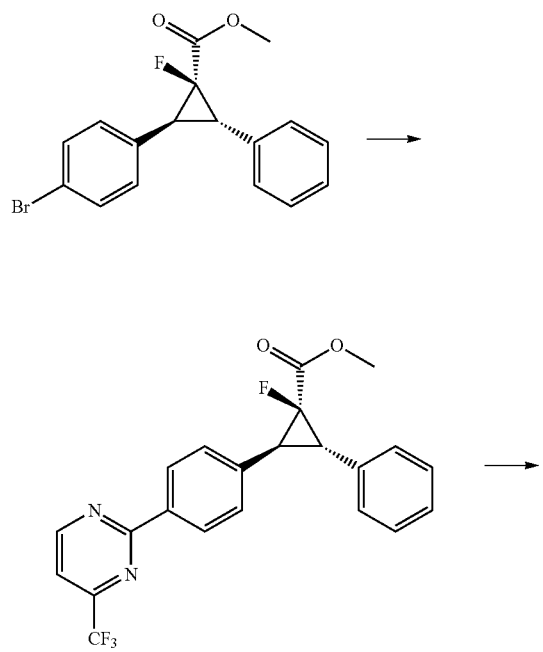

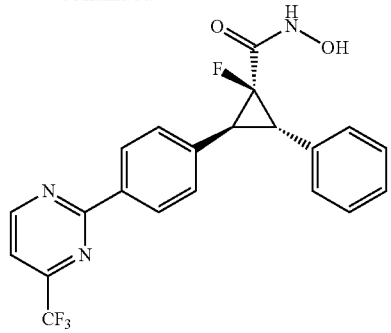

(1S*,2S*,3S*)-Methyl-1-fluoro-2-phenyl-3-(4-(4-(trifluoromethyl)pyrimidin-2-yl)phenyl)cyclopropanecarboxylate To a stirred solution of (1S*,2S*,3S*)-methyl-2-(4-bromophenyl)-1-fluoro-3-phenylcyclopropane carboxylate (470 mg, 1.47 mmol) in dioxane (10 mL) was added bis-pinacolato diboron (412 mg, 1.62 mmol), Pd(dppf)Cl2 (120 mg, 0.15 mmol) and potassium acetate (720 mg, 7.35 mmol). The mixture was degassed with nitrogen and heated to 100° C. for 2 h. The reaction mixture was diluted with H2O (20 mL) and extracted into DCM (2×20 mL). The organic phase was concentrated and the crude used in the next step.

A solution of (1S*,2S*,3S*)-methyl-1-fluoro-2-phenyl-3-(4-(4,4,5,5-tetramethyl-1,3,2-dioxaborolan-2-yl)phenyl)cyclopropanecarboxylate (538 mg, 1.47 mmol), Pd(dppf)2Cl2 (169 mg, 0.15 mmol), 2-bromo-4-(trifluoromethyl)pyrimidine (367 mg, 1.62 mmol), and 2 M Na2CO3 (aq) (2.2 mL, 4.41 mmol) in dioxane (15 mL) was stirred at 100° C. for 17 h. The reaction mixture was diluted with water and extracted into DCM. The organic phase was passed through a phase separator and concentrated. Purification by flash silica column chromatography (gradient elution i-hex to 30% EtOAc in i-hex) afforded the target compound (230 mg, 41%). LCMS (ES+) 417 (M+H)+.

(1S,2S,3S)-1-Fluoro-N-hydroxy-2-phenyl-3-(4-(4-(trifluoromethyl)pyrimidin-2-yl)phenyl)cyclopropane carboxamide Following method B from (1S*,2S*,3S*)-methyl-1-fluoro-2-phenyl-3-(4-(4-(trifluoromethyl)pyrimidin-2-yl)phenyl)cyclopropanecarboxylate (230 mg, 0.55 mmol) The target compound was obtained after flash silica column chromatography (gradient elution DCM to 3% MeOH in DCM) followed by chiral HPLC purification (46 mg). (Chiralpak IC IPA/MeOH (50/50/0.1% formic acid/heptane 1.0 mL/min, RT 15.3 min). LCMS (ES+) 418 (M+H)+, RT 4.14 min (Analytical method 1); 1H NMR δ (ppm)(DMSO-d6): 11.21 (1H, s), 9.33 (1H, d, J=5.0 Hz), 9.01 (1H, s), 8.47 (2H, d, J=8.2 Hz), 8.00 (1H, d, J=5.0 Hz), 7.70 (2H, d, J=8.2 Hz), 7.45-7.35 (4H, m), 7.33-7.27 (1H, m), 3.69-3.62 (2H, m).

(1R,2R,3R)-1-Fluoro-N-hydroxy-2-phenyl-3-(4-(4-(trifluoromethyl)pyrimidin-2-yl)phenyl)cyclopropane carboxamide (Chiralpak IC IPA/MeOH (50/50/0.1% formic acid)/heptane 1.0 mL/min, RT 11.4 min). LCMS (ES+) 418 (M+H)+, RT 4.14 min (Analytical method 1).

Example 11

Analysis of Inhibition of HDAC4 with Class IIa Histone Deacetylase (HDAC) Inhibitors The potency of Class IIa Histone Deacetylase (HDAC) inhibitors is quantified by measuring the Histone Deacetylase 4 (HDAC4) catalytic domain enzymatic activity using the Class IIa selective substrate, Boc-Lys(Tfa)-AMC. The substrate is deacetylated to Boc-Lys-AMC by HDAC4. Cleavage by trypsin results in the release of the fluorophore AMC from the deacetylated substrate. The fluorescence of the sample is directly related to the histone deacetylase activity in the sample.

Serially Dilute HDAC Inhibitor Compounds.

Serial dilutions of the HDAC inhibitors and control reference compound (1-(5-(3-((4-(1,3,4-oxadiazol-2-yl)phenoxy)methyl)-1,2,4-oxadiazol-5-yl)thiophen-2-yl)-2,2,2-trifluoroethanone) are made by first resuspending the lyophilized compound to a final concentration of 10 mM in 100% dimethyl sulfoxide (DMSO). Stocks of 60 µl aliquots of the 10 mM compound in DMSO are prepared and stored at −20° C. From one stock aliquot of each compound to be tested and the reference compound, a 16-point serial dilution is prepared according to Table 1 using a 125 µl 16-channel Matrix multi-channel pipette (Matrix Technologies Ltd).

TABLE 1

Serial Dilution of Compounds

| Diluted Solutions | Well | Concentration (µM) | Dilution ratio | Volumes |
|---|---|---|---|---|
| Concentration 1 | A | 10000 | — | 60 µL 10 mM Test compound/reference control |
| Concentration 2 | B | 5000 | 1:2 | 30 µl A + 30 µl DMSO |
| Concentration 3 | C | 2500 | 1:2 | 30 µl B + 30 µl DMSO |
| Concentration 4 | D | 1000 | 1:2.5 | 30 µl C + 45 µl DMSO |
| Concentration 5 | E | 500 | 1:2 | 30 µl D + 30 µl DMSO |
| Concentration 6 | F | 250 | 1:2 | 30 µl E + 30 µl DMSO |
| Concentration 7 | G | 125 | 1:2 | 30 µl F + 30 µl DMSO |
| Concentration 8 | H | 62.5 | 1:2 | 30 µl G + 30 µl DMSO |
| Concentration 9 | I | 31.25 | 1:2 | 30 µl H + 30 µl DMSO |
| Concentration 10 | J | 15.63 | 1:2 | 30 µl I + 30 µl DMSO |
| Concentration 11 | K | 7.81 | 1:2 | 30 µl J + 30 µl DMSO |
| Concentration 12 | L | 3.91 | 1:2 | 30 µl K + 30 µl DMSO |
| Concentration 13 | M | 1.95 | 1:2 | 30 µl L + 30 µl DMSO |
| Concentration 14 | N | 0.98 | 1:2 | 30 µl M + 30 µl DMSO |
| Concentration 15 | O | 0.49 | 1:2 | 30 µl N + 30 µl DMSO |
| Concentration 16 | P | 0.24 | 1:2 | 30 µl O + 30 µl DMSO |

2 µl (200×) of each diluted solution and each control (full activity: 100% DMSO alone or full inhibition 1 mM) is stamped into V-bottomed polypropylene 384-well compound plates using either the Bravo (384-well head from Agilent) or 12.5 µl 16-channel Matrix multi-channel pipette (Matrix Technologies Ltd). Each well with the 200× compound solution is diluted 1:20 by the addition of 38 µl assay buffer+DMSO (10.5% DMSO, 45 mM Tris-HCl, 123 mM NaCl, 2.4 mM KCl, and 0.9 mM $MgCl_2$ at pH 8.0 and equilibrated to room temperature.

Prepare HDAC4 Catalytic Domain Enzyme (0.86 µg/ml).

The HDAC4 catalytic domain enzyme is human catalytic domain HDAC4 protein (amino acids 648-1057, but with a replacement of amino acids 730-744 with 4 amino acid GSGS linker) made from VOID 3428 and provided by Emerald Biostructures at 1.2 mg/ml. A working solution of enzyme is prepared from a 1.2 mg/ml stock aliquot of HDAC4 catalytic domain (thawed on ice) diluted to 0.86 µg/ml with assay buffer (50 mM Tris-HCl, 137 mM NaCl, 2.7 mM KCl, and 1 mM $MgCl_2$ at pH 8 and equilibrated to room temperature) just prior to the addition of the enzyme to the assay.

Prepare 5× (50 NM) Boc-Lys(Tfa)-AMC Substrate.

5× (50 µM) substrate is prepared just prior to the addition to the assay. A 1 mM substrate stock is made by diluting a 100 mM Boc-Lys(Tfa)-AMC in DMSO solution 1:100 by adding it drop-wise to assay buffer (equilibrated to room temperature) while vortexing at slow speed to prevent precipitation. The 5× substrate is prepared by diluting the 1 mM substrate solution 1:20 by adding it drop-wise to assay buffer (equilibrated to room temperature) while vortexing at slow speed to prevent precipitation.

Prepare 3× (30 NM) Developer/Stop Solution.

3× (30 µM) Developer/Stop Solution is prepared just prior to addition to the plate by diluting a stock solution of 10 mM reference compound 1:333 in 25 mg/ml trypsin (PAA Laboratories Ltd.) equilibrated to room temperature.

Assay.

5 µl of each solution of 1:20 diluted compound from above is transferred to a clear bottomed, black, 384-well assay plate using the Bravo or the Janus (384-well MDT head from Perkin Elmer). Using a 16-channel Matrix multi-channel pipette, 35 µl of the working solution of HDAC4 catalytic domain enzyme (0.86 µg/ml in assay buffer) is transferred to the assay plate. The assay is then started by adding 10 µl of 5× (50 µM) substrate to the assay plates using either the Bravo, Janus or 16-channel Matrix multi-channel pipette. The assay plate is then shaken for two minutes on an orbital shaker at 900 rpm (rotations per minute). Next the plate is incubated for 15 minutes at 37° C. The reaction is stopped by adding 25 µl of 3× (30 µM) developer/stop solution to the assay plates using either the Bravo, Janus or a 16-channel Matrix multi-channel pipette. Assay plates are then shaken for 5 minutes on an orbital shaker at 1200 rpm. Next, the assay plates are incubated at 37° C. for 1 hour in a tissue culture incubator. Finally, the fluorescence is measured (Excitation: 355 nm, Emission: 460 nm) using PerkinElmer EnVision in top read mode.

Example 12

Analysis of Inhibition of HDAC5 with Class IIa Histone Deacetylase (HDAC) Inhibitors The potency of Class IIa Histone Deacetylase (HDAC) inhibitors is quantified by measuring the Histone Deacetylase 5 (HDAC5) enzymatic activity using the Class IIa selective substrate, Boc-Lys(Tfa)-AMC. The substrate is deacetylated to Boc-Lys-AMC by HDAC5. Cleavage by trypsin results in the release of the fluorophore AMC from the deacetylated substrate. The fluorescence of the sample is directly related to the histone deacetylase activity in the sample.

Serially Dilute HDAC Inhibitor Compounds.

Serial dilutions of the HDAC inhibitors and control reference compound (1-(5-(3-((4-(1,3,4-oxadiazol-2-yl)phenoxy)methyl)-1,2,4-oxadiazol-5-yl)thiophen-2-yl)-2,2,2-trifluoroethanone) are made by first resuspending the lyophilized compound to a final concentration of 10 mM in 100% DMSO. Stocks of 60 µl aliquots of the 10 mM compound in DMSO are prepared and stored at −20° C. From one stock aliquot of each compound to be tested and the reference compound, a 16-point serial dilution is prepared according to Table 1 using a 125 µl 16-channel Matrix multi-channel pipette.

2 µl (200×) of each diluted solution and each control (full activity: 100% DMSO alone or full inhibition 1 mM) is stamped into V-bottom polypropylene 384-well compound plates using either Bravo, Janus, or a 12.5 µl 16-channel Matrix multi-channel pipette. Each well with the 2 µl of the 200× stamped compound solution is diluted 1:20 by the addition of 38 µl assay buffer+DMSO (10.5% DMSO, 45 mM Tris-HCl, 123 mM NaCl, 2.4 mM KCl, and 0.9 mM $MgCl_2$ at pH 8.0 and equilibrated to 37° C.).

Prepare HDAC5 Catalytic Domain Enzyme (0.57 µg/ml).

The HDAC5 catalytic domain enzyme is human HDAC5 catalytic domain (GenBank Accession No. NM_001015053), amino acids 657-1123 with a C-terminal His tag and can be obtained from BPS BioScience. The protein is 51 kDa and is expressed in a baculovirus expression system. A working solution of enzyme is prepared from a 1.65 mg/ml stock aliquot of HDAC5 catalytic domain (thawed on ice) diluted to 0.57 µg/ml with assay buffer (50 mM Tris-HCl, 137 mM NaCl, 2.7 mM KCl, and 1 mM $MgCl_2$ at pH 8 and equilibrated to 37° C.) just prior to the addition of the enzyme to the assay.

Prepare 5× (40 µM) Boc-Lys(Tfa)-AMC Substrate.

5× (40 µM) substrate is prepared just prior to the addition to the assay. The 5× substrate is prepared by diluting the 100 mM Boc-Lys(Tfa)-AMC in DMSO solution 1:2500 by adding it drop-wise to assay buffer (equilibrated to 37° C.) while vortexing at slow speed to prevent precipitation.

Prepare 3× (30 µM) Developer/Stop Solution.

3× (30 µM) Developer/Stop Solution is prepared just prior to addition to the plate by diluting a stock solution of 10 mM reference compound 1:333 in 25 mg/ml trypsin equilibrated to 37° C.

Assay.

5 µl of each solution of the 1:20 diluted inhibitor compounds and controls from above is transferred to a clear bottomed, black, 384-well assay plate using the Bravo or Janus. Using a 16-channel Matrix multi-channel pipette, 35 µl of the working solution of the HDAC5 catalytic domain enzyme (0.57 µg/ml in assay buffer) is transferred to the assay plate. The assay is then started by adding 10 µl of 5× (40 µM) substrate to the assay plates using either the Bravo, Janus or 16-channel Matrix multi-channel pipette. The assay plate is then shaken for one minute on an orbital shaker at 900 rpm. Next, the plates are incubated for 15 minutes at 37° C. The reaction is stopped by adding 25 µl of 3× (30 µM) developer/stop solution to the assay plates using either the Bravo, Janus or a 16-channel Matrix multi-channel pipette. Assay plates are then shaken for 2 minutes on an orbital shaker at 900 rpm. Next, the assay plates are incubated at 37° C. for 1 hour in a tissue culture incubator followed by shaking for 1 minute at the maximum rpm on an orbital shaker before reading on the EnVision. Finally, the fluorescence is measured (Excitation: 355 nm, Emission: 460 nm) using PerkinElmer EnVision in top read mode.

Example 13

Analysis of Inhibition of HDAC7 with Class IIa Histone Deacetylase (HDAC) Inhibitors The potency of Class IIa Histone Deacetylase (HDAC) inhibitors is quantified by measuring the Histone Deacetylase 7 (HDAC7) enzymatic activity using the Class IIa selective substrate, Boc-Lys(Tfa)-AMC. The substrate is deacetylated to Boc-Lys-AMC by HDAC7. Cleavage by trypsin results in the release of the fluorophore AMC from the deacetylated substrate. The fluorescence of the sample is directly related to the histone deacetylase activity in the sample.

Serially Dilute HDAC Inhibitor Compounds.

Serial dilutions of the HDAC inhibitors and control reference compound (1-(5-(3-((4-(1,3,4-oxadiazol-2-yl)phenoxy)methyl)-1,2,4-oxadiazol-5-yl)thiophen-2-yl)-2,2,2-trifluoroethanone) are made by first resuspending the lyophilized compound to a final concentration of 10 mM in 100% DMSO. Stocks of 60 µl aliquots of the 10 mM compound in DMSO are prepared and stored at −20° C. From one stock aliquot of each compound to be tested and the reference compound, a 16-point serial dilution is prepared according to Table 1 using a 125 µl 16-channel Matrix multi-channel pipette.

2 µl (200×) of each diluted solution and each control (full activity: 100% DMSO alone or full inhibition 1 mM) is stamped into V-bottom polypropylene 384-well compound plates using either the Bravo, Janus, or a 12.5 µl 16-channel Matrix multi-channel pipette. Each well with the 200× compound solution is diluted 1:20 by the addition of 38 µl assay buffer+DMSO (10.5% DMSO, 45 mM Tris-HCl, 123 mM NaCl, 2.4 mM KCl, and 0.9 mM $MgCl_2$ at pH 8.0 and equilibrated to 37° C.).

Prepare HDAC7 Enzyme (71 ng/ml).

The HDAC7 enzyme is human HDAC7 (GenBank Accession No. AY302468) amino acids 518-end with a N-terminal Glutathione S-transferase (GST) tag and can be obtained from BPS BioScience. The protein is 78 kDa and is expressed in a baculovirus expression system. A working solution of enzyme is prepared from a 0.5 mg/ml stock aliquot of HDAC7 (thawed on ice) diluted to 71 ng/ml with assay buffer (50 mM Tris-HCl, 137 mM NaCl, 2.7 mM KCl, and 1 mM $MgCl_2$ at pH 8 and equilibrated to 37° C.) just prior to the addition of enzyme to the assay.

Prepare 5× (50 µM) Boc-Lys(Tfa)-AMC Substrate.

5× (50 µM) substrate is prepared just prior to the addition to the assay. The 5× substrate is prepared by diluting a 100 mM Boc-Lys(Tfa)-AMC in DMSO solution 1:2000 by adding it drop-wise to assay buffer (equilibrated to 37° C.) while vortexing at slow speed to prevent precipitation.

Prepare 3× (30 µM) Developer/Stop Solution.

3× (30 µM) Developer/Stop Solution is prepared just prior to addition to the plate by diluting a stock solution of 10 mM reference compound 1:333 in 25 mg/ml trypsin equilibrated to 37° C.

Assay.

5 µl of each solution of 1:20 diluted compound from above is transferred to a clear bottomed, black, 384-well assay plate using the Bravo or Janus. Using a 16-channel Matrix multi-channel pipette, 35 µl of the working solution of the HDAC7 enzyme (71 ng/ml in assay buffer) is transferred to the assay plate. The assay is then started by adding 10 µl of 5× (50 µM) substrate to the assay plate using either the Bravo, Janus or 16-channel Matrix multi-channel pipette. The assay plate is then shaken for one minute on an orbital shaker at 900 rpm. Next, the plate is incubated for 15 minutes at 37° C. The reaction is then stopped by adding 25 µl of 3× (30 µM) developer/stop solution to the assay plates using either the Bravo, Janus or a 16-channel Matrix multi-channel pipette. The assay plate is then shaken for 2 minutes on an orbital shaker at 900 rpm. Next, the assay plate is incubated at 37° C. for 1 hour in a tissue culture incubator followed by shaking for 1 minute at maximum rpm on an orbital shaker. Finally, the fluorescence is measured (Excitation: 355 nm, Emission: 460 nm) using PerkinElmer EnVision in top read mode.

Example 14

Analysis of Inhibition of HDAC9 with Class IIa Histone Deacetylase (HDAC) Inhibitors The potency of Class IIa Histone Deacetylase (HDAC) inhibitors is quantified by measuring the Histone Deacetylase 9 (HDAC9) enzymatic activity using the Class IIa selective substrate, Boc-Lys(Tfa)-AMC. The substrate is deacetylated to Boc-Lys-AMC by HDAC9. Cleavage by trypsin results in the release of the fluorophore AMC from the deacetylated substrate. The fluorescence of the sample is directly related to the histone deacetylase activity in the sample.

Serially Dilute HDAC Inhibitor Compounds.

Serial dilutions of the HDAC inhibitors and control reference compound (1-(5-(3-((4-(1,3,4-oxadiazol-2-yl)phenoxy)methyl)-1,2,4-oxadiazol-5-yl)thiophen-2-yl)-2,2,2-trifluoroethanone) are made by first resuspending the lyophilized compound to a final concentration of 10 mM in 100% DMSO. Stocks of 60 µl aliquots of the 10 mM compound in DMSO are prepared and stored at −20° C. From one stock aliquot of each compound to be tested and the reference compound, a 16-point serial dilution is prepared according to Table 1 using a 125 µl 16-channel Matrix multi-channel pipette.

2 µl (200×) of each diluted solution and each control (full activity: 100% DMSO alone or full inhibition 1 mM) is stamped into V-bottom polypropylene 384-well compound plates using either the Bravo, Janus, or 12.5 µl 16-channel Matrix multi-channel pipette. Each well with the stamped 200× compound solution is diluted 1:20 by the addition of 38 µl assay buffer+DMSO (10.5% DMSO, 45 mM Tris-HCl, 123 mM NaCl, 2.4 mM KCl, and 0.9 mM $MgCl_2$ at pH 8.0 and equilibrated to 37° C.).

Prepare HDAC9 Enzyme (0.57 µg/ml).

The HDAC9 enzyme is human HDAC9 (GenBank Accession No. NM_178423) amino acids 604-1066 with a C-terminal His tag and can be obtained from BPS BioScience. The protein is 50.7 kDa and is expressed in a baculovirus expression system. A working solution of enzyme is prepared from a 0.5 mg/ml stock aliquot of HDAC9 (thawed on ice) diluted to 0.57 µg/ml with assay buffer (50 mM Tris-HCl, 137 mM NaCl, 2.7 mM KCl, and 1 mM $MgCl_2$ at pH 8 and equilibrated to 37° C.) just prior to the addition of enzyme to the assay.

Prepare 5× (125 µM) Boc-Lys(Tfa)-AMC Substrate.

5× (125 µM) substrate is prepared just prior to the addition to the assay. The 5× substrate is prepared by diluting a 100 mM Boc-Lys(Tfa)-AMC in DMSO solution 1:800 by adding it drop-wise to assay buffer (equilibrated to 37° C.) while vortexing at slow speed to prevent precipitation.

Prepare 3× (30 µM) Developer/Stop Solution.

3× (30 µM) Developer/Stop Solution is prepared just prior to addition to the plate by diluting a stock solution of 10 mM reference compound 1:333 in 25 mg/ml trypsin equilibrated to 37° C.

Assay.

5 µl of each solution of 1:20 diluted compound from above is transferred to a clear bottomed, black, 384-well assay plate using the Bravo or Janus. Using a 16-channel Matrix multi-channel pipette, 35 µl of the working solution of the HDAC9 enzyme (0.57 µg/ml in assay buffer) is transferred to the assay plate. The assay is then started by adding 10 µl of 5× (125 µM) substrate to the assay plate using either the Bravo, Janus or 16-channel Matrix multi-channel pipette. The assay plate is then shaken for one minute on an orbital shaker at 900 rpm. Next, the plate is incubated for 15 minutes at 37° C. The reaction is stopped by adding 25 µl of 3× developer/stop solution to the assay plates using either the Bravo, Janus or a 16-channel Matrix multi-channel pipette. The assay plate is then shaken for 2 minutes on an orbital shaker at 900 rpm. Next, the assay plate is incubated at 37° C. for 1 hour in a tissue culture incubator followed by shaking for 1 minute at maximum rpm on an orbital shaker before reading on the enVision. Finally, the fluorescence is measured (Excitation: 355 nm, Emission: 460 nm) using PerkinElmer EnVision in top read mode.

Example 15

Analysis of Inhibition of Cellular HDAC Activity with Class IIa Histone Deacetylase (HDAC) Inhibitors The potency of Class IIa Histone Deacetylase (HDAC) inhibitors is quantified by measuring the cellular histone deacetylase enzymatic activity using the Class IIa selective substrate, Boc-Lys(Tfa)-AMC. After penetration in Jurkat E6-1 cells, the substrate is deacetylated to Boc-Lys-AMC. After cell lysis and cleavage by trypsin, the fluorophore AMC is released from the deacetylated substrate only. The fluoresence of the sample is directly related to the histone deacetylase activity in the sample.

Jurkat E6.1 Cell Culture and Plating.

Jurkat E6.1 cells are cultured according to standard cell culture protocols in Jurkat E6.1 Growth Media (RPMI without phenol red, 10% FBS, 10 mM HEPES, and 1 mM Sodium Pyruvate). Jurkat E6.1 cells are counted using a Coulter Counter and resuspended in Jurkat E6.1 growth media at a concentration of 75,000 cells/35 µl. 35 µl or 75,000 cells is seeded into Greiner microtitre assay plates. The plates are then incubated at 37° C. and 5% $CO_2$ while other assay components are being prepared.

Serially Dilute HDAC Inhibitor Compounds.

Serial dilutions of the HDAC inhibitors and control reference compound (1-(5-(3-((4-(1,3,4-oxadiazol-2-yl)phenoxy)methyl)-1,2,4-oxadiazol-5-yl)thiophen-2-yl)-2,2,2-trifluoroethanone) are made by first resuspending the lyophilized compound to a final concentration of 10 mM in 100% DMSO. Stocks of 70 µl aliquots of the 10 mM compound in DMSO are prepared and stored at −20° C. From one stock aliquot of each compound to be tested and the reference compound, a 16-point serial dilution is prepared according to Table 1 using a 125 µl 16-channel Matrix multi-channel pipette.

2 µl (200×) of each diluted solution and each control (full activity: 100% DMSO alone or full inhibition 1 mM) is stamped into V-bottom polypropylene 384-well compound plates using either the Bravo, Janus, or 12.5 µl 16-channel Matrix multi-channel pipette. Each well with the 200× compound solution is diluted 1:20 by the addition of 38 µl Jurkat assay buffer+DMSO (9.5% DMSO, RPMI without phenol red, 0.09% FBS, 9 mM Hepes, and 0.9 mM Sodium Pyruvate equilibrated to room temperature)

Prepare 5× (500 µM) Boc-Lys(Tfa)-AMC Substrate.

5× (500 µM) substrate is prepared just prior to the addition to the assay. The 5× substrate is prepared by diluting a 100 mM Boc-Lys(Tfa)-AMC in DMSO solution 1:200 by adding it drop-wise to Jurkat assay medium (RPMI without phenol red, 0.1% FBS, 10 mM Hepes, and 1 mM Sodium Pyruvate equilibrated to 37° C.) while vortexing at slow speed to prevent precipitation.

Prepare 3× Lysis Buffer.

10 ml of 3× lysis buffer is prepared with 8.8 ml of 3× stock lysis buffer (50 mM Tris-HCl, pH 8.0, 137 mM NaCl, 2.7 mM KCl, 1 mM $MgCl_2$, 1% Nonidet P40 Substitute equilibrated to room temperature) and 1.2 ml of 3 mg/ml Trypsin equilibrated to room temperature.

Assay.

5 µl of each solution of 1:20 diluted compound from above is transferred to the Greiner microtitre assay plates with 75,000 cells/well using the Bravo. Cells are then incubated for 2 hours at 37° C. and 5% $CO_2$. The assay is then started by adding 10 µl of 5× (500 µM) substrate to the assay plate using either the Bravo or 16-channel Matrix multi-channel pipette. The cells are then incubated for 3 hours at 37° C. and 5% $CO_2$. Next, 25 µl of 3× lysis buffer is added to each well using either the 125 µl 16 channel pipette or the Bravo. The assay plate is then incubated overnight (15-16 hours) at 37° C. and 5% $CO_2$. The following day, the plates are shaken on an orbital shaker for 1 minute at 900 rpm. Finally the top read fluorescence (Excitation: 355 nm, Emission: 460 nm) is measured using PerkinElmer EnVision.

Example 16

Using the synthetic methods similar to those described above and the assay protocols described above, the following compounds were synthesized and tested.

| Chemical Name | Structure | Biochemical HDAC-4 $IC_{50}$ (µM) | Cellular $IC_{50}$ (µM) |
|---|---|---|---|
| (1S*,2S*,3S*)-2-(4-Bromophenyl)-1-fluoro-N-hydroxy-3-phenylcyclopropanecarboxamide | 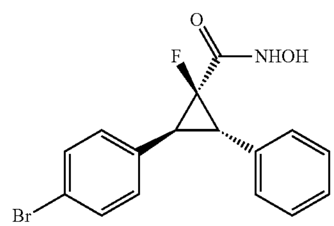 | 0.06 | 0.87 |
| (1R*,2S*,3S*)-2-(8-Chloro-2,3-dihydrobenzo[b][1,4]dioxin-6-yl)-1-fluoro-N-hydroxy-3-phenylcyclopropanecarboxamide | 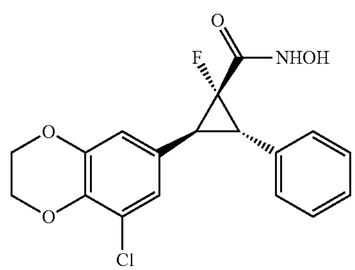 | 6.47 | 40 |
| (1S,2S,3S)-1-Fluoro-N-hydroxy-2-(4-(5-methylpyrimidin-2-yl)phenyl)-3-phenylcyclopropanecarboxamide | 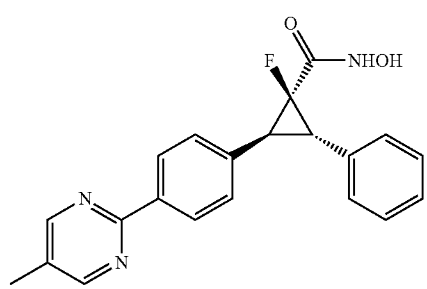 | 0.02 | 0.12 |
| (1S,2S,3S)-1-Chloro-N-hydroxy-2-(4-(5-methylpyrimidin-2-yl)phenyl)-3-phenylcyclopropanecarboxamide | 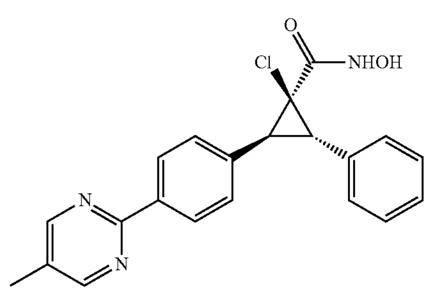 | 0.11 | 1.1 |

-continued

| Chemical Name | Structure | Biochemical HDAC-4 IC$_{50}$ (μM) | Cellular IC$_{50}$ (μM) |
|---|---|---|---|
| (1R,2R,3R)-1-Chloro-N-hydroxy-2-(4-(5-methylpyrimidin-2-yl)phenyl)-3-phenylcyclopropanecarboxamide | 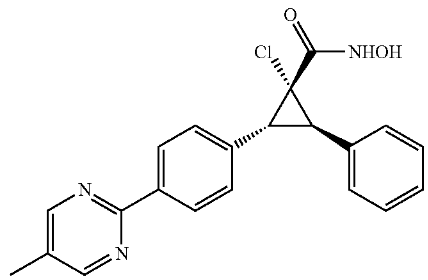 | 1.58 | 15.3 |
| (1R,2R,3R)-1-Fluoro-N-hydroxy-2-(4-(5-methylpyrimidin-2-yl)phenyl)-3-phenylcyclopropanecarboxamide | 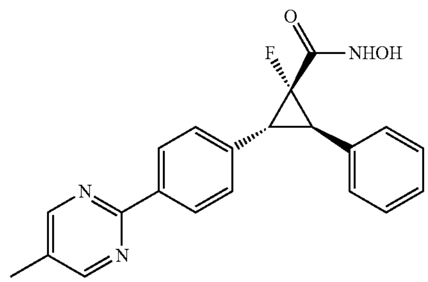 | 1.43 | 8.9 |
| (1S,2S,3S)-2-(4-(5-(Difluoromethoxy)pyrimidin-2-yl)phenyl)-1-fluoro-N-hydroxy-3-phenylcyclopropanecarboxamide | 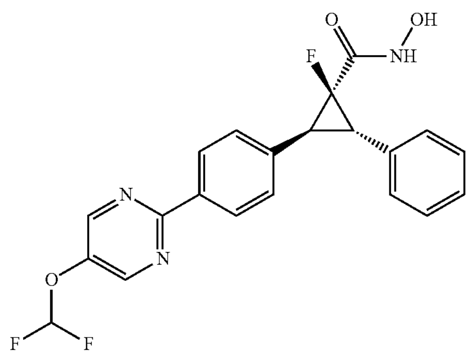 [SMILES: O=C(NO)[C@]1(F)[C@H](c2ccccc2)[C@H]1c1ccc(-c2ncc(OC(F)F)cn2)cc1] | 0.04 | 0.22 |
| (1R,2R,3R)-2-(4-(5-(Difluoromethoxy)pyrimidin-2-yl)phenyl)-1-fluoro-N-hydroxy-3-phenylcyclopropanecarboxamide | 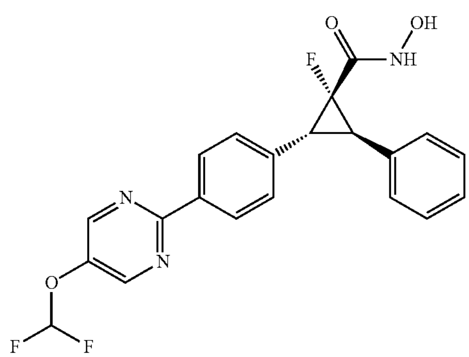 [SMILES: O=C(NO)[C@@]1(F)[C@@H](c2ccccc2)[C@@H]1c1ccc(-c2ncc(OC(F)F)cn2)cc1] | 26 | >50 |
| (1R*,2S*,3S*)-2-(4-(2-Cyclopropyloxazol-5-yl)phenyl)-1-fluoro-N-hydroxy-3-phenylcyclopropanecarboxamide | 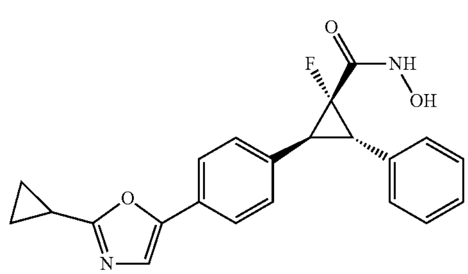 [SMILES: O=C(NO)[C@@]1(F)[C@H](c2ccccc2)[C@H]1c1ccc(-c2cnc(C3CC3)o2)cc1] | 4.65 | 28 |

-continued

| Chemical Name | Structure | Biochemical HDAC-4 IC$_{50}$ (μM) | Cellular IC$_{50}$ (μM) |
| --- | --- | --- | --- |
| (1S*,2S*,3S*)-2-(4-(2-Cyclopropyloxazol-5-yl)phenyl)-1-fluoro-N-hydroxy-3-phenylcyclopropanecarboxamide | 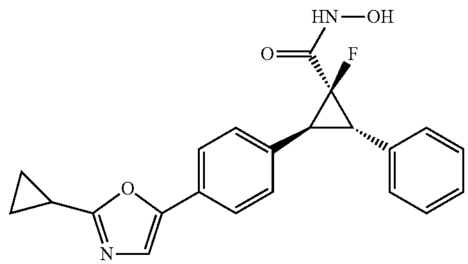 [SMILES: O=C(NO)[C@]1(F)[C@H](c2ccccc2)[C@H]1c1ccc(-c2cnc(C3CC3)o2)cc1] | 0.02 | 0.31 |
| (1S,2R,3S)-1-Fluoro-2-(2-(4-fluorophenyl)thiazol-5-yl)-N-hydroxy-3-phenylcyclopropanecarboxamide | 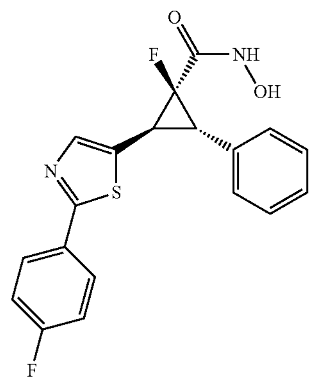 [SMILES: O=C(NO)[C@]1(F)[C@H](c2ccccc2)[C@H]1c1cnc(-c2ccc(F)cc2)s1] | 0.06 | 0.69 |
| (1S,2S,3S)-1-Fluoro-N-hydroxy-2-phenyl-3-(4-(4-(trifluoromethyl)pyrimidin-2-yl)phenyl)cyclopropanecarboxamide | 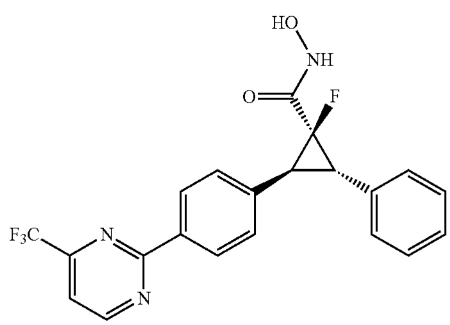 [SMILES: O=C(NO)[C@]1(F)[C@H](c2ccccc2)[C@H]1c1ccc(-c2nccc(C(F)(F)F)n2)cc1] | 0.04 | 0.26 |
| (1R,2R,3R)-1-Fluoro-N-hydroxy-2-phenyl-3-(4-(4-(trifluoromethyl)pyrimidin-2-yl)phenyl)cyclopropanecarboxamide | 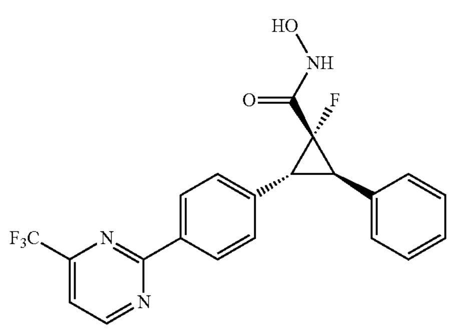 [SMILES: O=C(NO)[C@@]1(F)[C@@H](c2ccccc2)[C@@H]1c1ccc(-c2nccc(C(F)(F)F)n2)cc1] | 6.87 | >50 |

-continued

| Chemical Name | Structure | Biochemical HDAC-4 IC$_{50}$ (μM) | Cellular IC$_{50}$ (μM) |
|---|---|---|---|
| (1S,2S,3S)-1-Fluoro-2-(4-(5-fluoropyrimidin-2-yl)phenyl)-N-hydroxy-3-phenylcyclopropanecarboxamide | 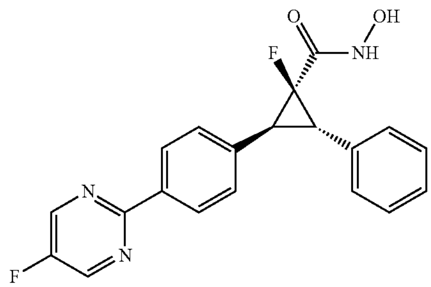 [SMILES: O=C(NO)[C@]1(F)[C@H](c2ccccc2)[C@H]1c1ccc(-c2ncc(F)cn2)cc1] | 0.01 | 0.12 |
| (1R,2R,3R)-1-Fluoro-2-(4-(5-fluoropyrimidin-2-yl)phenyl)-N-hydroxy-3-phenylcyclopropanecarboxamide | 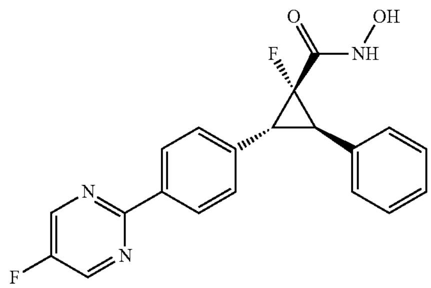 [SMILES: O=C(NO)[C@@]1(F)[C@@H](c2ccccc2)[C@@H]1c1ccc(-c2ncc(F)cn2)cc1] | 0.41 | 4.5 |
| (1R*,2S*,3S*)-2-(2-Cyclopropylpyridin-4-yl)-1-fluoro-N-hydroxy-3-phenylcyclopropanecarboxamide | 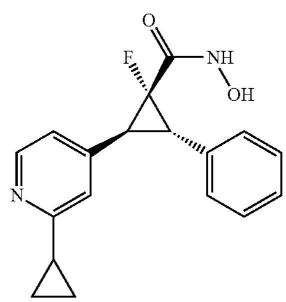 [SMILES: O=C(NO)[C@@]1(F)[C@H](c2ccccc2)[C@H]1c1ccnc(C2CC2)c1] | >50 | >50 |

While some embodiments have been shown and described, various modifications and substitutions may be made thereto without departing from the spirit and scope of the invention. For example, for claim construction purposes, it is not intended that the claims set forth hereinafter be construed in any way narrower than the literal language thereof, and it is thus not intended that exemplary embodiments from the specification be read into the claims. Accordingly, it is to be understood that the present invention has been described by way of illustration and not limitations on the scope of the claims.

The invention claimed is:

1. A compound of Formula I

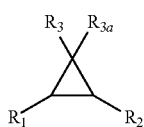

Formula I or a pharmaceutically acceptable salt thereof wherein:
$R_1$ and $R_2$ are independently chosen from optionally substituted aryl and optionally substituted heteroaryl;
$R_3$ is chosen from —C(O)NH(OH) and —N(OH)C(O)R$_4$;
$R_{3a}$ is halo; and
$R_4$ is chosen from hydrogen and lower alkyl.

2. The compound of claim 1, or a pharmaceutically acceptable salt thereof, wherein the compound of Formula I is chosen from compounds of Formula II.

Formula II

3. The compound of claim 1, or a pharmaceutically acceptable salt thereof, wherein the compound of Formula I is chosen from compounds of Formula III.

Formula III

4. The compound of claim 1, or a pharmaceutically acceptable salt thereof, wherein $R_{3a}$ is fluoro or chloro.

5. The compound of claim 4, or a pharmaceutically acceptable salt thereof, wherein $R_{3a}$ is fluoro.

6. The compound of claim 1, or a pharmaceutically acceptable salt thereof, wherein $R_3$ is —C(O)NH(OH).

7. The compound of claim 1, or a pharmaceutically acceptable salt thereof, wherein $R_3$ is —N(OH)C(O)$R_4$ wherein $R_4$ is hydrogen.

8. The compound of claim 1, or a pharmaceutically acceptable salt thereof, wherein $R_3$ is —N(OH)C(O)$R_4$ wherein $R_4$ is methyl.

9. The compound of claim 1, or a pharmaceutically acceptable salt thereof, wherein $R_2$ is chosen from aryl and heteroaryl, each of which is optionally substituted with one or two groups independently chosen from lower alkyl, halo, hydroxyl, and lower alkoxy.

10. The compound of claim 9, or a pharmaceutically acceptable salt thereof, wherein $R_2$ is chosen from aryl optionally substituted with one or two groups independently chosen from lower alkyl, halo, hydroxyl, and lower alkoxy.

11. The compound of claim 10, or a pharmaceutically acceptable salt thereof, wherein $R_2$ is chosen from phenyl, 2-methylphenyl, and 3-fluoro-2-methylphenyl.

12. The compound of claim 11, or a pharmaceutically acceptable salt thereof, wherein $R_2$ is phenyl.

13. The compound of claim 9, or a pharmaceutically acceptable salt thereof, wherein $R_2$ is chosen from heteroaryl optionally substituted with one or two groups independently chosen from lower alkyl, halo, hydroxyl, and lower alkoxy.

14. The compound of claim 13, or a pharmaceutically acceptable salt thereof, wherein $R_2$ is chosen from pyridin-3-yl and 6-oxo-1,6-dihydropyridin-2-yl, each of which is optionally substituted with one or two groups independently chosen from lower alkyl, halo, hydroxyl, and lower alkoxy.

15. The compound of claim 14, or a pharmaceutically acceptable salt thereof, wherein $R_2$ is chosen from 2-methylpyridin-3-yl and 1-methyl-6-oxo-1,6-dihydropyridin-2-yl.

16. The compound of claim 1, or a pharmaceutically acceptable salt thereof, wherein $R_1$ is chosen from aryl and heteroaryl, each of which is optionally substituted with 1, 2, or 3 groups independently chosen from
  halo,
  cyclopropyl,
  trifluoromethyl,
  lower alkyl optionally substituted with 1, 2 or 3 groups independently chosen from halo, lower alkoxy, and hydroxyl,
  phenyl optionally substituted with 1 or 2 groups independently chosen from cyclopropyl, halo, difluoromethyl, trifluoromethyl, trifluoromethoxy, difluoromethoxy, and lower alkyl,
  heteroaryl optionally substituted with 1 or 2 groups independently chosen from cyclopropyl, halo, difluoromethyl, trifluoromethyl, trifluoromethoxy, difluoromethoxy, and lower alkyl, and
  -L-(CR$_5$R$_6$)$_n$—N(R$_7$)R$_8$ where L is chosen from —C(O)NR$_9$— and —NR$_{10}$—, n is 1 or 2, each occurrence of R$_5$ and R$_6$ is independently selected from hydrogen and lower alkyl, R$_7$ is hydrogen or lower alkyl, and R$_8$ is hydrogen or lower alkyl or R$_7$ and R$_8$, taken together with the nitrogen to which they are bound, form an optionally substituted 4- to 8-membered heterocycloalkyl ring, R$_9$ is hydrogen, and R$_{10}$ is selected from hydrogen and lower alkyl.

17. The compound of claim 16, or a pharmaceutically acceptable salt thereof, wherein $R_1$ is chosen from 1,2,3,4-tetrahydroquinolin-6-yl, 1H-pyrazol-4-yl, 2,3-dihydrobenzo[b][1,4]dioxin-6-yl, benzo[d]oxazol-6-yl, benzo[d]thiazol-6-yl, chroman-6-yl, phenyl, pyridazin-4-yl, pyridin-3-yl, pyridin-4-yl, and thiazol-5-yl, each of which is optionally substituted with 1, 2, or 3 groups independently chosen from
  halo,
  cyclopropyl,
  lower alkyl optionally substituted with 1, 2, or 3 groups independently chosen from halo, lower alkoxy, and hydroxyl,
  phenyl optionally substituted with halo,
  oxazol-5-yl optionally substituted with cyclopropyl,
  pyrimidin-4-yl optionally substituted with 1 or 2 groups independently chosen from halo, difluoromethoxy, difluoromethyl, trifluoromethoxy, trifluoromethyl and lower alkyl,
  pyrimidin-2-yl optionally substituted with 1 or 2 groups independently chosen from halo, difluoromethoxy, difluoromethyl, trifluoromethoxy, trifluoromethyl and lower alkyl,
  pyrazin-2-yl optionally substituted with 1 or 2 groups independently chosen from halo, difluoromethoxy, difluoromethyl, trifluoromethoxy, trifluoromethyl or lower alkyl,
  pyridin-2-yl optionally substituted with 1 or 2 groups independently chosen from halo, difluoromethoxy, difluoromethyl, trifluoromethoxy, trifluoromethyl or lower alkyl, and
  -L-(CR$_5$R$_6$)$_n$—N(R$_7$)R$_8$ where L is chosen from —C(O)NR$_9$— and —NR$_{10}$—, n is 1 or 2, each occurrence of R$_5$ and R$_6$ is independently selected from hydrogen and lower alkyl, R$_7$ is hydrogen or lower alkyl, and R$_8$ is hydrogen or lower alkyl or R$_7$ and R$_8$, taken together with the nitrogen to which they are bound, form an optionally substituted 4- to 8-membered heterocycloalkyl ring, R$_9$ is hydrogen, and R$_{10}$ is selected from hydrogen and lower alkyl.

18. The compound of claim 17, or a pharmaceutically acceptable salt thereof, wherein $R_1$ is chosen from 1,2,3,4-tetrahydroquinolin-6-yl, 1H-pyrazol-4-yl, 2,3-dihydrobenzo[b][1,4]dioxin-6-yl, benzo[d]oxazol-6-yl, benzo[d]thiazol-6-yl, chroman-6-yl, phenyl, pyridazin-4-yl, pyridin-3-yl, pyridin-4-yl, and thiazol-5-yl, each of which is optionally substituted with 1, 2, or 3 groups independently chosen from
  2-(trifluoromethyl)pyrimidin-4-yl,
  2-cyclopropyloxazol-5-yl,
  2-hydroxypropan-2-yl,
  4-(trifluoromethyl)pyrimidin-2-yl,
  4-fluorophenyl,
  5-(trifluoromethyl)pyridin-2-yl,
  5-fluoropyrimidin-2-yl,
  5-chloropyrimidin-2-yl,
  5-methylpyrimidin-2-yl,
    5-(difluoromethoxy)pyrimidin-2-yl,
    5-(difluoromethyl)pyrimidin-2-yl,
    2-methylpyrimidin-5-yl,
    5-fluoropyridin-2-yl,
    5-(trifluoromethyl)pyrazin-2-yl,
  bromo,
  chloro,
  cyclopropyl,
  fluoro, and
  oxazol-5-yl.

19. The compound of claim 18, or a pharmaceutically acceptable salt thereof, wherein $R_1$ is chosen from (1-(5-(trifluoromethyl)pyridin-2-yl)-1H-pyrazol-4-yl, 2-(2-(trifluoromethyl)pyrimidin-4-yl)thiazol-5-yl, 2-(2-hydroxypropan-2-yl)benzo[d]oxazol-6-yl, 2-(2-hydroxypropan-2-yl)benzo[d]thiazol-6-yl, 2-(2-hydroxypropan-2-yl)pyridin-4-yl, 2-(2-hydroxypropan-2-yl)thiazol-5-yl, 2-(4-fluorophenyl)thiazol-5-yl, 2-(5-fluoropyrimidin-2-yl)thiazol-5-yl, 2-cyclopropyl-5-fluoropyridin-4-yl, 2-cyclopropylbenzo[d]oxazol-6-yl, 2-cyclopropylpyridin-4-yl, 2-cyclopropylthiazol-5-yl, 3-(2-cyclopropyloxazol-5-yl)phenyl, 3-(5-fluoropyrimidin-2-yl)phenyl, 4-(2-cyclopropyloxazol-5-yl)phenyl, 4-(4-(trifluoromethyl)pyrimidin-2-yl)phenyl, 4-(5-fluoropyrimidin-2-yl)phenyl, 4-(5-methylpyrimidin-2-yl)phenyl, 4-(oxazol-5-yl)phenyl, 4-bromophenyl, 6-cyclopropylpyridazin-4-yl, 8-chloro-2,3-dihydrobenzo[b][1,4]dioxin-6-yl, 8-chloro-4,4-difluoro-1,2,3,4-tetrahydroquinolin-6-yl, and 8-chloro-4,4-difluorochroman-6-yl.

20. A compound, or a pharmaceutically acceptable salt thereof, chosen from (1S,2S,3S)-1-fluoro-N-hydroxy-2-(4-(5-methylpyrimidin-2-yl)phenyl)-3-phenylcyclopropanecarboxamide, (1S,2S,3S)-2-(3-(2-cyclopropyloxazol-5-yl)phenyl)-1-fluoro-N-hydroxy-3-phenylcyclopropanecarboxamide, (1S,2S,3S)-1-fluoro-2-(3-(5-fluoropyrimidin-2-yl)phenyl)-N-hydroxy-3-phenylcyclopropanecarboxamide, (1S,2S,3S)-1-chloro-N-hydroxy-2-(4-(oxazol-5-yl)phenyl)-3-phenylcyclopropanecarboxamide, (1S,2S,3S)-2-(4-(2-cyclopropyloxazol-5-yl)phenyl)-1-fluoro-N-hydroxy-3-phenylcyclopropanecarboxamide, (1S,2S,3S)-1-fluoro-N-hydroxy-2-(4-(oxazol-5-yl)phenyl)-3-phenylcyclopropanecarboxamide, (1S,2S,3S)-1-fluoro-N-hydroxy-2-phenyl-3-(4-(4-(trifluoromethyl)pyrimidin-2-yl)phenyl)cyclopropanecarboxamide, (1S,2S,3S)-2-(4-bromophenyl)-1-fluoro-N-hydroxy-3-phenylcyclopropanecarboxamide, (1S,2S,3S)-1-chloro-N-hydroxy-2-(4-(5-methylpyrimidin-2-yl)phenyl)-3-phenylcyclopropanecarboxamide, (1S,2S,3S)-1-fluoro-2-(4-(5-fluoropyrimidin-2-yl)phenyl)-N-hydroxy-3-phenylcyclopropanecarboxamide, (1S,2S,3S)-2-(4-(5-(difluoromethoxy)pyrimidin-2-yl)phenyl)-1-fluoro-N-hydroxy-3-phenylcyclopropanecarboxamide, (1S,2S,3S)-1-fluoro-N-hydroxy-2-phenyl-3-(4-(5-(trifluoromethyl)pyrimidin-2-yl)phenyl)cyclopropanecarboxamide, (1S,2S,3S)-2-(4-(5-(difluoromethyl)pyrimidin-2-yl)phenyl)-1-fluoro-N-hydroxy-3-phenylcyclopropanecarboxamide, (1S,2S,3S)-2-(4-(5-chloropyrimidin-2-yl)phenyl)-1-fluoro-N-hydroxy-3-phenylcyclopropanecarboxamide, (1S,2S,3S)-1-fluoro-N-hydroxy-2-(4-(2-methylpyrimidin-5-yl)phenyl)-3-phenylcyclopropanecarboxamide, (1S,2S,3S)-1-fluoro-N-hydroxy-2-phenyl-3-(4-(5-(trifluoromethyl)pyrazin-2-yl)phenyl)cyclopropanecarboxamide, (1S,2S,3S)-2-(6-((2-(diethylamino)ethyl)amino)pyridin-3-yl)-1-fluoro-N-hydroxy-3-phenylcyclopropanecarboxamide, N—((S)-1-(dipropylamino)propan-2-yl)-4-((1 S,2S,3S)-2-fluoro-2-(hydroxycarbamoyl)-3-phenylcyclopropyl)benzamide, 4-((1 S,2S,3S)-2-fluoro-2-(hydroxycarbamoyl)-3-phenylcyclopropyl)-N-(2-(pyrrolidin-1-yl)ethyl)benzamide, (1R,2S,3S)-1-fluoro-N-hydroxy-2-(2-(2-hydroxypropan-2-yl)pyridin-4-yl)-3-o-tolylcyclopropanecarboxamide, (1S,2S,3S)-1-fluoro-N-hydroxy-2-(2-(2-hydroxypropan-2-yl)pyridin-4-yl)-3-phenylcyclopropanecarboxamide, (1R,2S,3S)-2-(2-cyclopropylpyridin-4-yl)-1-fluoro-N-hydroxy-3-phenylcyclopropanecarboxamide, (1S,2S,3S)-2-(2-cyclopropyl-5-fluoropyridin-4-yl)-1-fluoro-N-hydroxy-3-phenylcyclopropanecarboxamide, (1S,2S,3S)-2-(2-cyclopropylpyridin-4-yl)-1-fluoro-N-hydroxy-3-phenylcyclopropanecarboxamide, (1S,2S,3S)-2-(6-cyclopropylpyridazin-4-yl)-1-fluoro-N-hydroxy-3-phenylcyclopropanecarboxamide, (1S,2S,3S)-2-(6-cyclopropylpyridazin-4-yl)-1-fluoro-N-hydroxy-3-o-tolylcyclopropanecarboxamide, (1S,2S,3S)-2-(6-cyclopropylpyridazin-4-yl)-1-fluoro-3-(3-fluoro-2-methylphenyl)-N-hydroxycyclopropanecarboxamide, (1S,2S,3S)-2-(8-chloro-4,4-difluorochroman-6-yl)-1-fluoro-N-hydroxy-3-phenylcyclopropanecarboxamide, (1R,2S,3S)-2-(8-chloro-2,3-dihydrobenzo[b][1,4]dioxin-6-yl)-1-fluoro-N-hydroxy-3-phenylcyclopropanecarboxamide, (1 S,2S,3S)-2-(8-chloro-4,4-difluoro-1,2,3,4-tetrahydroquinolin-6-yl)-1-fluoro-N-hydroxy-3-phenylcyclopropanecarboxamide, (1S,2S,3S)-2-(8-chloro-2,3-dihydrobenzo[b][1,4]dioxin-6-yl)-1-fluoro-N-hydroxy-3-phenylcyclopropanecarboxamide, (1S,2S,3S)-2-(2-cyclopropylbenzo[d]oxazol-6-yl)-1-fluoro-N-hydroxy-3-phenylcyclopropanecarboxamide, (1S,2S,3S)-1-fluoro-N-hydroxy-2-(2-(2-hydroxypropan-2-yl)benzo[d]oxazol-6-yl)-3-phenylcyclopropanecarboxamide, (1S,2S,3S)-1-fluoro-N-hydroxy-2-(2-(2-hydroxypropan-2-yl)benzo[d]thiazol-6-yl)-3-phenylcyclopropanecarboxamide, (1S,2S,3S)-1-fluoro-2-(3-fluoro-2-methylphenyl)-N-hydroxy-3-(1-(5-(trifluoromethyl)pyridin-2-yl)-1H-pyrazol-4-yl)cyclopropanecarboxamide, (1S,2R,3S)-2-(2-cyclopropylthiazol-5-yl)-1-fluoro-3-(3-fluoro-2-methylphenyl)-N-hydroxycyclopropanecarboxamide, (1S,2S,3R)-1-fluoro-2-(3-fluoro-2-methylphenyl)-3-(2-(5-fluoropyrimidin-2-yl)thiazol-5-yl)-N-hydroxycyclopropanecarboxamide, (1S,2R,3S)-1-fluoro-2-(2-(4-fluorophenyl)thiazol-5-yl)-N-hydroxy-3-(2-methylpyridin-3-yl)cyclopropanecarboxamide, (1S,2S,3R)-1-fluoro-2-(3-fluoro-2-methylphenyl)-3-(2-(4-fluorophenyl)thiazol-5-yl)-N-hydroxycyclopropanecarboxamide, (1S,2R,3S)-1-fluoro-2-(2-(4-fluorophenyl)thiazol-5-yl)-N-hydroxy-3-phenylcyclopropanecarboxamide, (1S,2R,3S)-1-fluoro-2-(2-(5-fluoropyridin-2-yl)thiazol-5-yl)-N-hydroxy-3-phenylcyclopropanecarboxamide, and (1S,2R,3S)-1-fluoro-2-(2-(5-fluoropyridin-2-yl)thiazol-5-yl)-N-hydroxy-3-o-tolylcyclopropanecarboxamide.

21. A pharmaceutical composition comprising a compound of claim 1, or a pharmaceutically acceptable salt thereof, and at least one pharmaceutically acceptable excipient.

* * * * *